US011505592B2

(12) United States Patent
Paterno et al.

(10) Patent No.: US 11,505,592 B2
(45) Date of Patent: **\*Nov. 22, 2022**

(54) DIAGNOSIS AND THERAPY OF MULTIPLE SCLEROSIS

(71) Applicant: PRINDEX S.R.L., Naples (IT)

(72) Inventors: Roberto Paterno, Naples (IT); Mariarosaria Santillo, Naples (IT); Vittorio Enrico Avvedimento, Caserta (IT); Luigi Michele Pavone, Naples (IT)

(73) Assignee: PRINDEX S.R.L., Naples (IT)

( * ) Notice: Subject to any disclaimer, the term of this patent is extended or adjusted under 35 U.S.C. 154(b) by 0 days.

This patent is subject to a terminal disclaimer.

(21) Appl. No.: 16/857,794

(22) Filed: Apr. 24, 2020

(65) Prior Publication Data

US 2020/0308251 A1  Oct. 1, 2020

Related U.S. Application Data

(62) Division of application No. 15/192,064, filed on Jun. 24, 2016, now Pat. No. 10,633,427.

(30) Foreign Application Priority Data

Jun. 26, 2015  (EP) .................. EP15174144

(51) Int. Cl.
| | | |
|---|---|---|
| *C07K 14/705* | (2006.01) | |
| *G01N 33/564* | (2006.01) | |
| *C07K 14/47* | (2006.01) | |
| *G01N 33/94* | (2006.01) | |
| *A61K 39/00* | (2006.01) | |
| *C07K 14/72* | (2006.01) | |
| *C07K 16/28* | (2006.01) | |
| *C07K 16/40* | (2006.01) | |
| *C12N 9/02* | (2006.01) | |
| *A61K 38/00* | (2006.01) | |

(52) U.S. Cl.
CPC ........ *C07K 14/70571* (2013.01); *A61K 39/00* (2013.01); *C07K 14/4713* (2013.01); *C07K 14/705* (2013.01); *C07K 14/723* (2013.01); *C07K 16/286* (2013.01); *C07K 16/40* (2013.01); *C12N 9/0036* (2013.01); *C12Y 106/03001* (2013.01); *G01N 33/564* (2013.01); *G01N 33/942* (2013.01); *A61K 38/00* (2013.01); *G01N 2333/70571* (2013.01); *G01N 2333/90209* (2013.01); *G01N 2800/285* (2013.01); *G01N 2800/52* (2013.01)

(58) Field of Classification Search
CPC .......... C07K 14/70571; C07K 14/4713; C07K 14/705; C07K 14/723; C07K 16/286; C07K 16/40; A61K 39/00; C12N 9/0036; C12Y 106/03001; G01N 33/564; G01N 33/942

See application file for complete search history.

(56) References Cited

U.S. PATENT DOCUMENTS

2003/0113798 A1  6/2003  Burmer et al.
2016/0017022 A1*  1/2016  Vartanian ............... A61P 43/00
424/133.1

FOREIGN PATENT DOCUMENTS

WO  WO2006113557 A2 *  10/2006
WO  2011/085081 A2  7/2011

OTHER PUBLICATIONS

Usuda et al., "Immunoelectron microscopy of peroxisomes employing the antibody for the SKL sequence PTS1 C-terminus common to peroxisomal enzymes", J Histochem Cytochem. Sep. 1999;47(9):1119-26 (Year: 1999).*
Valentina, Ucci, "5-HT2a receptor pathway in oligodendrocyte differentiation: its involvement in Multiple Sclerosis pathogenesis" University of Naples (Year: 2013).*
B. Ayoglu et al., "Autoantibody profiling in Multiple Sclerosis Using Arrays of Human Protein Fragments," Molecular & Cellular Proteomics, vol. 12, No. 9, Sep. 1, 2013 pp. 2657-2672.
O'Hara et al. "Interferon beta1-a and selective anti-5HT2a receptor antagonists inhibit infection of human glial cells by JC virus," Virus Research, vol. 132, No. 1-2, Feb. 15, 2008, pp. 97-103.
Partial European Search Report issued in a related European Application No. EP 16 17 6276 dated Aug. 9, 2016 (9 pages).

* cited by examiner

*Primary Examiner* — Daniel E Kolker
*Assistant Examiner* — Peter Johansen
(74) *Attorney, Agent, or Firm* — Lucas & Mercanti, LLP

(57) ABSTRACT

The serotonin receptor 5HT2A (5HT2aR) and membrane NADPH oxidases (NOX enzymes) are found to be a target of autoantibodies present in Multiple Sclerosis patients. The present invention refers to peptides comprised in the extracellular regions of the human 5HT2aR and/or NOXs for diagnosis and therapy of Multiple Sclerosis.

19 Claims, 29 Drawing Sheets

Figure 1B:
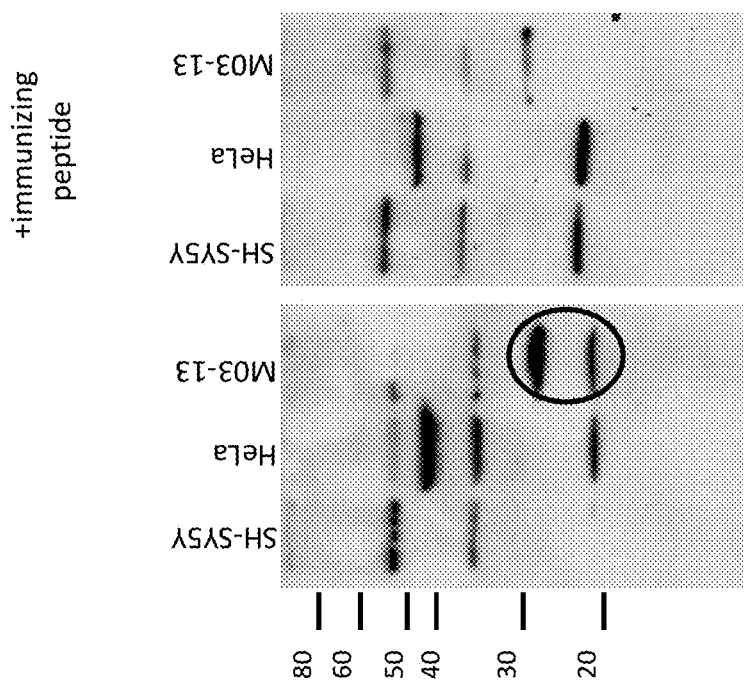

Specification includes a Sequence Listing.

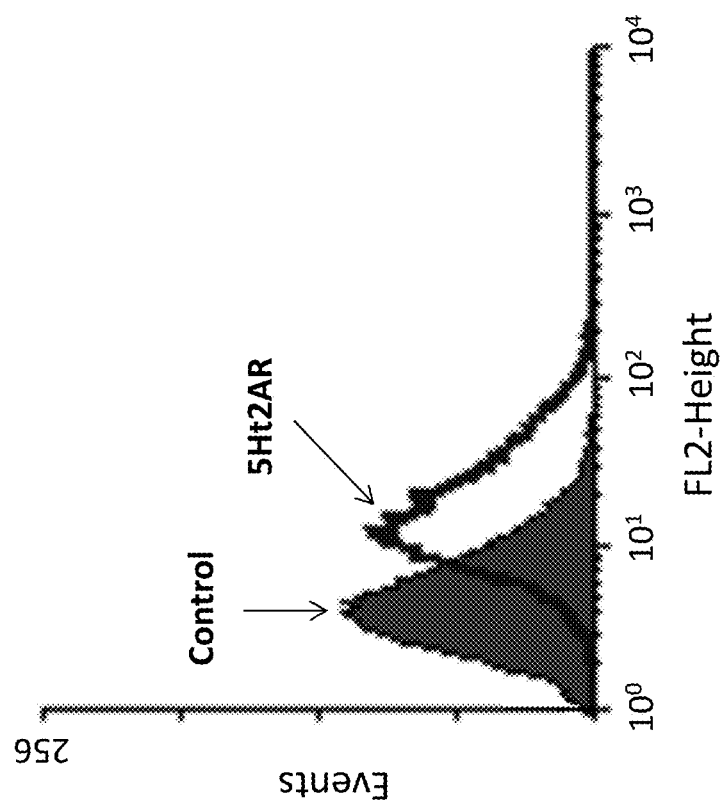

5HT2aR

Loop 1

| Peptide | SEQ ID NO | Sequence | | |
|---|---|---|---|---|
| 3 | 12 | -LTILYGYRWPAAS---------------------KL------ | 15 |
| 41 | 50 | CLTILYGYRWPAAS---------------------KLC----- | 17 |
| 8 | 17 | -LTILYGYRWPLP-------------------SKL-------- | 15 |
| 40 | 49 | CLTILYGYRWPLPSCLYGYRWP-------LPSKLSC | 29 |
| 35 | 44 | CLTILYGYRWPLPS----------------------KLC---- | 17 |
| loop1 | 7 | -LTILYGYRWPLPS--------------------KLC------ | 16 |
| 29 | 38 | --TILYGYRWPLPS-------------------KLC------- | 15 |
| 12 | 21 | CLTILYGYRWPLP----SCKESSNE---DVIGALLC | 29 |
| 20 | 29 | CL----YGYRWPLPSCKESSNE---DVIGALLC | 29 |
| 5 | 14 | -------YRWPLPSKL-------------------- | 9 |
| 32 | 41 | CL----YGYRWPLPSKLSCYSNDFN---SGEANTSC | 29 |
| 36 | 45 | CL----YGYRWPLPSKLSC-SDAFNWTVDSENR-C | 29 |
| 43 | 52 | CL----YGYRWPLPSKLSC-SGEAN-TSDAFNWTC | 29 |
| 14 | 23 | -------GYRWPLPSK----------------- | 9 |

* * * * *

Fig. 15A

5HT2aR
Loop 2

| Peptide | SEQ ID NO | | |
|---|---|---|---|
| 7 | 16 (AA 2-29) | LQDDSKVFKEGSS------ | ----------CMDILSEENTSLSSC 28 |
| 28 | 37 (AA 2-29) | ----DSKVFKEGSSLLA-- | ----------CMDILSEENTSLSSC 28 |
| 33 | 42 | -QDDSKVFKEGAA------ | ----------------------LLA 15 |
| 16 | 25 (AA 2-29) | ----DSKVFKEGSSLLA-- | ----------CKESSNEDVIGALLC 28 |
| 38 | 47 (AA 2-29) | -------VFKEGSSLLAD- | --------DNCKESSNEDVIGALLC 28 |
| 48 | 57 (AA 2-29) | LQDDSKVFKEGSS------ | ----------CKESSNEDVIGALLC 28 |
| 46 | 55 (AA 2-29) | ----DSKVFKEGSSLLA-- | ----------CSENRTNLSSEGSLC 28 |
| loop2 | 8 | LQDDSKVFKEGSC------ | ----------------------LLADDN 19 |
| 37 | 46 (AA 2-29) | ----DSKVFKEGSSLLACSGEANTSDAFNWT------C 28 |
| 47 | 56 (AA 2-29) | -------VFKEGSSLLA-- | ------DDNCSDAFNWTVDSENRC 28 |
|   |   | *****:* | |

Fig. 15B

5HT2aR
Loop 3

| Peptide | SEQ ID NO | | |
|---|---|---|---|
| 16 | 25 | CD----SKVFKEGSSLLA-------CKESSNEDVIGALLC | 29 |
| 38 | 47 | C-------VFKEGSSLLADDNCKESSNEDVIGALLC | 29 |
| 48 | 57 | CLQDDSKVFKEGSS-------CKESSNEDVIGALLC | 29 |
| loop3 | 9 | VI-------------CKESCNEDVIGALL- | 16 |
| 12 | 21 | CLT----ILYGYRWPLP-------SCKESSNEDVIGALLC | 29 |
| 20 | 29 | CL-----YGYRWPLPSKLSCKESSNEDVIGALLC | 29 |
| 42 | 51 | CTR----LYSNDFNSGE-------ACKESSNEDVIGALLC | 29 |
| 44 | 53 | CMD----ILSEENTSLSS------CSKESSNEDVIGA-LC | 29 |
| | | . ***.  ********* * | |

Fig. 15C

5HT2aR N-terminal

```
Peptide  SEQ ID NO
10       19        ------------CLSPSSLSIIHLQE---CMDILSEENTSLSSC------------------------- 29
45       54        -----------C---SSLSLIHLQEKNWCMDILSEENTSLSSC------------------------- 29
11       20        ----------CS--TTNSLMQLNDDT-CMDILSEENTSLSSC-------------------------- 29
17       26        CENTSLSSTTNSLM---------------CMDILSEENTSLSSC------------------------ 29
18       27        ----------CSLSSTTNSLMQLN-----CMDILSEENTSLSSC------------------------ 29
2        11        ----------CLTILYGYRWPLP------SCMDILSEENTSLSSC----------------------- 29
4        13        ----------CL---YGYRWPLPSKLSCMDILSEENTSLSSC-------------------------- 29
26       35        ----------CLS--SEG-SLSPSSLSCMDILSEENTSLSSC-------------------------- 29
39       48        ----------CLS--EENTSLS-STTNCMDILSEENTSLSSC-------------------------- 29
7        16        ----------CLQDDSKVFKEGSS-----CMDILSEENTSLSSC------------------------ 29
28       37        ----------C---DSKVFKEGSSLLACMDILSEENTSLSSC-------------------------- 29
9        18        ----------CMQLNDDTRLYSND-----CMDILSEENTSLSSC------------------------ 29
24       33        ----------C---NDDTRLYSNDFNSCMDILSEENTSLSSC-------------------------- 29
22       31        ----------CSDAFNWTVDSENR-----CMDILSEENTSLSSC------------------------ 29
30       39        ----------C---FNWTVDSENRTNLCMDILSEENTSLSSC-------------------------- 29
nter 6 (AA 1-13)
21       30        -------------------------------MDILCEENTSLSS----------------------- 13
                                                  CMDILSEENTSLSSCMQLNDDTRLYSNDC 29
                                                  ****  *********    ***
nter 6 (AA 1-28)
31       40        MDILCEENTSLSSTTNSLMQLNDDTRLY---SND---------------------------------- 31
6        15        ---------STTNSLMQLNAATRL-------------------------------------------- 15
34       43 (AA1-31) -----------CNSLMQLNDDTRLY---CLSSEGSLSPSSLSC------------------------- 29
1        10        -----------CNSLMQLNDDTRLY---CYSNDFNSGEANTSSC------------------------ 29
15       24        -----------CMDILSEENTSLY---CMDILSEENTSLSSC-------------------------- 29
19       28        -----------C---MQLNDDTRLYSNDCSGEANTSDAFNWTC------------------------- 29
                               CNSLMQLNDDTRLY---CSGEANTSDAFNWTC
                              ****    ***
```

Fig. 15D

NOX
Loop 2

| Peptide | SEQ ID NO | |
|---|---|---|
| Loop2 | 4 | -EWCVNARVNNSDPYSVALSELG-DRQNESYLNFARKRRIKN----PEGGLYL |
| Peptide80 | 137 | -------CRVNNSDPYSVALSELC----QNESYLNFARKRRIKN-----C------- |
| Peptide46 | 103 | CEWSVNARVNNSDPYSC-----------QNESYLNFARKRRIKN-----C------- |
| Peptide6 | 63 | -------------------------------QNESYLNFARKRRIKN-----C------- |
| Peptide5 | 62 | -------------------------------NESYLNFARKAAKNP------------- |
| Peptide29 | 86 | C--------------------------NESYLNFARKAAKNP-----C------- |
| Peptide7 | 64 | CV-----SEQKISEWGKIKES----CQNESYLNFARKRRIKN-----C------- |
| Peptide12 | 69 | --------QKISEWGKIKESPI-PCQNESYLNFARKRRIKN-----C------- |
| Peptide24 | 81 | CN---ITVSEQKISEWGKICQ-------NESYLNFARKRRIKN-----C------- |
| Peptide42 | 99 | CN---ITVSEQKISEWGKIC----------SYLNFARKRIKNPEGC------- |
| Peptide55 | 112 | C----VSEQKISEWGKIKESCG-DRQNESYLNFARKRC----------------- |
| Peptide87 | 144 | CN---ITVSEQKISEWGKI----CG-DRQNESYLNFARKRC----------------- |
| Peptide17 | 74 | CES-LAVHNITVSE-QKIC--------QNESYLNFARKR------C------- |
| Peptide79 | 136 | CES-LAVHNITVSE-QKICG-----DRQNESYLNFARKR------C------- |
| Peptide69 | 126 | C----AVHNITVSE-QKISE-----WCQNESYLNFARKRRIKN-----C------- |
| Peptide9 | 66 | C------VRGQTAESLAVHNI------TCQNESYLNFARKRRIKN-----C------- |
| Peptide18 | 75 | CE-----RIVRGQTAESLAVH--------CQNESYLNFARKRRIKN-----C------- |
| Peptide43 | 100 | C-------QTAESLAVHNITVS-ECQNESYLNFARKRRIKN-----C------- |
| Peptide19 | 76 | C---------------------------RQNESYLNFARKRRIK-----C------- |
| Peptide13 | 70 | C---GDRQNESYLNFARKRC----QNESYLNFARKRRIKN-----C------- |
| Peptide28 | 85 | C---GDRQNESYLNFARKRCGDRQNESYLNFARKR------C------- |
| Peptide47 | 104 | C---FNVEWSVNARVNNSDCGDRQNESYLNFARKR------C------- |
| Peptide72 | 129 | C---------------LGDRQNESYLNFARKR------C------- |
| Peptide23 | 80 | C---SELGDRQNESYLNF--------ACQNESYLNFARKRRIKN-----C------- |
| Peptide53 | 110 | CVALSELGDRQNESYL-----------CQNESYLNFARKRRIKN-----C------- |
| Peptide38 | 95 | C--------------------------RQNESYLNFARKRRIK-----C------- |
| Peptide14 | 71 | ----------------------SYLNFARKRIAAPEG--------- |
| Peptide25 | 82 | C---HGAERIVRGQTAESLC----------SYLNFARKRIKNPEGC------- |
| Peptide2 | 59 | ----------------------------LNFARKRIK------------- |
| Peptide60 | 117 | CSYLNFARKRIKNPEGGLYCG-----DRQNESYLNFARKR------C------- |
| Peptide68 | 125 | C---NFARKRIKNPEG-----CG-----DRQNESYLNFARKR------C------- |
| Peptide8 | 65 | CSYLNFARKRIKNPEGGLYC----------QNESYLNFARKR------C------- |
| Peptide4 | 61 | CSYLNFARKRIKNPEG----------C-----QNESYLNFARKRRIKN-----C------- |
|  |  | ******* |

Fig. 16A

NOX
Loop 3

| Peptide | SEQ ID NO | Sequence |
|---|---|---|
| Peptide67 | 124 | --------C----PYSVALSELGDRQNECITVSEQKISEWGKIK----C------------ |
| Peptide86 | 143 | ---------CNSDPYSVALSELGDR------CITVSEQKISEWGKIK----C------------ |
| Peptide73 | 130 | ---------CNSDPYSVALSELGDR------CVSEQKISEWGKIKESC------------ |
| Peptide71 | 128 | -------------CVNARVNNSDPYSVALC----VSEQKISEWGKIKESC------------ |
| Peptide97 | 154 | -------------CVNARVNNSDPYSVALCT---VSEQKISEWGKIKE---C------------ |
| Peptide94 | 151 | ---------CRVNNSDPYSVALSELCVSEQKISEWGKIKESC------------ |
| Peptide84 | 141 | -CFNVEWSVNARVNNSD---------CVSEQKISEWGKIKESC------------ |
| Peptide98 | 155 | ------CEWSVNARVNNSDPY--------SCVSEQKISEWGKIKESC------------ |
| Peptide55 | 112 (AA 1-32) | ---------C-------VSEQKISEWGKIKESCGDRQNESYLNFARKR--- |
| Peptide87 | 144 (AA 1-32) | ---------CN------------ITVSEQKISEWGKI----CGDRQNESYLNFARKR--- |
| Peptide42 | 99 (AA 1-28) | ---------CN------------ITVSEQKISEWGKI----SYLNFARKRIK |
| Peptide89 | 146 | -------------------------QKISEWGKI---C------------ |
| Peptide65 | 122 | ---------C----SYLNFARKRIKNPEGCITVSEQKISEWGKIK----C------------ |
| Peptide95 | 152 | --CGDRQNESYLNFARKRC-------VSEQKISEWGKIKESC------------ |
| Loop3 | 5 | --HGAERIVRGQTAESLAVHNI-----TVCEQKISEWGKIKECPIPQ------------ |
| Peptide44 | 101 | --CHGAERIVRGQTAESLC---------QKISEWGKIKECPIPC------------ |
| Peptide77 | 134 | -------------CVRGQTAESLAVHNITC-ITVSEQKISEWGKIK----C------------ |
| Peptide82 | 139 | -------------CQTAESLAVHNITVSECVSEQKISEWGKIKESC------------ |
| Peptide66 | 123 | --------CAVHNITVSEQKISEW-----CVSEQKISEWGKIKESC------------ |
| Peptide58 | 115 | CVSEQKISEWGKIKES---C-------CVSEQKISEWGKIKES---C------------ |
| Peptide85 | 142 | CVSEQKISEWGKIKES---CT------VSEQKISEWGKIKE---C------------ |
| Peptide27 | 84 | C----QKISEWGKIKESPIPC------EQKISEWGKIKESPIC------------ |
| Peptide36 | 93 | C----QKISEWGKIKESPIPC------TVSEQKISEWGKIKE---C------------ |
| Peptide92 | 149 | C----QKISEWGKIKESPIPCVHNI--TVSEQKISEWG------C------------ |
| Peptide41 | 98 | C----QKISEWGKIKESPIPC------VSEQKISEWGKIKES---C------------ |
|  |  | *******  |

Fig. 16B

DIAGNOSIS AND THERAPY OF MULTIPLE SCLEROSIS

CROSS-REFERENCE TO RELATED APPLICATION

This application is a divisional of U.S. application Ser. No. 15/192,064, filed Jun. 24, 2016, which claims the benefit of European Patent Application No. 15 174 144.4, filed Jun. 26, 2015, the contents of each of which are incorporated herein by reference.

FIELD OF THE INVENTION

The authors found that the serotonin receptor 5HT2A (5HT2aR) and membrane NADPH oxidases (NOX enzymes) are a target of autoantibodies present in Multiple Sclerosis patients. Thus, the present invention refers to peptides comprised in the extracellular regions of the human 5HT2aR and/or NOXs for diagnosis and therapy of Multiple Sclerosis.

BACKGROUND TO THE INVENTION

Multiple Sclerosis

Multiple sclerosis (MS) is characterized by a chronic inflammatory demyelination, that damages the central nervous system (CNS) (Noseworthy et al., 2000). It is the most common cause of disability in young adults. It is one of the most debilitating medical conditions, not only physically, but also in terms of psychosocial implications.

MS is the most common neurological disease in young adult and, as shown by the descriptive studies, the geographical distribution of the disease is heterogeneous (Rosati, 2001). It concerns mainly the countries in central and northern part of Europe and those non-European regions that in various historical periods have been subject to a significant settlement of populations of northern European ancestry. MS is typically a disease of temperate climates; in both hemispheres its prevalence decreases with decreasing latitude. The comparison between the populations of North America and Europe indicate similar rates of prevalence and similar north-south gradient. Some areas of the world represent real focus of the disease, suggesting that environmental factors might be involved in MS.

In Caucasians, the average rates of total prevalence vary between 30 and 180 cases/100.000 inhabitants (Rosati, 2001) and the incidence is 10-20 new cases/100.000 inhabitants per year. It is most frequently diagnosed between 20 and 40 years, rarely affects children and the elderly. MS is about twice as common in women than in men (Pugliatti et al. 2006).

MS can be considered the result of a complex multifactorial interactions between genetic and environmental factors. The findings of several studies seem to demonstrate that MS is an immune-mediated disease related to T lymphocytes action and induced by external and unknown agents, such as viruses and bacteria, in genetically susceptible individual.

Despite the number of studies on the disease and a multidisciplinary approach to the problem, some pathogenic mechanisms of multiple sclerosis are still obscure and the aetiology is unknown.

At the present time, there are no definitive diagnostic tests for multiple sclerosis. Therefore, it is necessary to use different diagnostic tools: clinical (Trojano and Paolicelli, 2001), laboratory (Luque and Jaffe, 2007) and instrumental diagnosis (Achten and Deblaere, 2008).

1) Clinical diagnosis allows to evaluate: Patient medical history; Evidence of altered sensibility; impaired strength and vision disturbances; Symptoms/signs attributable to white matter lesions are not justified by other diseases; Spatial dissemination of lesions with clinical signs referable to 2 or more lesions; Symptoms/signs attributable to the temporal dissemination of the lesions: two or more relapses.
2) Laboratory diagnosis based on CSF investigations (inflammatory and autoimmune disorders) analyze the intrathecal synthesis of Immunoglobulin G (IgG) and the presence of oligoclonal bands.
3) Instrumental diagnosis comprise: Magnetic Resonance Imaging (MRI) that allows to show pathological foci in the brain stem, cerebellum and spinal cord and the presence of lesions in the corpus callosum and around the ventricles. In addition, through the use of contrast medium it is possible to highlight local impairments in Blood Brain Barrier (BBB) that precede signs of exacerbation and possible injury to the optic nerve; Computerized Axial Tomography (CAT) shows less dense areas around the ventricles corresponding to the plaques in which the myelin is no longer present; Testing of Evoked Potentials (EP) measures the transmission time of sensory messages that travel through the nerves.

The current MS diagnostic procedure is rather long and tortuous thus there is the need for an early diagnosis of MS since an earliest possible therapeutic intervention would be most effective for the long term, even with currently available therapies.

The currently available therapy (β-interferon, steroids, symptomatic therapy) act on the symptomatology and are aimed at slowing the progression of the disease thus, in view of the above considerations, also a etiological therapy would be needed in order to treat permanently the disease.

5HT2a Receptor and Multiple Sclerosis

5HT2A receptor (5HT2aR) belongs to the family of serotonin receptors. There are at least 13 different receptors for serotonin grouped into 7 families based on the mechanism of signal transduction. Except 5-HT3, which is a ligand-gated ion channel, the other members are all G protein-coupled receptors, and in particular, the 5HT2aR is coupled to the Gq/11 (Barnes and Sharp, 1999).

The 5HT2aR activates multiple transduction pathway: a) the $PLA_2$ pathway leading to arachidonic acid (AA) production; b) the PLC pathway, that through an action on phosphatidylinositol 4,5-bisphosphate ($PIP_2$), generates diacyl glycerol (DAG) and increases intracellular $Ca^{2+}$levels activating protein kinase C (PKC); c) it also activates membrane calcium channels promoting calcium influx (Raote et al., 2007).

5HT2aR is expressed by oligodendrocytes where its downstream signaling exerts modulatory effects on myelin formation (Millan et al., 2008).

Further, in relapsing-remitting (RR) MS patients, there is a dysmetabolism of the serotonergic pathway. In these patients disability accumulation during disease progression correlates negatively with the CSF levels of 5-hydroxyindoleacetic acid (5-HIAA), an index of serotonergic activity in the CNS (Markianos et al., 2008).

5HT2aR is used by the JC virus (JCV, from the initials of the patient—John Cunningham—from which the virus was for the first time isolated) polyoma virus to infect cells. JCV has a very restricted tropism, since it is able to replicate only within glial cells (although it can also infect other cell types such as B lymphocytes, hematopoietic progenitor cells and few others) and, in addition, it is the "causal agent" of progressive multifocal leukoencephalopathy (PML), an often fatal disease associated with oligodendrocyte lysis and widespread demyelination (Elphick et al., 2004). The link between MS and JCV has emerged following the onset of PML in MS patients treated with NATALIZUMAB, a humanized monoclonal antibody used in the treatment of autoimmune inflammatory disorders such as MS, Parkinson's and Crohn diseases (Achiron et al., 2005).

Natalizumab is an antibody directed against the integrin alpha4 beta1 also known as VLA4 and thus works by preventing the adhesion and migration of lymphocytes from the vascular bed to the site of inflammation. By blocking the migration of T cells, the central nervous system remains partially immunologically unprotected promoting replication and viral reactivation. The infection of glial cells with JCV depends on the binding of the virus to a receptor complex comprising a carbohydrate receptor and the 5HT2aR and is blocked by antagonists of the 5HT2A receptor as well as by blocking clathrin-dependent receptor-mediated endocytosis.

JCV is present in 80% of population, and the infection is subclinical, but most studies aimed at finding the virus in the CSF have shown that it is never present in the CSF of normal subjects while it is present, although in a reduced number of cases, in subjects with MS (Alvarez-Lafuente et al., 2007).

It is noteworthy that the average viral load is very low (4-6 copies/ml) and close to the limit of sensitivity of the PCR technique. Therefore, the positivity for JCV in MS patients is most likely underestimated.

NOXs in Oligodendrocytes

Oxidative stress is implicated in many neurological diseases, including Multiple Sclerosis. Together with mitochondria, NOX enzyme play a role in reactive oxygen species (ROS) production in the CNS.

NOX enzymes are membrane NADPH oxidases producing superoxide anions by one electron reduction of oxygen using NAD(P)H as the electron donor (Bedard and Krause, 2007). Regulated production of reactive oxygen species (ROS) by NADPH oxidase was first discovered in phagocytic cells. Phagocytic NADPH oxidase is a multicomponent complex comprising two integral membrane proteins, the catalytic subunit gp91phox (CY24B_HUMAN Cytochrome b-245 heavy chain, now referred to as NOX2) and p22phox, and the cytosolic components p47phox, p67phox, p40phox and the small GTPases Rac1 or 2. Upon stimulation, cytosolic subunits translocate to the membrane, activating the enzyme (Babior et al., 2002).

More recently, other isoforms of the catalytic subunit, other than NOX2, have been discovered and up to now in mammalian, seven different NOX genes (NOX1 to 5 and DUOX1 and 2) have been identified (Lambeth, 2004). Like NOX2, also NOX1, NOX3 and NOX4 are associated with the membrane subunit p22phox, but the mechanisms of activation are different. NOX1 is activated by membrane translocation of the cytosolic subunits NOXO1, NOXA1 and Rac 1or 2, while NOX3 requires NOXO1 but the role of the other cytosolic subunits is still uncertain. NOX4, NOX5, DUOX 1 and DUOX 2 activity is not modulated by cytosolic subunits (Bedard and Krause, 2007). NOX4 is constitutively active. NOX5, DUOX1 and DUOX2 are modulated by calcium that interacts with EF-hand binding domains (a helix-loop-helix structural motif found in a large family of calcium-binding proteins) at the N-terminus of the proteins.

Many membrane receptors relay on NOX-dependent ROS production for downstream signaling. As examples, NOX enzymes are activated by growth factor receptors such as platelet-derived growth factor receptor (Svegliati et al., 2005, Baroni et al., 2006; Gabrielli et al.; 2008, Damiano et al.; 2012), epidermal growth factor receptor (Damiano et al., 2015), cholinergic receptors (Serù et al., 2004) and many others (Petry et al., 2010). Also 5HT activates downstream signaling through NOX2—produced ROS (Regmi et al., 2014; Fang et al., 2013; Kruk et al., 2013).

NOX enzymes are widely expressed in central nervous system cells, including oligodendrocytes (Sorce and Krause, 2009); in particular, NOX2 is involved in NMDA receptors signal transduction in these cells (Cavaliere et al., 2013).

In current practice, diagnosing, managing and treatment of Multiple Sclerosis is challenging, there are no definitive tests, symptoms vary widely across individuals and within patients over time, and measurement of disease progression is problematic. Differential diagnosis often entails extensive clinical observation and a battery of costly tests like MRIs. Poor insight into disease progression and therapeutic response creates uncertainty in designing and implementing therapeutic strategies.

Based on the above there is still the need for improved diagnostic and therapies for MS.

SUMMARY OF THE INVENTION

The present invention is based on the finding that autoantibodies responsible for Multiple Sclerosis bind to either one or both membrane proteins, 5-HT2A receptor (5HT2aR or 5HT2AR) and NOXs and their respective epitopes.

Following the observation by immunoprecipitation and flow cytometric analysis, that 5-HT2AR and NOXs are expressed in the cellular model MO3-13 and that NOX3 interacts with 5HT2aR, the inventors found that sera from MS patients selectively bind 5HT2aR and NOX3.

In order to find out the 5HT2aR and NOX3 epitopes responsible for the specific binding of sera from MS patients, the extracellular domains of the proteins have been used for the design of two peptide libraries. Testing these two libraries with the sera from control patients and MS patients, 47 peptides from 5-HT2AR library and 99 peptides from NOX2 library were found to be significantly recognized by MS sera compared to control sera.

To further investigate the possibility of using these peptides for the diagnosis of MS, the inventors tested as an example two peptides: (DDSKVFKEGS (SEQ ID NO: 157)), named "DDSK")) and the other one LYGYRWPLPSKL (SEQ ID NO: 158) named "LYGY")) from the 5-HT2A receptor library using indirect ELISA. Both peptides significantly bind MS IgGs.

Experiments were also performed to evaluate the multiple sclerosis therapeutic use of peptides with sequences comprised within the extracellular domains of 5Ht2a receptor and recognized by the autoantibodies present in MS patients. For example, inventors used the DDSK peptide.

The effects of IgGMS on different signaling molecule downstream the 5Ht2a receptor were evaluated. Incubation of MO3-13 cells with IgGMS increases the levels of ROS, DUOX1/2, P-ERK1/2, NOX3 and HaRas compared to samples treated with control IgG; moreover, the 5Ht receptor antagonist, risperidone, prevents the increase of P-ERK1/2 levels in cells treated with IgGMS. These data demonstrate that IgG from MS patients interfere with 5HT2aR signaling and this effect may have a role in the pathogenesis of the disease. It was also demonstrated that the preincubation of the cells with DDSK peptide reverted the effects of the immunoglobulins from MS patients on signaling molecules downstream 5Ht2A receptor and therefore that it can be used for MS therapy.

Then the peptides comprised in the identified epitopes or comprising the identified epitopes can be used both for the diagnosis and therapy of multiple sclerosis.

In a first aspect therefore the invention provides a peptide or a fragment thereof, said peptide being able to bind multiple sclerosis auto-antibodies and being selected from the group consisting of:
a) a peptide comprising an amino acid sequence having at least 50% identity with any of SEQ ID NO: 16, 37, 33, 25, 47, 57, 55, 46, 56 and comprising the amino acid sequence VFKEG (residues 7-11 of SEQ ID NO: 8) and/or
b) a peptide comprising an amino acid sequence having at least 50% identity with any of SEQ ID NO: 12, 50, 17, 49, 44, 38, 21, 29, 14, 41, 45, 52, 23 and comprising the amino acid sequence YRWP (residues 7-10 of SEQ ID NO: 7) and/or
c) a peptide comprising an amino acid sequence having at least 50% identity with any of SEQ ID NO: 16, 38, 57, 21, 29, 51, 53 and comprising the amino acid sequence KES or NEDVIGAL (residues 8-15 of SEQ ID NO: 9) and/or
d) a peptide comprising an amino acid sequence having at least 50% identity with any of SEQ ID NO: 40, 15, 43, 10, 24, 28, and comprising the amino acid sequence MQLN (residues 19-22 of SEQ ID NO: 2) or TRL and/or
e) a peptide comprising an amino acid sequence having at least 50% identity with any of SEQ ID NO: 19, 54, 20, 22, 26, 27, 11, 13, 35, 48, 16, 37, 18, 33, 31, 39, 30 and comprising the amino acid sequence MDIL (residues 1-4 of SEQ ID NO: 6) or EENTSLSS (residues 6-13 of SEQ ID NO: 6) and/or
f) a peptide comprising an amino acid sequence having at least 50% identity with any of SEQ ID NO: 32, 34, 36 and comprising the amino acid sequence TVD-SENRTNL (residues 2-11 of SEQ ID NO: 22) and/or
g) a peptide comprising an amino acid sequence having at least 50% identity with any of SEQ ID NO: 58, 59, 60, 61, 62, 63, 64, 65, 66, 67, 68, 69, 70, 71, 74, 75, 76, 77, 80, 81, 82, 85, 86, 89, 95, 99, 100, 103, 104, 106, 110, 112, 117, 125, 126, 127, 129, 136, 137, 144, 145 and comprising the amino acid sequence LNFARK (residues 153-158 of SEQ ID NO: 1) or LNFAR (residues 153-157 of SEQ ID NO: 1) or ARK or NESY (residues 26-29 of SEQ ID NO: 4) and/or
h) a peptide comprising an amino acid sequence having at least 50% identity with any of SEQ ID NO: 83, 84, 93, 96, 98, 99, 101, 105, 108, 112, 115, 122, 123, 124, 128, 130, 134, 139, 141, 142, 143, 144, 146, 147, 149, 151, 152, 154, 155, 156 and comprising the amino acid sequence QKISEWG (residues 25-31 of SEQ ID NO: 5) or KISEWG (residues 26-31 of SEQ ID NO: 5) or QKIS (residues 25-28 of SEQ ID NO: 5) and/or
i) a peptide comprising an amino acid sequence having at least 50% identity with any of SEQ ID NO: 72, 78, 118, 121, 132, and comprising the amino acid sequence PYSVAL (residues 136-141 of SEQ ID NO: 1), PYSV (residues 136-139 of SEQ ID NO: 1) or VAL and/or
j) a peptide comprising an amino acid sequence having at least 50% identity with any of SEQ ID NO: 102, 116, and comprising the amino acid sequence KIKECP (residues 2-7 of SEQ ID NO: 102).

Preferably the peptide comprises an amino acid sequence having at least 60% identity with any of SEQ ID NO: 10 to 156, preferably at least 70% identity with any of SEQ ID NO: 10 to 156, preferably at least 80%, 85% identity with any of SEQ ID NO: 10 to 156, still preferably at least 90% identity with any of SEQ ID NO: 10 to 156, preferably at least 95% with any of SEQ ID NO: 10 to 156, preferably at least 99% with any of SEQ ID NO: 10 to 156.

Preferably the peptide has at least 60% identity with any of DDSKVFKEGS (SEQ ID NO: 157) or LYGYRWPLPSKL (SEQ ID NO: 158), preferably at least 70%, 75%, 80%, 85%, 90% or 95% identity with any of DDSKVFKEGS (SEQ ID NO: 157) or LYGYRWPLPSKL (SEQ ID NO: 158)

In a preferred embodiment the peptide essentially consists of any of SEQ ID NO: 10 to 156.

In a preferred embodiment the peptide essentially consists of DDSKVFKEGS (SEQ ID NO: 157) or LYGYRWPLPSKL (SEQ ID NO: 158).

In a preferred embodiment the peptide of the invention comprises at least one an amino acid sequence as described in Table 1 or Table 2 or a fragment thereof. In particular the fragments of the protein may be the sequence between two cysteine residues.

In a preferred embodiment the peptide of the invention essentially consists of an amino acid sequence as described in Table 1 or Table 2 or a fragment thereof.

In double looped peptides, three cysteine residues were added, two as first and last amino acid and one in the middle of the sequence. Then peptides of the invention may the whole sequence or the fragments located between two cysteine residues or the sequence with only one cysteine at either end of the sequence. For instance for peptide 1 of table 1, peptides of interest are CNSLMQLNDDTRLYC MDILSEENTSLSSC (SEQ ID NO: 10) or NSLMQLNDDTRLY (aa 2-14 of SEQ ID NO: 10) or MDILSEENTSLSS (aa 16-28 of SEQ ID NO: 10) or CNSLMQLNDDTRLY (aa 1-14 of SEQ ID NO: 10) or NSLMQLNDDTRLYC (aa 2-15 of SEQ ID NO: 10) or CMDILSEENTSLSS (aa 15-28 of SEQ ID NO: 10) or MDILSEENTSLSSC (aa 16-29 of SEQ ID NO: 10).

Preferably the peptide is in linear or conformational form.

Preferably the peptide is for medical use. Preferably for use in the treatment and/or prevention of multiple sclerosis.

The invention further provides a pharmaceutical composition comprising at least one peptide as defined above and pharmaceutically acceptable excipients, preferably for use in the treatment and/or prevention of multiple sclerosis.

Preferably the composition further comprises a therapeutic agent, preferably the therapeutic agent is selected from the group consisting of: b-interferon, cognitive enhancers (nootropics): methylphenidate, racetams, isoflavones, vitamins (B, C, D, E), choline, amphetamines, xanthines, adrenergics, cholinergics, serotonigergic, dopaminergics, eugeroics (adrafinil, armodafinil, modafinil), GABA blockers, AMPAkines, PDE4 inhibitors and others; neuroprotective agents: glutamate antagonists, 17β-Estradiol, ginsenoside Rd, progesterone, statins, antioxidants, nicotine, caffeine, caspase inhibitors, neurotrophic factors, other antiapoptotic agents; anti-pain medication or natalizumab.

The invention also provides the use of at least one peptide as defined above for detecting multiple sclerosis auto-antibodies in a biological fluid isolated from a subject.

The invention also provides a method for the diagnosis or for monitoring the progression of multiple sclerosis or for identifying or monitoring a therapy for multiple sclerosis characterized in detecting multiple sclerosis auto-antibodies in a biological sample isolated from a subject by means of binding to at least one peptide as defined above.

The invention provides a kit for the diagnosis or for monitoring the progression of multiple sclerosis or for identifying or monitoring a therapy for multiple sclerosis comprising at least one peptide as defined above.

The invention provides a nucleic acid molecule encoding for any one of the peptide or fragment thereof as defined herein.

The invention provides an antibody or a recombinant or synthetic derivative thereof able to recognize and bind to at least one peptide as defined herein, preferably for medical and/or diagnostic use, preferably for use in the treatment and/or prevention or diagnosis and/or for monitoring the progression of multiple sclerosis and/or for identifying or monitoring a therapy of multiple sclerosis.

The peptides of the invention are comprised in loop 1 (SEQ ID NO: 7), in loop 2 (SEQ ID NO: 8), in loop 3 (SEQ ID NO: 9) or in the N-terminal region of the 5HT2aR (SEQ ID NO: 6) or in loop 2 (SEQ ID NO: 4) or in loop 3 (SEQ ID NO: 5) of NOX2. However the peptides may also comprise loop 1 (SEQ ID NO: 7), loop 2 (SEQ ID NO: 8), loop 3 (SEQ ID NO: 9) or N-terminal region of the 5HT2aR (SEQ ID NO: 6) or loop 2 (SEQ ID NO: 4) or loop 3 (SEQ ID NO: 5) of NOX2.

The peptide of the invention is a peptide comprising an amino acid sequence having at least 50% identity, preferably at least 60%, preferably at least 70%, preferably at least 80%, preferably at least 85%, 87%, 90%, 92%, 95%, 99% with SEQ ID NO. 4 and/or SEQ ID NO. 5 and/or SEQ ID NO. 6 and/or SEQ ID NO. 7 and/or SEQ ID NO. 8 and/or SEQ ID NO. 9 or having at least 50%, preferably at least 60%, preferably at least 70%, preferably at least 80%, preferably at least 85%, 87%, 90%, 92%, 95%, 99% identity with a fragment of SEQ ID NO.4/or SEQ ID NO. 5 and/or SEQ ID NO. 6 and/or SEQ ID NO. 7 and/or SEQ ID NO. 8 and/or SEQ ID NO. 9 or a fragment of said peptide.

The peptide of the invention or a fragment thereof is an epitope for multiple sclerosis auto-antibodies.

Percentage identity is determined by means of know method in the art such as BLAST using available algorithms.

In the present invention a fragment of the peptide of the inventor is an epitope for multiple sclerosis auto-antibodies.

In particular the fragment has at least 3 amino acids (aa), preferably at least 4, 5, 6, 7 aa, 9 aa, 10 aa, 15 aa, 20 aa, 25 aa, 28 aa, 29 aa or 30 aa.

The fragment of the peptide is a functional fragment that binds multiple sclerosis auto-antibodies.

An epitope is defined as the part of the antigen that is recognized by antibodies. The epitope is the specific piece of the antigen that an antibody binds to. The part of an antibody that binds to the epitope is called a paratope. Although epitopes are usually non-self proteins, sequences derived from the host that can be recognized (as in the case of autoimmune diseases) are also epitopes.

The epitopes of protein antigens are divided into two categories, conformational epitopes and linear epitopes, based on their structure and interaction with the paratope. A conformational epitope is composed of discontinuous sections of the antigen's amino acid sequence. These epitopes interact with the paratope based on the 3-D surface features and shape or tertiary structure of the antigen.

An epitope for multiple sclerosis auto-antibodies is defined as the antigen recognized by the autoantibodies. This is part of endogenous proteins expressed by cells.

An autoantibody is an antibody directed against one or more of the individual's own proteins.

The peptide or a fragment thereof binds to multiple sclerosis biological fluid. The biological fluid may be blood, serum, plasma, saliva, urine, cerebrospinal fluid, lymph fluid, pleural fluid or synovial fluid.

The peptide of the invention or fragment thereof bind IgG of MS patients with an affinity of 1 microM to 1 PicoM.

Binding of the peptide of the invention to MS biological fluid or to MS IgG may be performed by any known method in the art.

The peptide of the invention may also be chimeric peptide comprising a combination of peptides relative to 5HT2aR (Table 1) and peptides relative to NOX 2 (Table 2). Preferably the chimeric peptide is an hybrid between peptides relative to 5HT2aR (Table 1) and peptides relative to NOX 2 (Table 2). Preferably the chimeric peptide comprise several peptides relative to 5HT2aR (Table 1) or several peptides relative to NOX 2 (Table 2).

The peptide of the invention, if required, can be modified in vitro and/or in vivo, for example by glycosylation, myristoylation, amidation, carboxylation or phosphorylation, and may be obtained, for example, by synthetic or recombinant techniques known in the art.

The peptide of the invention may also be modified to better adhere to a solid support (as in the kit of the invention). Such modifications include biotylination, avidin conjugation, polymer conjugation, ect.

As used herein, the term "derivatives" refers to longer or shorter peptides having a percentage of identity of at least 45%, preferably at least 50%, 60%, 65%, 70% or 75% with SEQ ID NO. 4, 5, 6, 7, 8 or 9, or ortholog thereof, preferably of at least 85%, as an example of at least 90%, and more preferably of at least 95%.

As used herein "fragments" refers to peptides having a length of at least 3, preferably at least 4, 5, 10 amino acids, preferably at least 15 or at least 20 amino acids, more preferably at least 25 amino acids, and more preferably of at least 50 amino acids. The fragments maintain the biological activity of the peptide of the invention, i.e binding to MS biological sample. As used herein, "percentage of identity" between two amino acids sequences, means the percentage of identical amino-acids, between the two sequences to be compared, obtained with the best alignment of said sequences, this percentage being purely statistical and the differences between these two sequences being randomly spread over the amino acids sequences. As used herein, "best alignment" or "optimal alignment", means the alignment for which the determined percentage of identity (see below) is the highest. Sequences comparison between two amino acids sequences are usually realized by comparing these sequences that have been previously aligned according to the best alignment; this comparison is realized on segments of comparison in order to identify and compared the local regions of similarity. The best sequences alignment to perform comparison can be realized, beside by a manual way, by using the global homology algorithm developed by SMITH and WATERMAN (Ad. App. Math., vol. 2, p:482, 1981), by using the local homology algorithm developed by NEDDLEMAN and WUNSCH (J. Mol. Biol, vol. 48, p:443, 1970), by using the method of similarities developed by PEARSON and LIPMAN (Proc. Natl. Acd. Sci. USA, vol. 85, p:2444, 1988), by using computer softwares using such algorithms (GAP, BESTFIT, BLAST P, BLAST N, FASTA, TFASTA in the Wisconsin Genetics software Package, Genetics Computer Group, 575 Science Dr., Madison, Wis. USA), by using the MUSCLE multiple alignment algorithms (Edgar, Robert C, Nucleic Acids Research, vol. 32, p:1792, 2004). To get the best local alignment, one can preferably used BLAST software, with the BLOSUM 62 matrix, or the PAM 30 matrix. The identity percentage between two sequences of amino acids is determined by comparing these two sequences optimally aligned, the amino acid sequences being able to comprise additions or deletions in respect to the reference sequence in order to get the optimal alignment between these two sequences. The percentage of identity is calculated by determining the number of identical position between these two sequences, and dividing this number by the total number of compared positions, and by multiplying the result obtained by 100 to get the percentage of identity between these two sequences.

Within the meaning of the present invention, the terms "peptide" or "polypeptide" are not particularly restricted, and in general designate natural or synthetic peptides containing only natural amino acids, only non-natural amino acids, or combinations of natural and non-natural amino acids. In the context of the present invention, the term "peptide" denotes a chain of amino acids linked together via a peptide bond (or amide bond). The term "amino acid" as employed herein includes and encompasses all of the naturally occurring amino acids, either in the D-, L-, allo, or other stereoisomeric configurations if optically active, as well as any known or conceivable non-natural, synthetic and modified amino acid.

The term "natural amino acids" denotes the following 20 amino acids in their laevorotatory (L) or dextrorotatory (D) form, preferably in their natural L form:

| Name | One-letter code | Three-letter code |
| --- | --- | --- |
| Alanie | A | Ala |
| Arginine | R | Arg |
| Asparagine | N | Asn |
| Aspartate | D | Asp |
| Cysteine | C | Cys |
| Glutamate | E | Glu |
| Glutamine | Q | Gln |
| Glycine | G | Gly |
| Histidine | H | His |
| Isoleucine | I | Ile |
| Leucine | L | Leu |
| Lysine | K | Lys |
| Metnionine | M | Met |
| Phenylalanine | F | Phe |
| Proline | P | Pro |
| Serine | S | Ser |
| Threonine | T | Thr |
| Tryptophan | W | Trp |
| Tyrosine | Y | Tyr |
| Valine | V | Val |

The term "hydrophobic amino acid" denotes one of the following amino acids: I, L, V, M, F, Y, W, T, G, C or A. The term "alkaline hydrophilic amino acid" denotes one of the following amino acids: R, K or H. The term "neutral hydrophilic amino acid" denotes one of the following amino acids: S, P, N or Q. The term "acidic amino acid" denotes one of the following amino acids: D or E. In particular, the term "polypeptides" as employed herein includes and encompasses oligopeptides, peptides, polypeptides and derivatives thereof, peptide analogs and derivatives thereof, as well as pharmaceutically acceptable salts of said peptides. The term "peptides" as employed herein includes complexes with other species, such as metal ions (like copper, zinc, manganese, magnesium etc.).

The terms "hexapeptide", "pentapeptide", "tetrapeptide" indicate compounds including a sequence of, respectively, six, five and four amino acids in consecutive order. These amino acids are indicated using the three or one letter codes, according to international conventions, from the N-terminus to the C-terminus. According to said conventions, proline is indicated as Pro or P, histidine is indicated as His or H, arginine as Arg or R, glutamic acis as Glu or E, asparagine as Asn or N, lysine as Lys or K, glutamine as Gln or Q, aspartic acid as Asp or D.

The abbreviations used for the amino acids follow the rules of the Commission on Biochemical Nomenclature IUPAC-IUB specified in Eur. J. Biochem. (1984) 138, 9-37 and in J. Biol. Chem. (1989) 264, 633-673.

According to specific embodiments of the invention, the non natural amino acids include, without limitations, the hydroxyproline (Hyp), the L-1,2,3,4-tetrahydroisoquinolin-3-carboxylic acid (Tic), azetidine, D-proline (pro), homo-proline (hPro), thienylalanine (Tha), tiazolidinalanine (Thz), ornitine (Orn), nor-arginine (Agb).

To increase the bioavailability and the capacity of the peptides of the invention to cross the blood brain barriers, their lipophilicity or lipophilic character can be increased through acylation of the N-terminal amino group of the peptide, or through esterification of the carboxy terminal with an alcohol, linear or branched, saturated or unsaturated, hydroxylated or not, or through both said chemical modifications.

In a preferred embodiment, N-acyl groups are acetyl, lauroyl, miristoyl, palmitoyl, steroyl, oleoyl, lineoyl. Particularly preferred are the groups N-acetyl and N-palmitoyl.

When used at the N-terminal of a sequence, "Ac" indicates an N-acyl derivative (indicated also as acyl-derivative). Similarly, "Palm" indicates a N-Palmitoyl derivative. When used at the C-terminus of a sequence, "OAlk" indicates an ester group attached to the C-terminus carboxylic group.

The polypeptides of the invention can be obtained from chemical or enzymatic synthesis starting from the constitutive amino acids or from their derivatives; alternatively, they can be obtained from natural proteins by hydrolysis under mild conditions, or by biotechnology. For example, known methods of peptide synthesis can be applied, as the Fmoc/tBu method in solid phase. Other chemical methods include Boc/bzl or liquid phase synthesis. References for the synthetic methodologies are described for example in: Solid Phase Peptide Synthesis (1984), Pierce Chemical Company, Rockford, Ill.; The Practice of Peptide Synthesis (1984), Springer Verlach, N.Y.; Chemical Approaches to the Synthesis of Peptides and Proteins (1997), CRC, Boca Raton, Fla.; J. Biol. Chem. (1980), 255, 8234-8238.

The polypeptides of the invention can form homogeneous or mixed salts with mono- or polivalent acids, preferably with inorganic acids or with appropriate aliphatic carboxylic acids saturated or unsaturated, or with aromatic carboxylic acids, or with aliphatic or aromatic solfonic acids, preferably acetic acid, lactic acid and/or chloridric acid.

The term "polynucleotide" according to the present invention refers to a single strand nucleotide chain or its complementary strand which can be of the DNA or RNA type, or a double strand nucleotide chain which can be of the cDNA (complementary) or genomic DNA type.

Preferably, the polynucleotides of the invention are of the DNA type, namely double strand DNA. The term "polynucleotide" also refers to modified polynucleotides.

The polynucleotides of this invention are isolated or purified from their natural environment.

Preferably, the polynucleotides of this invention can be prepared using conventional molecular biology techniques such as those described by Sambrook et al. (Molecular Cloning: A Laboratory Manual, 1989) or by chemical synthesis.

The polynucleotide of the invention may also include the coding sequence of the polypeptide defined previously, additional coding sequence such as leader sequence or a proprotein sequence, and/or additional non-coding sequence, such as introns or 540 and/or 3' UTR sequences.

As used herein, the term "vector" refers to an expression vector, and may be for example in the form of a plasmid, a viral particle, a phage, etc. Such vectors may include bacterial plasmids, phage DNA, baculovirus, yeast plasmids, vectors derived from combinations of plasmids and phage DNA, viral DNA such as vaccinia, adenovirus, fowl pox virus, adenovirus, adeno-associated virus and pseudorabies. Large numbers of suitable vectors are known to those of skill in the art and are commercially available. The following vectors are provided by way of example. Bacterial: pQE70, pQE60, pQE-9 (QIAGEN), pbs, pDIO, phagescript, psiX174, pbluescript SK, pbsks, pNH8A, pNHI[beta]a, pNH18A, pNH46A (STRATAGENE), ptrc99a, pKK223-3, pKK233-3, pDR540, pRIT5 (PHARMACIA). Eukaryotic: pWLNEO, pSV2CAT, pOG44, pXTI, pSG (STRATAGENE), pSVK3, pBPV, pMSG, pSVL (PHARMACIA). However, any other vector may be used as long as it is replicable and viable in the host. The polynucleotide sequence, preferably the DNA sequence in the vector is operatively linked to an appropriate expression control sequence(s) (promoter) to direct mRNA synthesis. As representative examples of such promoters, one can mentioned prokaryotic or eukaryotic promoters such as CMV immediate early, HSV thymidine kinase, early and late SV40, LTRs from retrovirus, and mouse metallothionein-I. The expression vector also contains a ribosome binding site for translation initiation and a transcription vector. The vector may also include appropriate sequences for amplifying expression.

In addition, the vectors preferably contain one or more selectable marker genes to provide a phenotypic trait for selection of transformed host cells such as dihydro folate reductase or neomycin resistance for eukaryotic cell culture, or such as tetracycline or ampicillin resistance in *E. coli*.

As used herein, the term "host cell genetically engineered" or "host cell" relates to host cells which have been transduced, transformed or transfected with the polynucleotide or with the vector described previously.

As representative examples of appropriate host cells, one can cites bacterial cells, such as *E. coli, Streptomyces, Salmonella typhimurium*, fungal cells such as yeast, insect cells such as Sf9, animal cells such as CHO or COS, plant cells, etc. The selection of an appropriate host is deemed to be within the scope of those skilled in the art from the teachings herein.

Preferably, said host cell is an animal cell, and most preferably a human cell. The introduction of the polynucleotide or of the vector described previously into the host cell can be effected by method well known from one of skill in the art such as calcium phosphate transfection, DEAE-Dextran mediated transfection, or electroporation.

The polynucleotide may be a vector such as for example a viral vector.

Another object of the invention is a composition comprising a transformed host cell expressing a peptide of the invention.

The man skilled in the art is well aware of the standard methods for incorporation of a polynucleotide into a host cell, for example transfection, lipofection, electroporation, microinjection, viral infection, thermal shock, transformation after chemical permeabilisation of the membrane or cell fusion.

The term "antibody" is used herein in the broadest sense and specifically covers monoclonal antibodies of any isotype such as IgG, IgM, IgA, IgD and IgE, polyclonal antibodies, chimeric antibodies, humanized antibodies and antibody fragments. An antibody reactive with a specific antigen can be generated by recombinant methods such as selection of libraries of recombinant antibodies in phage or similar vectors, or by immunizing an animal with the antigen or an antigen-encoding nucleic acid. A typical IgG antibody is comprised of two identical heavy chains and two identical light chains that are joined by disulfide bonds. Each heavy and light chain contains a constant region and a variable region. Each variable region contains three segments called "complementarity-determining regions" ("CDRs") or "hypervariable regions", which are primarily responsible for binding an epitope of an antigen. They are usually referred to as CDRI, CDR2, and CDR3, numbered sequentially from the N-terminus. The more highly conserved portions of the variable regions are called the "framework regions". As used herein, "VH" or "VH" refers to the variable region of an immunoglobulin heavy chain of an antibody, including the heavy chain of an Fv, scFv, dsFv, Fab, Fab' or F(ab')2 fragment. Reference to "VL" or "VL" refers to the variable region of the immunoglobulin light chain of an antibody, including the light chain of an Fv, scFv, dsFv, Fab, Fab' or F(ab')2 fragment. A "polyclonal antibody" is an antibody which was produced among or in the presence of one or more other, non-identical antibodies. In general, polyclonal antibodies are produced from a B-lymphocyte in the presence of several other B-lymphocytes producing non-identical antibodies. Usually, polyclonal antibodies are obtained directly from an immunized animal. A "monoclonal antibody", as used herein, is an antibody obtained from a population of substantially homogeneous antibodies, i.e. the antibodies forming this population are essentially identical except for possible naturally occurring mutations which might be present in minor amounts. These antibodies are directed against a single epitope and are therefore highly specific. An "epitope" is the site on the antigen to which an antibody binds.

As used herein, a "chimeric antibody" is an antibody in which the constant region, or a portion thereof, is altered, replaced, or exchanged, so that the variable region is linked to a constant region of a different species, or belonging to another antibody class or subclass.

"Chimeric antibody" also refers to an antibody in which the variable region, or a portion thereof, is altered, replaced, or exchanged, so that the constant region is linked to a variable region of a different species, or belonging to another antibody class or subclass. Methods for producing chimeric antibodies are known in the art.

The term "humanized antibody", as used herein, refers to a chimeric antibody which contain minimal sequence derived from non-human immunoglobulin. The goal of humanization is a reduction in the immunogenicity of a xenogenic antibody, such as a murine antibody, for introduction into a human, while maintaining the full antigen binding affinity and specificity of the antibody. Humanized antibodies, or antibodies adapted for non-rejection by other mammals, may be produced using several technologies such as resurfacing and CDR grafting. Humanized chimeric antibodies preferably have constant regions and variable regions other than the complementarity determining regions derived substantially or exclusively from the corresponding human antibody regions and CDRs derived substantially or exclusively from a mammal other than a human. The antibodies of the present invention include both the full length antibodies discussed above, as well as epitope-binding fragments thereof. As used herein, "antibody fragments" include any portion of an antibody that retains the ability to bind to the epitope recognized by the full length antibody, generally termed "epitope-binding fragments." Examples of antibody fragments include, but are not limited to, Fab, Fab' and F(ab')2, Fd, single-chain Fvs (scFv), single-chain antibodies, disulfide-linked Fvs (dsFv) and fragments comprising either a VL or VH region. Epitope-binding fragments, including single-chain antibodies, may comprise the variable region(s) alone or in combination with the entirety or a portion of the following: hinge region, CH1, CH2, and CH3 domains.

The peptides of the invention find use as active ingredients for the preparation of compositions or pharmaceutical formulations preferably for medical use in MS. Said compositions can be used for example to prevent or reduce signs of MS.

The present invention provides peptides and compositions for various way of application which comprise an effective amount of a peptide of the invention to treat, reverse, ameliorate and/or prevent signs of MS.

For the purposes of the present invention, the term derivative denotes any molecule obtained by modification, of a genetic and/or chemical nature, of these sequences and which retains the desired activity. Modification of a genetic and/or chemical nature should be understood to mean any mutation, substitution, deletion, addition and/or modification of one or more residues. Such derivatives may be generated for different purposes, such as, in particular, that of increasing the affinity of the peptide for its interaction site, that of improving its levels of production, that of increasing its resistance to proteases, that of increasing its therapeutic efficacy or of reducing its side effects, that of endowing it with novel pharmacokinetic and/or biological properties, that increasing circulatory half-life in the body of the patient, that of enhancing bioavailability and/or enhancing efficacy and/or specificity. In addition, non-peptide peptidomimetics for improving stability, for example less susceptible to biological degradation must also be included as well as the synthesis of the said peptide sequences using D-amino acids instead of the natural L-amino acids, which may increase stability and resistance to degradation.

Allelic variants, refer to variants of peptides in the same species, orthologous of peptides of the invention refer to variants in different species.

The peptide or composition of the invention may also be in the form of a food supplement. The molecule or pharmaceutical composition of the invention is preferably administered directly into the brain.

In the present invention vector is for therapy, in particular by gene therapy comprising under the control of suitable regulative sequences a nucleotide sequence encoding the peptide or a combination as above discloses, also expressed in stem cells (hematopoietic and/or neuronal).

The phrase "pharmaceutically acceptable" refers to molecular entities and compositions that are physiologically tolerable and do not typically produce an allergic or similar untoward reaction, such as gastric upset, dizziness and the like, when administered to a human.

Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans.

The term "carrier" refers to a diluent, adjuvant, excipient, or vehicle with which the molecule is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The composition of the invention may comprise one or more additives (e.g., stabilizers, preservatives). See, generally, Ullmann's Encyclopedia of Industrial Chemistry, 6th Ed. (various editors, 1989-1998, Marcel Dekker); and Pharmaceutical Dosage Forms and Drug Delivery Systems (ANSEL et al, 1994, WILLIAMS & WILKINS).

Typically, the medicament may be used for the therapeutic or prophylactic treatment of a subject, said subject corresponding to a mammal, in particular to a human being.

According to the present invention, an "effective amount" of a composition is one that is sufficient to achieve a desired biological effect, in this case binding to MS fluid and/or treatment of MS. It is understood that the effective dosage will be dependent upon the age, sex, health, and weight of the recipient, kind of concurrent treatment, if any, frequency of treatment, and the nature of the effect desired. The provided ranges of effective doses of the peptide of the invention (from 0.0001 mg/kg to 100 mg/kg, in particular systemically administered) are not intended to limit the invention and represent preferred dose ranges. However, the preferred dosage can be tailored to the individual subject, as is understood and determinable by one of skill in the art, without undue experimentation. The present invention has use in human and animal health (veterinary use).

An aspect of the present invention comprises a nucleic acid construct comprised within a delivery vehicle. A delivery vehicle is an entity whereby a nucleotide sequence can be transported from at least one media to another. Delivery vehicles may be generally used for expression of the sequences encoded within the nucleic acid construct and/or for the intracellular delivery of the construct. It is within the scope of the present invention that the delivery vehicle may be a vehicle selected from the group of RNA based vehicles, DNA based vehicles/vectors, lipid based vehicles, virally based vehicles and cell based vehicles. Examples of such delivery vehicles include: biodegradable polymer microspheres, lipid based formulations such as liposome carriers, coating the construct onto colloidal gold particles, lipopolysaccharides, polypeptides, polysaccharides, pegylation of viral vehicles.

In one embodiment of the present invention may comprise a virus as a delivery vehicle, where the virus may be selected from: adenoviruses, retroviruses, lentiviruses, adeno-associated viruses, herpesviruses, vaccinia viruses, foamy viruses, cytomegaloviruses, Semliki forest virus, poxviruses, RNA virus vector and DNA virus vector. Such viral vectors are well known in the art.

Commonly used gene transfer techniques include calcium phosphate, DEAE-dextran, transfection, electroporation and microinjection and viral methods. Another technique for the introduction of DNA into cells is the use of cationic liposomes. Commercially available cationic lipid formulations are e.g. Tfx 50 (Promega) or Lipofectamin 2000 (Life Technologies).

The compositions of the present invention may be in form of a solution, e.g. an injectable solution, a cream, ointment, tablet, suspension or the like. The composition may be administered in any suitable way, e.g. by injection, particularly by intraocular injection, by oral, topical, nasal, rectal application etc. The carrier may be any suitable pharmaceutical carrier.

Preferably, a carrier is used, which is capable of increasing the efficacy of the RNA molecules to enter the target-cells. Suitable examples of such carriers are liposomes, particularly cationic liposomes.

The recombinant expression vector of the invention can be any suitable recombinant expression vector, and can be used to transform or transfect any suitable host. Suitable vectors include those designed for propagation and expansion or for expression or both, such as plasmids and viruses. The recombinant expression vectors of the invention can be prepared using standard recombinant DNA techniques. Constructs of expression vectors, which are circular or linear, can be prepared to contain a replication system functional in a prokaryotic or eukaryotic host cell. Replication systems can be derived, e.g., from ColEl, 2 µ plasmid, λ, SV40, bovine papilloma virus, and the like.

Desirably, the recombinant expression vector comprises regulatory sequences, such as transcription and translation initiation and termination codons, which are specific to the type of host (e.g., bacterium, fungus, plant, or animal) into which the vector is to be introduced, as appropriate and taking into consideration whether the vector is DNA- or RNA-based. The recombinant expression vector can include one or more marker genes, which allow for selection of transformed or transfected hosts. Marker genes include biocide resistance, e.g., resistance to antibiotics, heavy metals, etc., complementation in an auxotrophic host to provide prototrophy, and the like. Suitable marker genes for the inventive expression vectors include, for instance, neomycin/G418 resistance genes, hygromycin resistance genes, histidinol resistance genes, tetracycline resistance genes, and ampicillin resistance genes. The recombinant expression vector can comprise a native or normative promoter operably linked to the nucleotide sequence encoding the peptide of the invention (including functional portions and functional variants thereof), or to the nucleotide sequence which is complementary to or which hybridizes to the nucleotide sequence encoding the RNA. The selection of promoters, e.g., strong, weak, inducible, tissue-specific and developmental-specific, is within the ordinary skill of the artisan. Similarly, the combining of a nucleotide sequence with a promoter is also within the skill of the artisan. The promoter can be a non-viral promoter or a viral promoter, e.g., a cytomegalovirus (CMV) promoter, an SV40 promoter, an RSV promoter and a promoter found in the long-terminal repeat of the murine stem cell virus.

The inventive recombinant expression vectors can be designed for either transient expression, for stable expression, or for both. Also, the recombinant expression vectors can be made for constitutive expression or for inducible expression.

When the peptide or antibody of the invention is administered with one or more additional therapeutic agents, one or more additional therapeutic agents can be coadministered to the mammal. By "coadministering" is meant administering one or more additional therapeutic agents and the molecule of the invention sufficiently close in time such that the molecule can enhance the effect of one or more additional therapeutic agents. In this regard, the molecule of the invention can be administered first and the one or more additional therapeutic agents can be administered second, or vice versa. Alternatively, the molecule of the invention and the one or more additional therapeutic agents can be administered simultaneously. The additional therapeutic agent may be a recombinant expression vector comprising a coding sequence providing neuroprotective and/or cognition enhancement under the control of an appropriate promoter.

Additional therapeutic agents may include b-interferon, cognitive enhancers (nootropics): methylphenidate, racetams, isoflavones, vitamins (B, C, D, E), choline, amphetamines, xanthines, adrenergics, cholinergics, serotonigergic, dopaminergics, eugeroics (adrafinil, armodafinil, modafinil), GABA blockers, AMPAkines, PDE4 inhibitors and others; neuroprotective agents: glutamate antagonists, 17β-Estradiol, ginsenoside Rd, progesterone, statins, antioxidants, nicotine, caffeine, caspase inhibitors, neurotrophic factors, other antiapoptotic agents; anti-pain medication or natalizumab.

It is a further object of the invention a kit consisting of separate packs of:

an effective amount of the peptide of the invention or pharmaceutically usable derivatives thereof as defined above and an effective amount of a further medicament active ingredient.

The further medicament active ingredient is selected from b-interferon, cognitive enhancers and/or neuroprotective agents, anti-pain medication as indicated above.

The delivery systems useful in the context of embodiments of the invention may include time-released, delayed release and sustained release delivery systems such that the delivery of the inventive composition occurs prior to, and with sufficient time to cause, sensitization of the site to be treated. The inventive composition can be used in conjunction with other therapeutic agents or therapies. Such systems can avoid repeated administrations of the inventive composition, thereby increasing convenience to the subject and the physician, and may be particularly suitable for certain composition embodiments of the invention. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are lipids including sterols such as cholesterol, cholesterol esters, and fatty acids or neutral fats such as mono-di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the active composition is contained in a form within a matrix such as those described in U.S. Pat. Nos. 4,452,775, 4,667,014, 4,748,034, and 5,239,660 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The kit of the present invention may include written instructions.

In the method for the diagnosis or for monitoring the progression of multiple sclerosis or for identifying or monitoring a therapy for multiple sclerosis of the present invention, the quantity of multiple sclerosis auto-antibodies may also be quantified and compared to a reference control. The reference control may be the quantity of multiple sclerosis auto-antibodies in a patient affected by a neurological disorder other than MS, the quantity of multiple sclerosis auto-antibodies in a MS patient before start of the therapy or the quantity of multiple sclerosis auto-antibodies in a MS patient at different time points during the therapy.

The present invention will be illustrated by means of non-limiting examples in reference to the following figures.

Figure 1C:
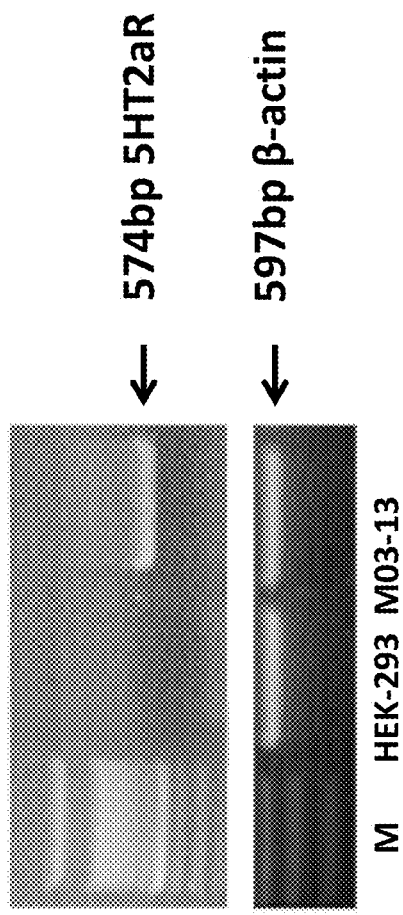

FIGS. 1A, 1B and 1C: 5-HTA2R expression in MO3-13 cells (A) Immunoreactivity for 5HT2aR in MO3-13 cells was evidenced by indirect immunofluorescence and flow cytometric analysis using primary antibodies against human 5HT2aR and Cy3-conjugated anti-rabbit IgG as secondary antibodies. Control was treated with secondary antibodies alone. (B) Western blotting analysis of 5HT2aR in three different cell lines. To determine which band is specific for 5HT2aR, an immunizing peptide blocking experiment has been performed as follow: before proceeding with the staining protocol, the antibody was incubated with an excess (two fold) of peptide (immunizing peptide) that corresponds to the epitope recognized by the antibody. By comparing the staining from the blocking antibody (right panel) with that of antibody alone (left panel) it is possible to evidence the specific bands. As evidenced by the circle, in MO3-13 cells the 5HT2aR appears as a double band one of 20 and one of 30 kD. (C) PCR analysis of 5Ht2a receptor in MO3-13 and HEK-293 cells. Total mRNA was extracted with Trizol, reverse transcribed and analyzed by PCR with specific primers to human 5HT2aR or β-actin fragment, as internal control. The PCR analysis was carried out at 35 number of cycles. M, Molecular Weight Marker.

Figure 2:
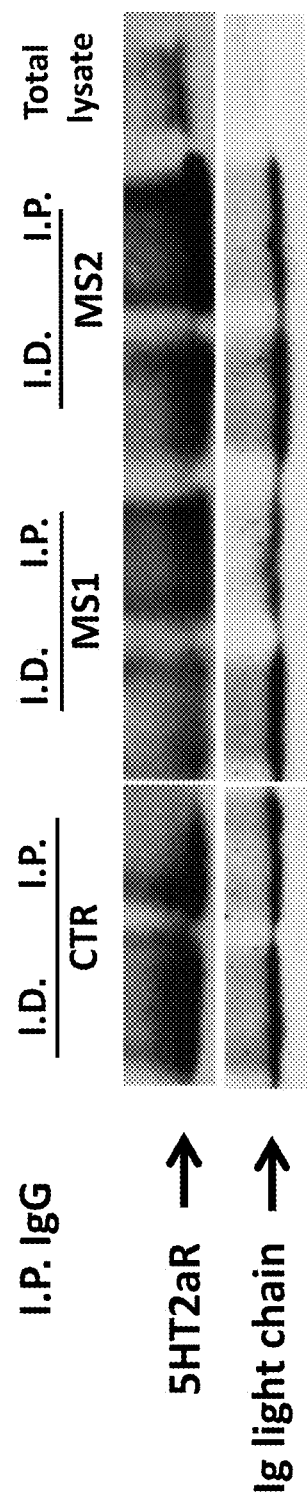

FIG. 2: IgG from MS patients bind to 5Ht2a receptor in MO3-13 cells. MO3-13 cells were incubated for 18 h in medium containing 0.2% FBS before harvesting them for immunoprecipitation with IgG from 1 neurological (other neurological disorders affected patients, CTR) and 2 MS patients (MS1 and MS2) and immunoblot with anti-human 5Ht2a receptor antibody. I.D. indicate the immunodepleted and I.P. the immunoprecipitated samples.

Figure 3:
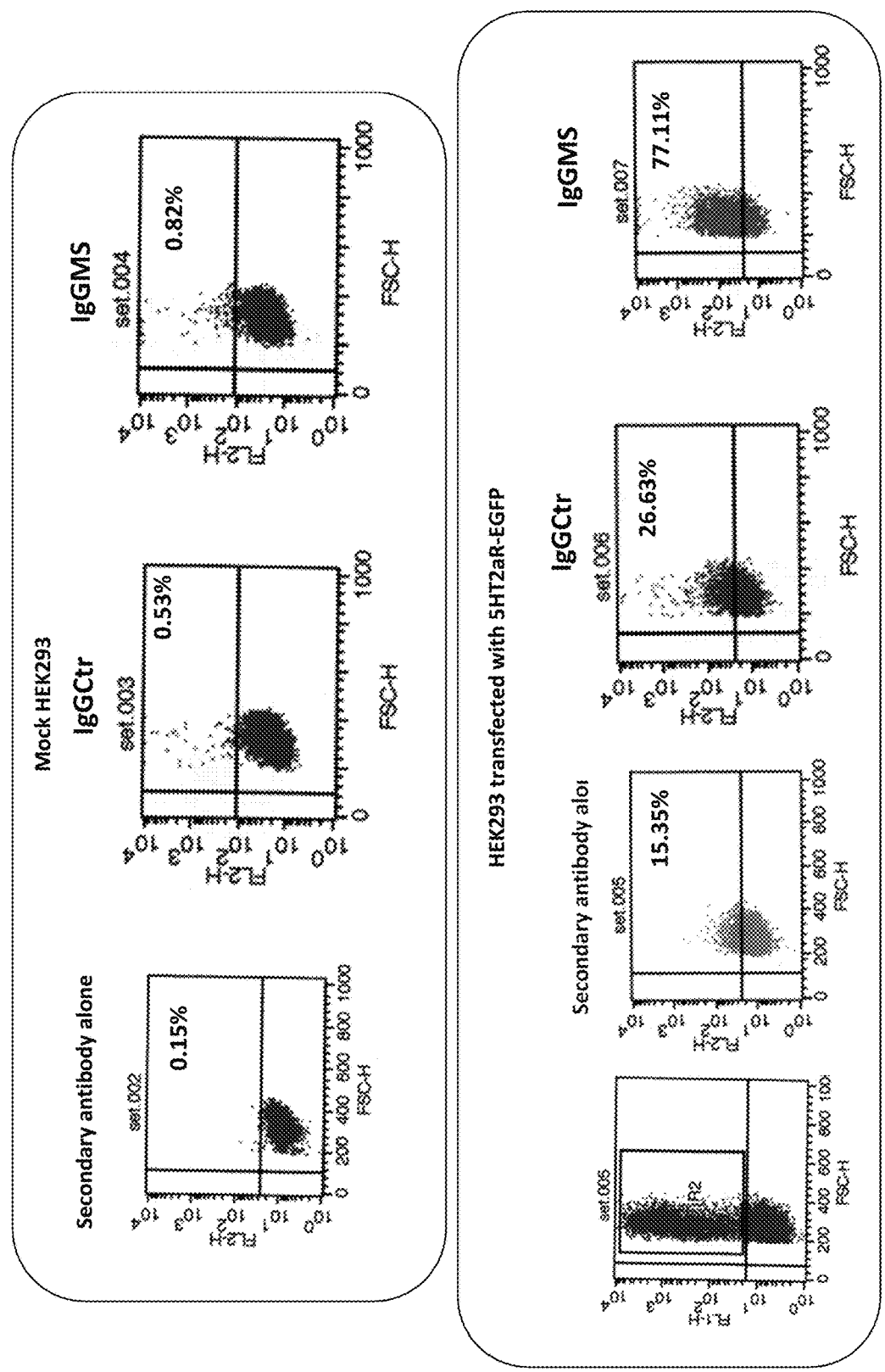

FIG. 3: Binding between serum IgG from neurological or MS patients and 5-HT2a receptor. HEK-293 cells transfected with 5-HT2aR-EGFP construct (lower panel) were resuspended in 200 μl PBS and then incubated with mouse serum for 30 min at 4° C., to block non specific binding. Then cells were incubated for 30 min with 200 μg of serum IgG from MS (IgGMS) or neurological (other neurological disorders affected patients, IgGCtr), and stained for 30 min with PE-conjugated goat anti human IgG. Cells were washed and resuspended in 200 μL of PBS for flow cytometric analysis. EGFP-positive cells, corresponding to the R2 region shown in the FSC/SSC dot blot panel, were 43.8%. The value reported inside each FSC/FL-2 dot blot, represent the percent of FL-2 positive cells inside the R2 region (GFP-positive cells). The upper panel shows the binding of serum Ig (MS or neurological (N) patients) to mock transfected cells. In each panel, control cells incubated with secondary antibody alone, are shown.

Figure 4A:
Figure 4B:
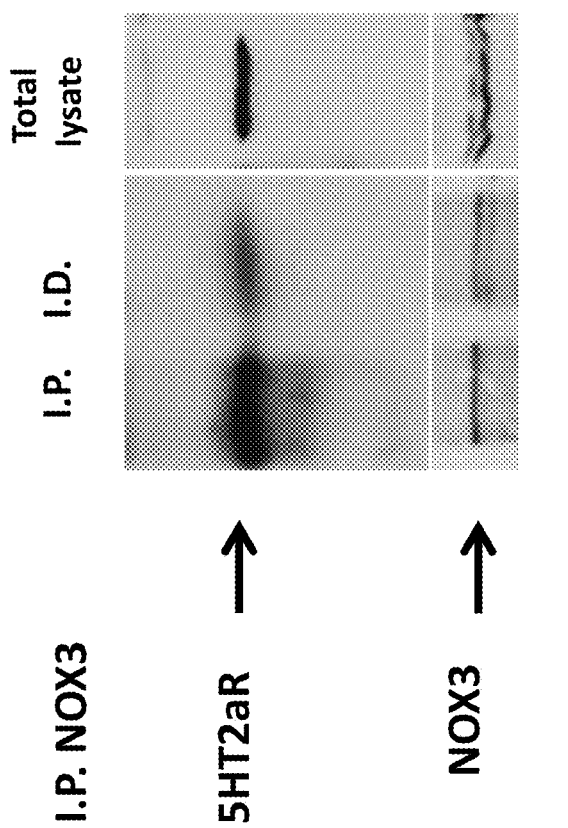

FIGS. 4A and 4B: 5Ht2a receptor interacts with NOX3 in MO3-13 cells. (A) PCR analysis of NOXs in MO3-13 cells. Total mRNA was extracted with Trizol, reverse transcribed and analyzed by PCR with specific primers to NOX1, NOX2, NOX3, NOX4 and NOX5. The PCR analysis was carried out at 35 number of cycles. CTR- represents negative control without template. (B) MO3-13 cells were incubated for 18 h in medium containing 0.2% FBS before harvesting them for immunoprecipitation with anti-human NOX3 antibody and immunoblot with anti-human 5Ht2a receptor antibody. I.D. shows the immunodepleted and I.P. immunoprecipitated samples. M, Molecular Weight Marker.

Figure 5:
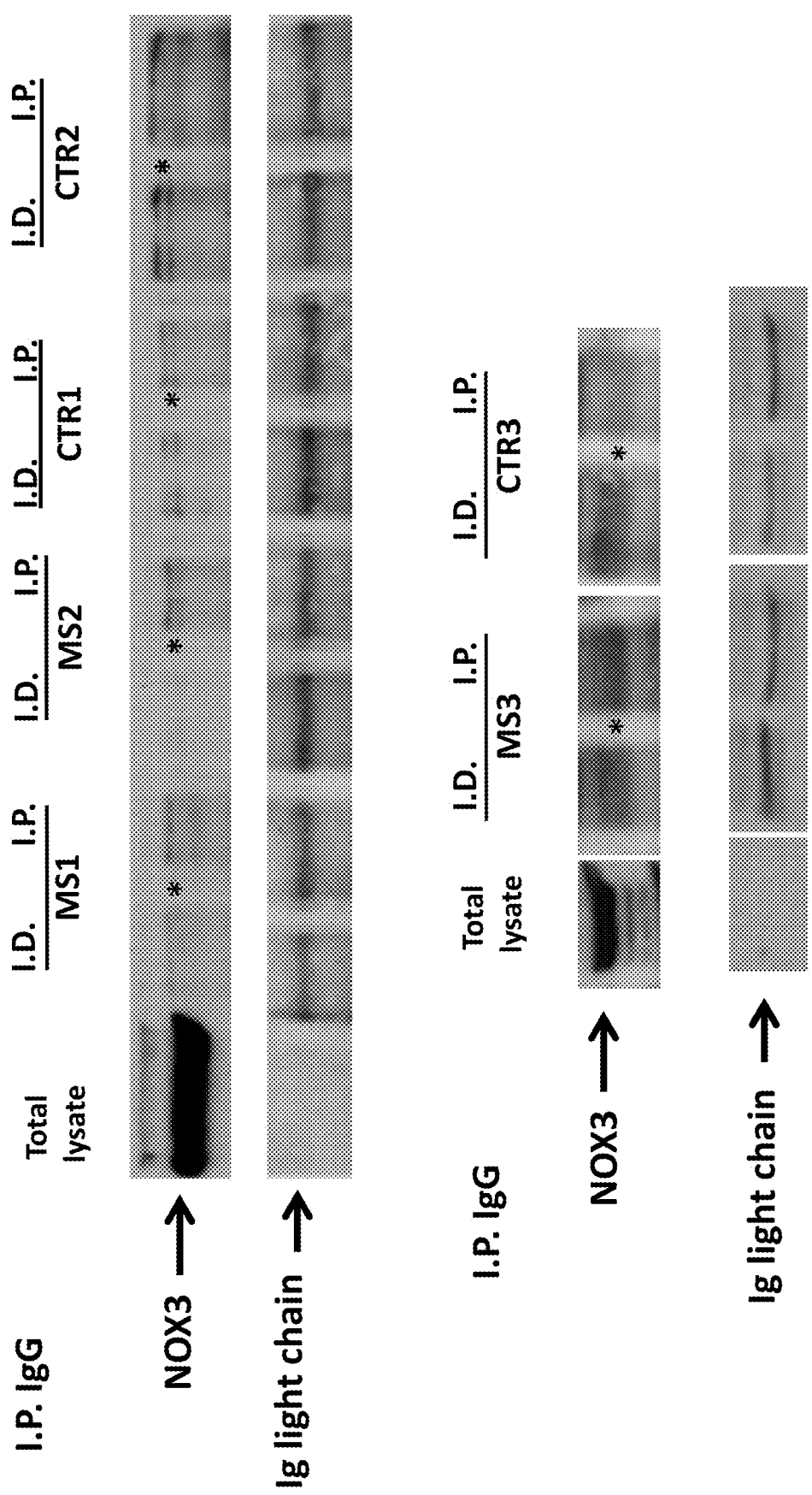

FIG. 5: IgG from MS patients bind to NOX3 in MO3-13 cells. MO3-13 cells were incubated for 18 h in medium containing 0.2% FBS before harvesting them for immunoprecipitation with IgG from 3 neurological (other neurological disorders affected patients, CTR1,CTR2 and CTR3) and 3 MS patients (MS1, MS2 and MS3) and immunoblot with human anti-NOX3 antibody. The image shows the blots of two different experiments. I.D. shows the immunodepleted and I.P. the immunoprecipitated samples. Asterisks indicate NOX3 band.

Figure 6:
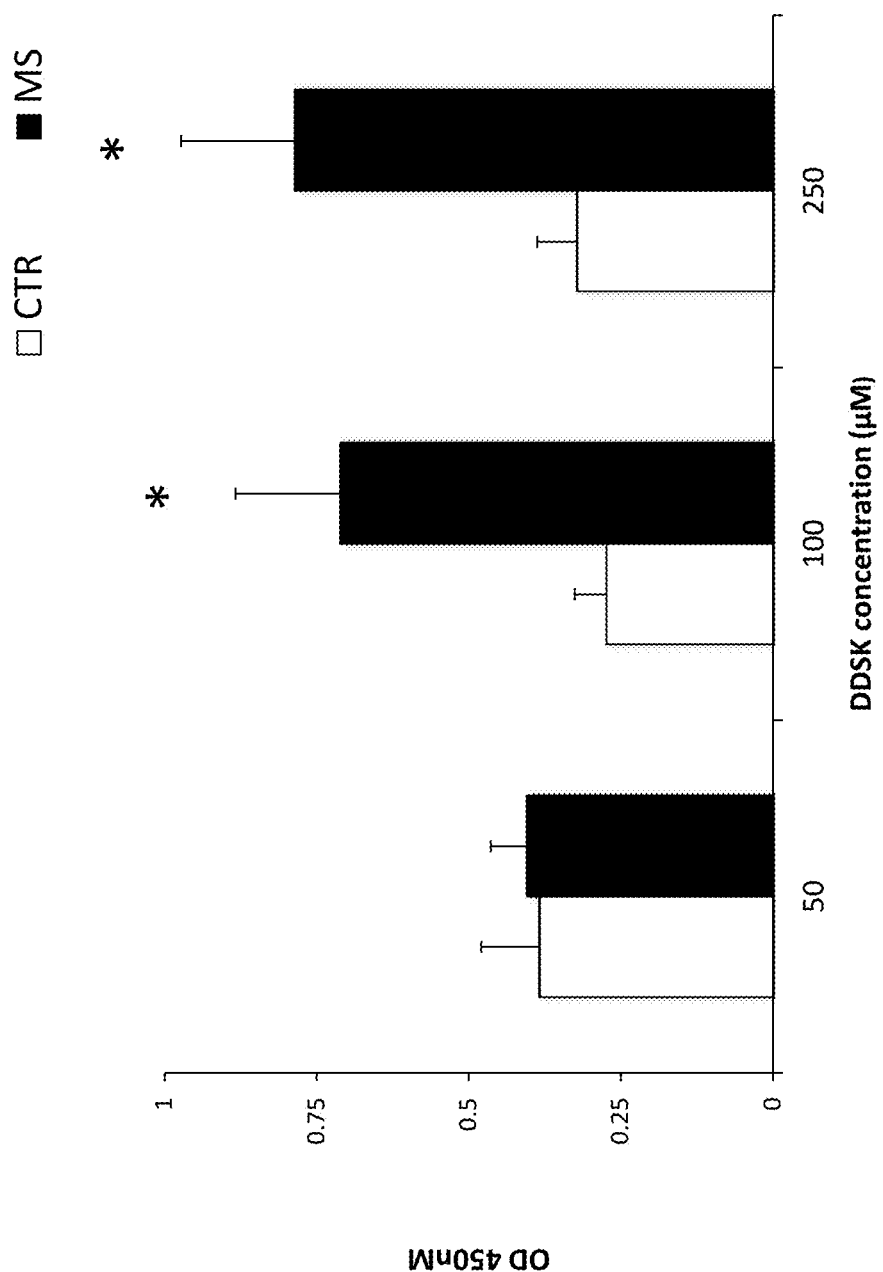
Figure 7A:
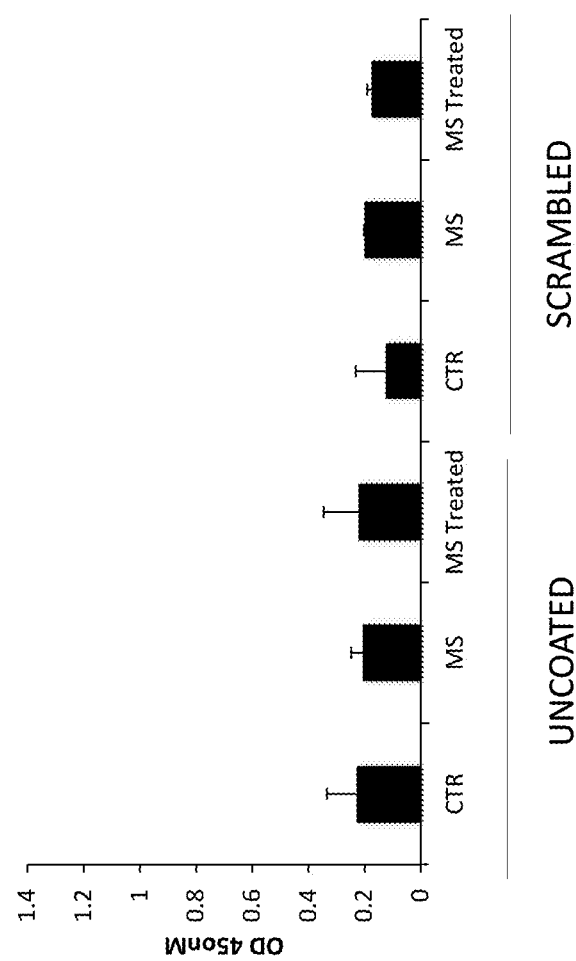
Figure 7B:
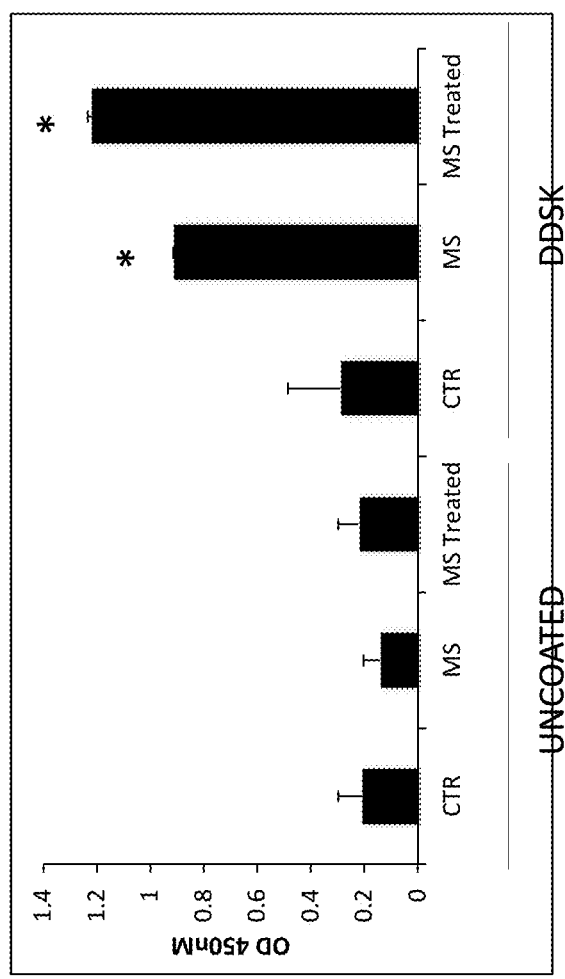
Figure 7C:
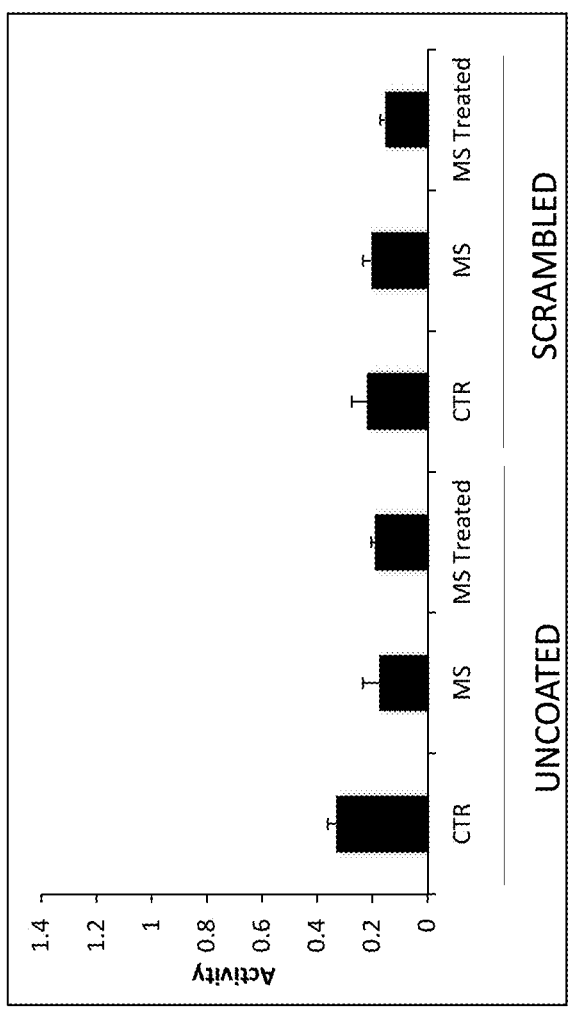
Figure 7D:
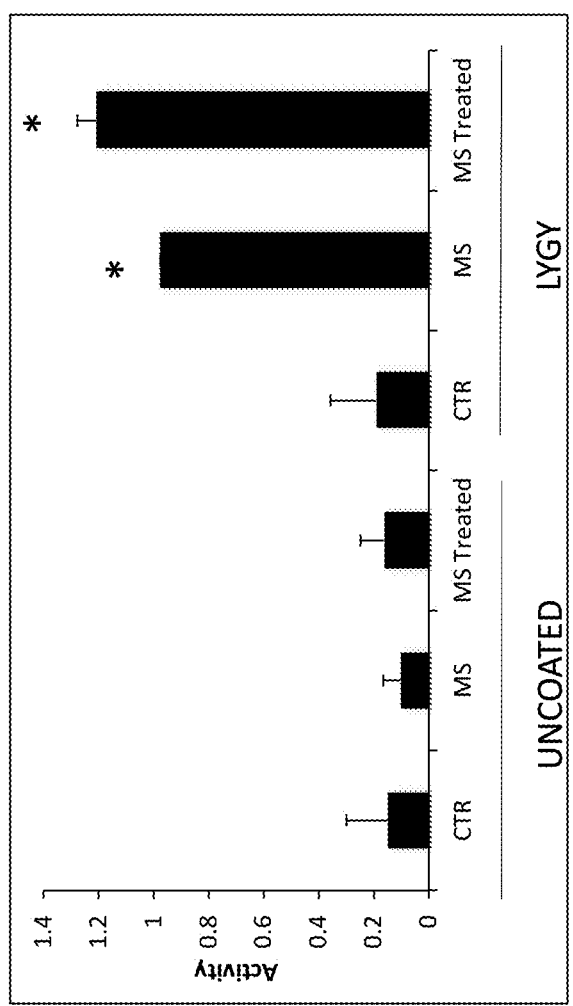

FIG. 6: Dose-response curves of the interaction between MS sera and DDSK peptide. (A) Sera of Multiple Sclerosis patients and Control (control group is defined in material and method below) (200 μg) were incubated with different concentrations (50-100-250 μM) of peptide DDSK. For the detection, inventors used a secondary antibody anti human IgG conjugated with HRP and (3,3',5,5'-Tetramethylbenzidine) TMB solution that was added for each well and incubated for 15-30 min. Equal volume of stopping solution (2 M H2SO4) was added to the plate and absorbance (optical density) of plate was read at 450 nm. The statistical analysis derived from 9 experiments. Values are mean±SEM. *P<0.05 MS vs CTRL (B) Linear representation of dose-response curve Values are mean±SEM. *P<0.05 MS vs CTRL.

FIGS. 7A, 7B, 7C and 7D: MS sera recognize specially receptor's peptides. Sera of Control, Multiple Sclerosis or treated with interferon Multiple Sclerosis patients (200 μg) were incubated in absence (uncoated) or presence of 100 μM scrambled peptide (A and C), DDSK (B) and LYGY (D). For the detection, the inventors used a secondary antibody anti human conjugated with HRP and (3,3',5,5'-Tetramethylbenzidine) TMB solution that was added for each well and incubated for 15-30 min. Equal volume of stopping solution (2 M H2SO4) was added to the plate and absorbance (optical density) of plate was read at 450 nm. The statistical analysis derived from 3 experiments. Values are mean±SEM. *P<0.01 MS and MS Treat vs CTRL.

Figure 8A:
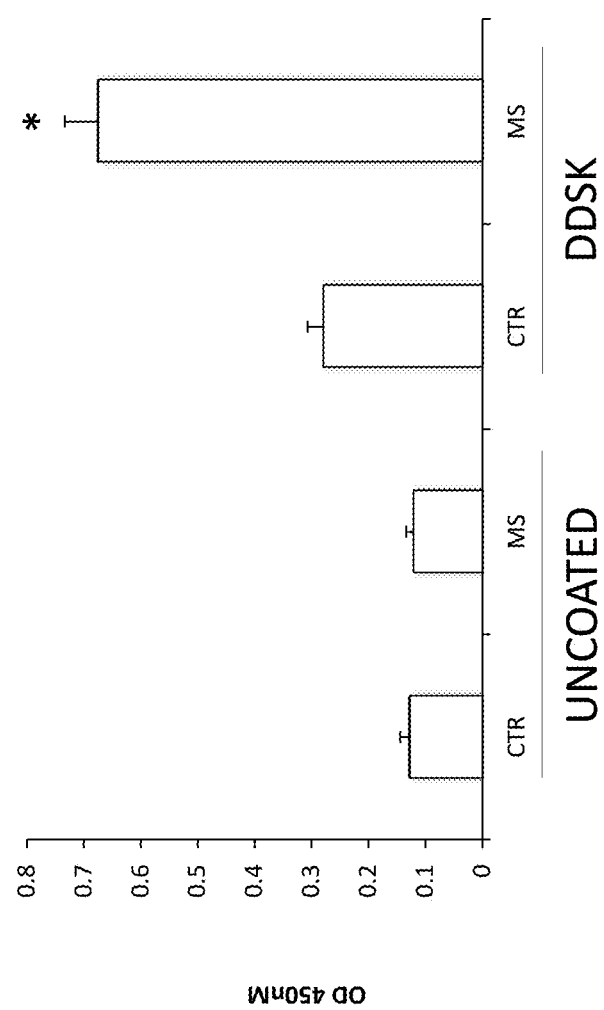
Figure 8B:
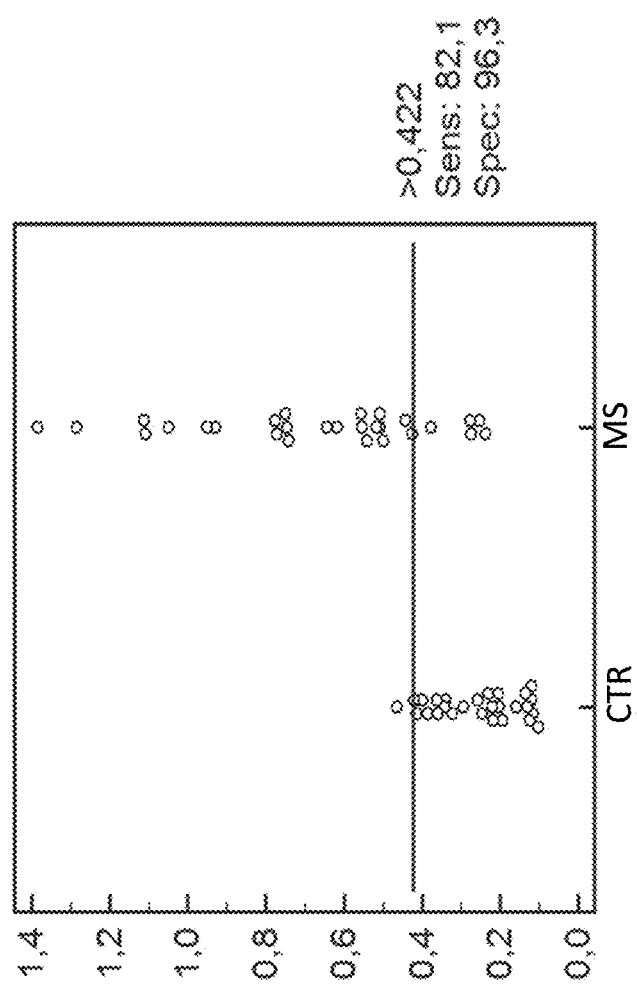

FIGS. 8A and 8B: DDSK peptide shows high sensitivity and specificity to sera MS. A. Sera of Multiple Sclerosis patients and Control (200 μg) were incubated in absence (uncoated) or presence of 100 μM of DDSK peptide. For the detection, the inventors used a secondary antibody anti human IgG conjugated with HRP and (3,3',5,5'-Tetrannethylbenzidine) TMB solution that was added for each well and incubated for 15-30 min. Equal volume of stopping solution (2 M H2SO4) was added to the plate and absorbance (optical density) of plate was read at 450 nm. The statistical analysis derived from 28 experiments. Values are mean±SEM. *P<0.001 MS vs CTRL. B. ROC test of averages of the pool shows a sensitivity of 82% and a specifity of 96% to MS patients respect to CTR patients sera (n=28).

Figure 9A:
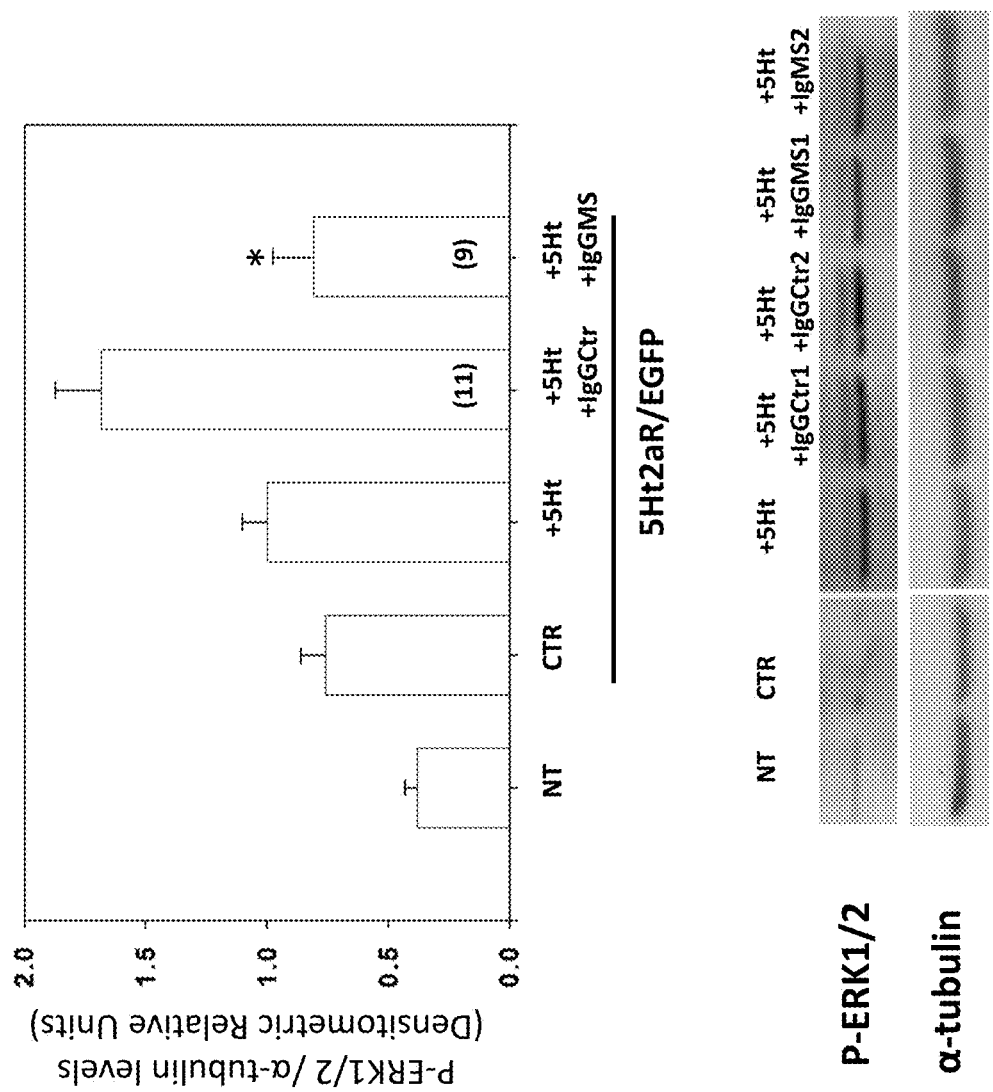

FIG. 9A: IgG from MS patients inhibit 5Ht-mediated P-ERK induction in HEK-293 cells transfected with 5HT2aR-EGFP construct. HEK-293 cells were transfected with a plasmid containing the human 5-HT2A receptor gene conjugated to the enhanced green fluorescent protein, EGFP. Cells, harvested for 18 h in medium containing 0.2% FBS, were then stimulated with 5 uM 5Ht for 15 min in the presence or absence of 200 ug/ml of serum IgG from MS (IgGMS) or Neurological patients (IgGCtr). Then cells were harvested and lysates were subjected to immunoblot analysis for P-EKR1/2 levels. The histograms shows the values (means±SEM) relative to 5-HT2 stimulated sample, obtained by densitometric analysis of protein bands normalized to α-Tubulin of three independent experiments. NT indicates not transfected cells and CTR, cells transfected with empty plasmid. The values in brackets inside the hystograms indicate the numbers of Ig tested for each group of patients. The lower part of the figure shows a representative experiment. *p<0.001 vs IgGCtr FIG. 9B: The serotonin receptor antagonist risperidone reverts the effects of IgG from MS patients on pERK1/2 levels in MO3-13 cells. Western blotting analysis of P-ERK1/2 levels in MO3-13 cells harvested for 18 h in medium containing 0.2% FBS, preincubated with risperidone (Risp) (10 uM) for 30 min in serum-free medium and then stimulated for 30 min with IgG (200 µg/ml) purified from serum of Control (IgCtr) or MS (IgMS) patients. The same membrane was also incubated with α-Tubulin antibody to show the protein loading.

Figure 10A:
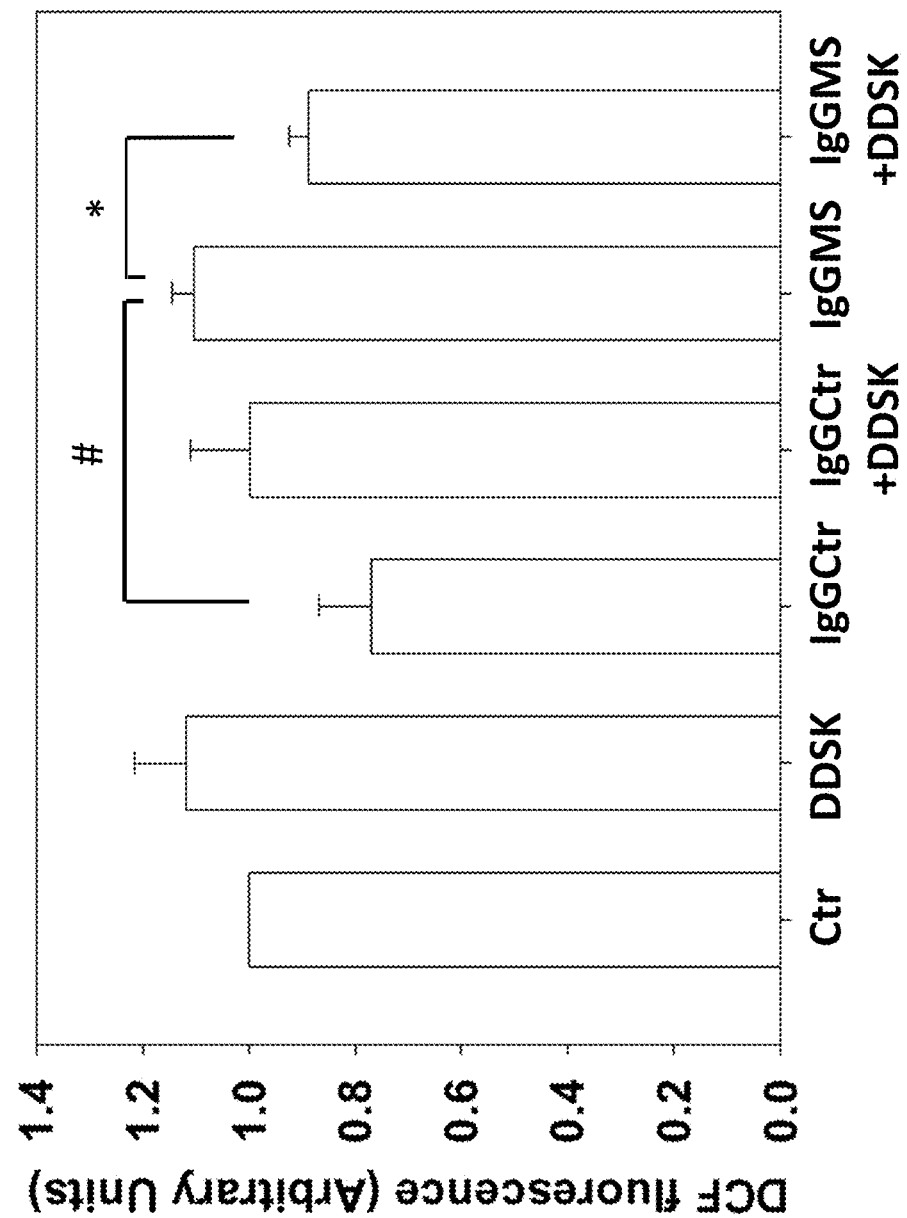

FIG. 10A: DDSK peptide reverts the effects of Ig from MS patients on ROS levels in MO3-13 cells. MO3-13 cells were grown to semi-confluence in 24 multiwell plates and incubated for 18 h in medium containing 0.2% FBS. The cells were washed twice with FBS free medium, incubated with 50 µM of DDSK for 30 min and then with 200 µg/ml of IgG from Control (IgGCtr) or MS (IgGMS) patients for 30 min. Then, the cells were incubated with 10 µM DCHF-DA for 10 min, washed three times and DCF fluorescence was measured using a plate reader fluorometer. The histograms show the mean+/−SEM values obtained in 5 different experiments from 7 control and 7 MS subjects. # $p<0.05$ vs IgGCtr; *$p<0.05$ vs IgGMS.

Figure 10B:
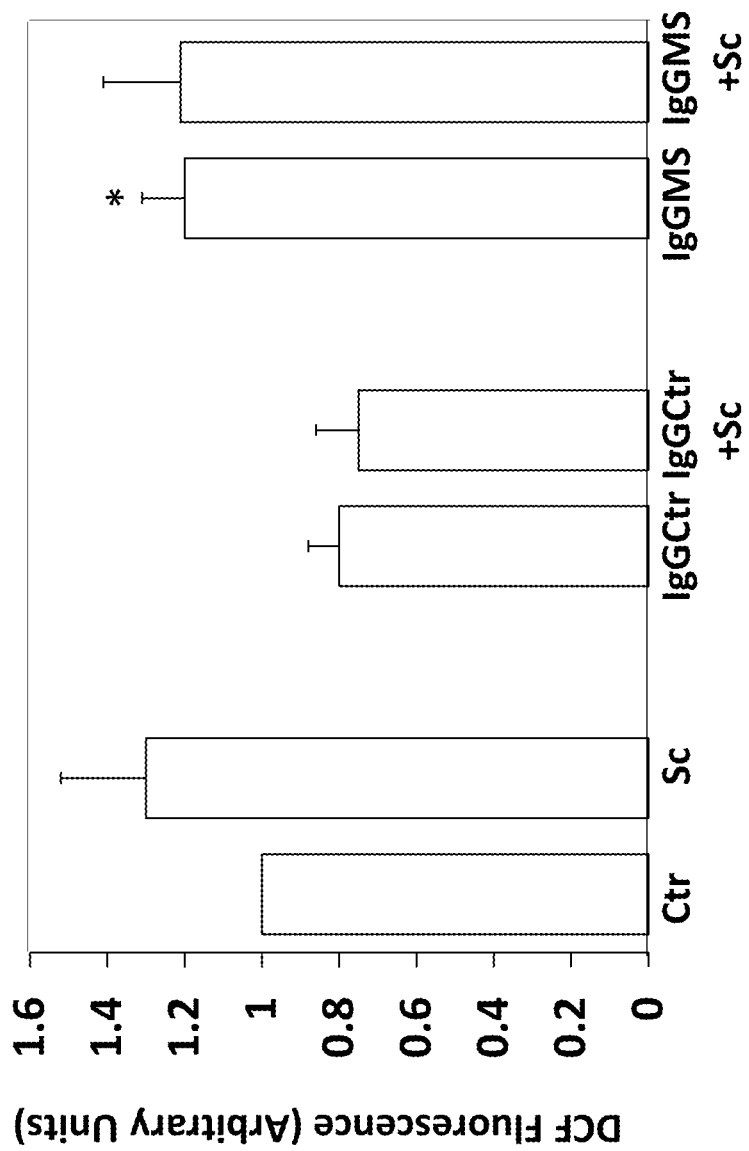

FIG. 10B: Scrambled peptide does not influence IgMS effects on ROS levels in MO3-13 cells. MO3-13 cells were grown to semi-confluence in 24 multiwell plates and incubated for 18 h in medium containing 0.2% FBS. The cells were washed twice with FBS free medium, incubated with 50 µM of Scrambled peptide (Sc) for 30 min and then with 200 µg/ml of IgG from Control (IgGCtr) or MS (IgGMS) patients for 30 min. Then, the cells were incubated with 10 µM DCHF-DA for 10 min, washed three times and DCF fluorescence was measured using a plate reader fluorometer. The histograms show the mean+/−SEM values obtained from 3 control and 3 MS subjects. *$p<0.05$ vs IgGCtr.

Figure 11:
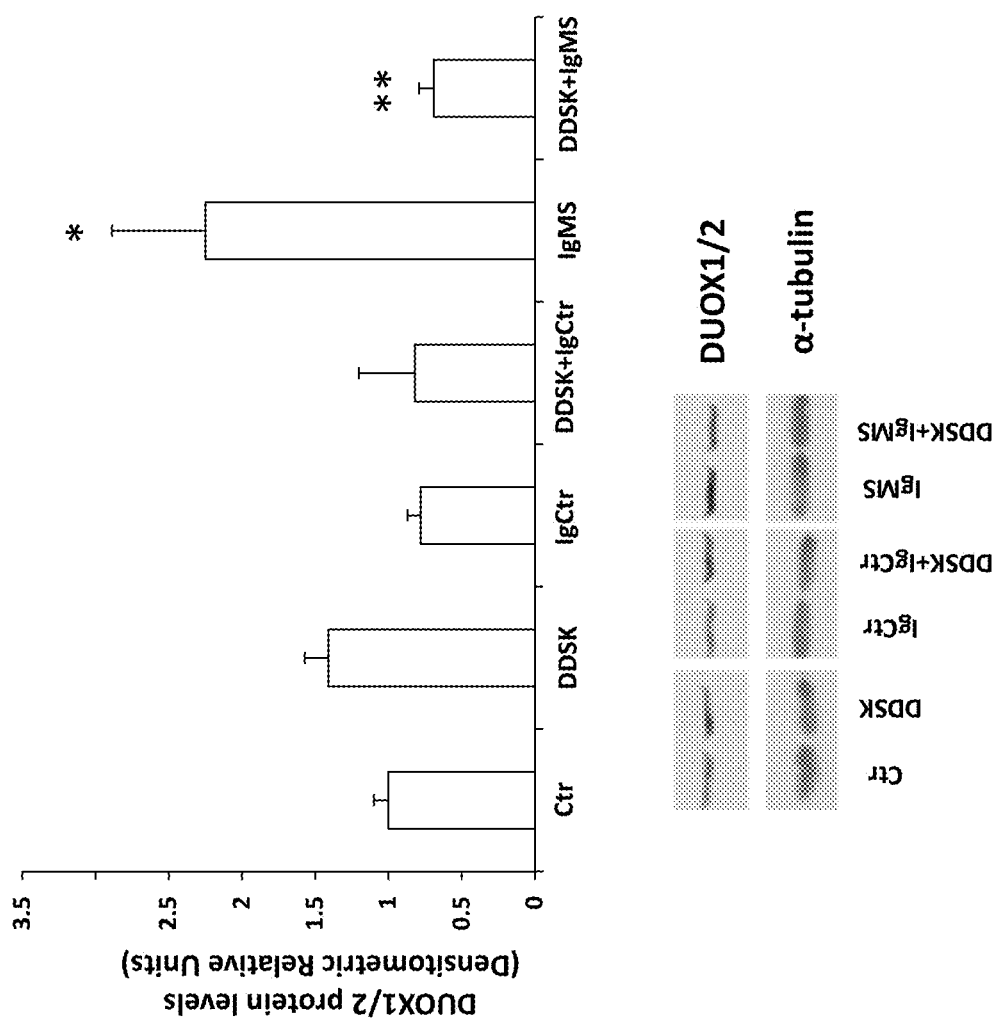

FIG. 11: DDSK peptide reverts the effects of Ig from MS patients on DUOX1/2 protein levels in MO3-13 cells. Western blotting analysis of DUOX1/2 expression levels in MO3-13 cells harvested for 18 h in medium containing 0.2% FBS, preincubated with DDSK (50 uM) for 30 min in serum-free medium and then stimulated for 30 min with IgG (200 µg/ml) purified from serum of Control (IgCtr) or MS (IgMS) patients. The histogram shows the values (means+/−SEM) relative to control (not stimulated cells) obtained by densitometric analysis of protein bands normalized to α-Tubulin of three independent experiments. *$p<0.05$ vs IgCtr; **$p<0.05$ vs IgMS. The lower part of the figure shows a representative experiment.

Figure 12:
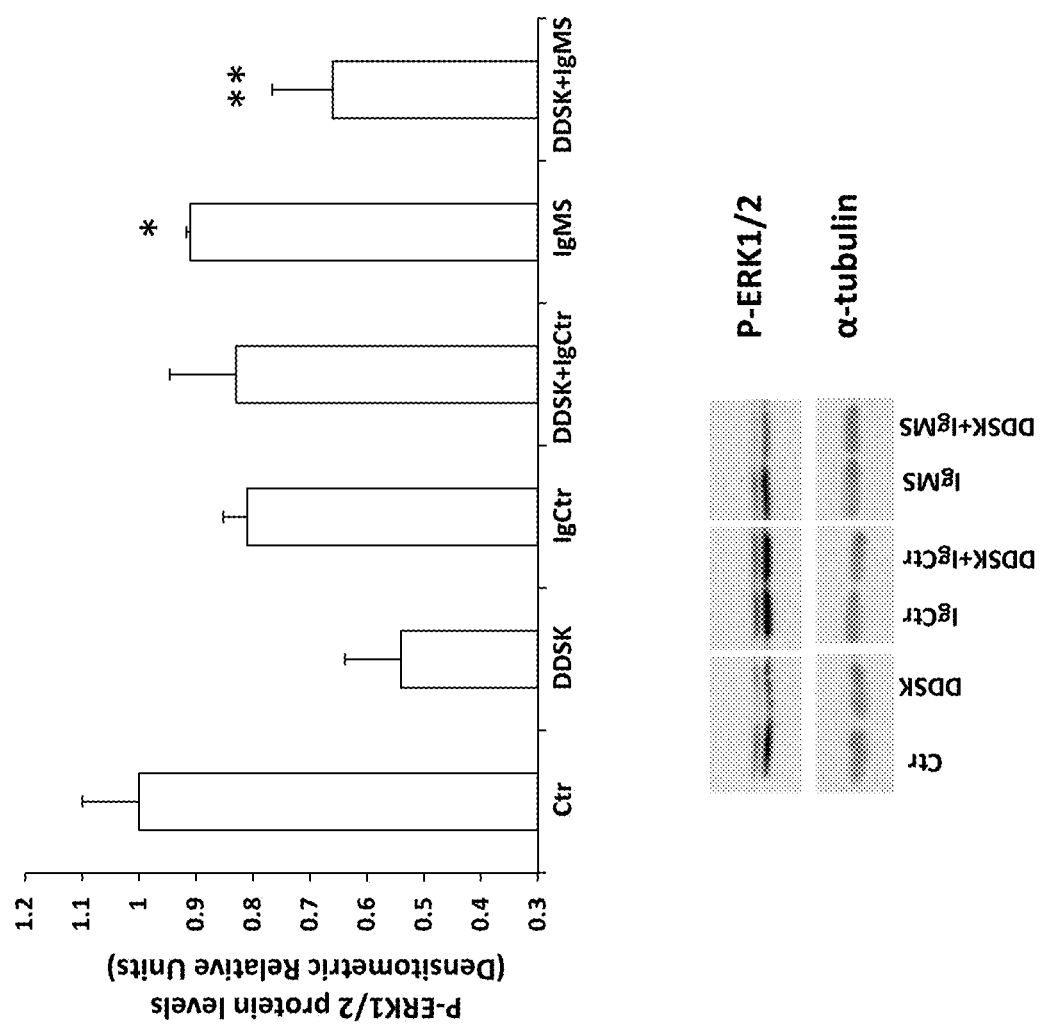

FIG. 12: DDSK peptide reverts the effects of Ig from MS patients on P-ERK1/2 protein levels in MO3-13 cells. Western blotting analysis of P-ERK1/2 expression levels in MO3-13 cells harvested for 18 h in medium containing 0.2% FBS, preincubated with DDSK (50 uM) for 30 min in serum-free medium and then stimulated for 30 min with IgG (200 µg/ml) purified from serum of Control (Ig Ctr) or MS (IgMS) patients. The histogram shows the values (means+/−SEM) relative to control (not stimulated cells) obtained by densitometric analysis of protein bands normalized to α-Tubulin of three independent experiments. *$p<0.05$ vs IgCtr; **$p<0.05$ vs IgMS. The lower part of the figure shows a representative experiment.

Figure 13:
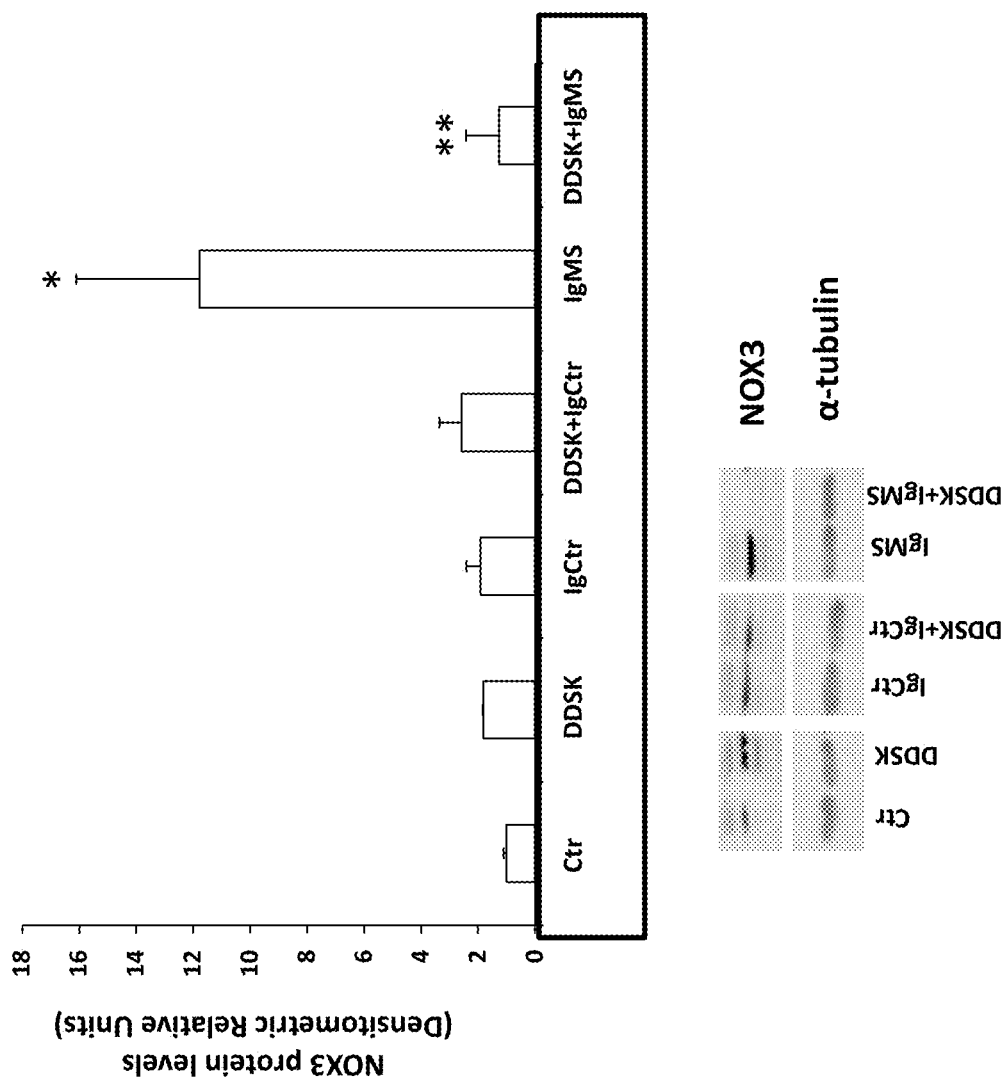

FIG. 13: DDSK peptide reverts the effects of Ig from MS patients on NOX3 protein levels in MO3-13 cells. Western blotting analysis of NOX3 expression levels in MO3-13 cells harvested for 18 h in medium containing 0.2% FBS, preincubated with DDSK (50 uM) for 30 min in serum-free medium and then stimulated for30 min with IgG (200 µg/ml) purified from serum of Control (IgCtr) or MS (IgMS) patients. The histogram shows the values (means+/−SEM) relative to control (not stimulated cells) obtained by densitometric analysis of protein bands normalized to α-Tubulin of three independent experiments. *$p<0.05$ vs IgCtr; **$p<0.05$ vs IgMS. The lower part of the figure shows a representative experiment.

Figure 14:
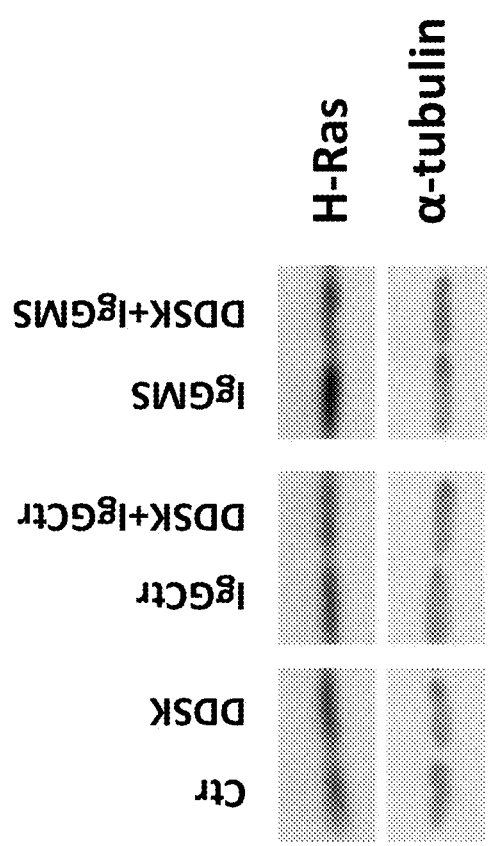

FIG. 14: DDSK peptide reverts the effects of Ig from MS patients on H-Ras protein levels in MO3-13 cells. Western blotting analysis of H-Ras expression levels in MO3-13 cells harvested for 18 h in medium containing 0.2% FBS, preincubated with DDSK (50 uM) for 30 min in serum-free medium and then stimulated for30 min with IgG (200 µg/ml) purified from serum of Control (Ig Ctr) or MS (IgMS) patients. The same membrane was incubated with α-Tubulin antibody to show the protein loading.

FIGS. 15A, 15B, 15C and 15D: Multiple sequence alignments of peptides 1-48 of the invention with the extracellular loops of the 5-HT2A receptor. Alignments show that each extracellular region of the 5HT2A receptor has a high affinity for MS sera.

FIGS. 16A and 16B: Multiple sequence alignments of peptides of the invention with the extracellular loops of the NOX2. Alignments show that extracellular region of loop 2 (FIG. 16A) and loop 3 (FIG. 16B) of the NOX2 has a high affinity for MS sera.

Specific Embodiments Of The Invention

1. A peptide consisting of an amino acid sequence that is 100% identical to:
  (a) LYGYRWPLPSKL (SEQ ID NO: 158);
  (b) YRWPLPSKL (SEQ ID NO: 14);
  (c) RWPLPSKL (residues 2-9 of SEQ ID NO: 14);
  (d) RWP (residues 2-4 of SEQ ID NO: 14); or
  (e) SKL (residues 7-9 of SEQ ID NO: 14);
wherein the peptide is able to bind multiple sclerosis auto-antibodies.

2. The peptide according to embodiment 1 wherein the sequence consists of YRWPLPSKL (SEQ ID NO: 14).

3. The peptide according to embodiment 1 wherein the sequence consists of RWPLPSKL (residues 2-9 of SEQ ID NO: 14).

4. The peptide according to embodiment 1, wherein the sequence consists of RWP (residues 2-4 of SEQ ID NO: 14).

5. The peptide according to embodiment 1, wherein the sequence consists of SKL (residues 7-9 of SEQ ID NO: 14).

6. The peptide according to embodiment 1, in linear or conformational form.

7. A pharmaceutical composition comprising the peptide according to embodiment 1, and pharmaceutically acceptable excipients.

8. The pharmaceutical composition according to embodiment 7, further comprising a therapeutic agent, selected from the group consisting of vitamins, nootropics, neuroprotective agents, anti-pain medication, racetams, isoflavones, vitamins, choline, amphetamines, xanthines, adrenergics, cholinergics, serotonigergic, dopaminergics, eugeroics, GABA blockers, AMPAkines, PDE4 inhibitors, glutamate antagonists, statins, antioxidants, caspase inhibitors, neurotrophic factors, antiapoptotic agents, and anti-pain medications.

9. A method for detecting multiple sclerosis auto-antibodies in a patient, the method comprising:
  (a) obtaining a biological sample isolated from the patient; and (b) detecting whether multiple sclerosis auto-antibodies are present in the biological sample by contacting the biological sample with a peptide, and detecting binding between multiple sclerosis auto-antibodies and the peptide ;
  wherein the peptide comprises a peptide according to embodiment 1.

10. A kit for diagnosing or monitoring the progression of multiple sclerosis, or for identifying or monitoring a therapy for multiple sclerosis, comprising the peptide according to embodiment 1.

11. A nucleic acid molecule encoding a peptide consisting of an amino acid sequence that is 100% identical to: LYGYRWPLPSKL (SEQ ID NO: 158), wherein the peptide is able to bind multiple sclerosis auto-antibodies.

12. The pharmaceutical composition according to embodiment 7, further comprising a therapeutic agent selected from the group consisting of b-interferon, methylphenidate, vitamin B, vitamin C, vitamin D, vitamin E, choline, 17β-Estradiol, ginsenoside Rd, progesterone, nicotine, caffeine, and natalizumab.

13. The pharmaceutical composition according to embodiment 7, further comprising a peptide or fragment thereof consisting of an amino acid sequence that is 100% identical to SEQ ID NO: 157.

14. The pharmaceutical composition according to embodiment 13, wherein the fragment consists of the sequence SKVFKEGS (residues 3-10 of SEQ ID NO: 157).

15. The pharmaceutical composition according to embodiment 13, wherein the fragment consists of FKE (residues 6-8 of SEQ ID NO: 157).

16. The method according to embodiment 9, further comprising:
  (c) detecting whether multiple sclerosis auto-antibodies are present in the biological sample by contacting the biological sample with the peptide or fragment thereof consisting of the amino acid sequence of SEQ ID NO: 157, and detecting binding between multiple sclerosis auto-antibodies and the peptide or fragment thereof comprising the amino acid sequence of SEQ ID NO: 157.

17. A kit according to embodiment 10, further comprising a peptide consisting of the amino acid sequence of SEQ ID NO: 157 or fragment thereof.

18. A method for detecting multiple sclerosis auto-antibodies in a patient according to embodiment 9, further comprising using the detection of binding between multiple sclerosis auto-antibodies and the peptide for diagnosing or monitoring the progression of multiple sclerosis, identifying a therapy for multiple sclerosis, or monitoring a therapy for multiple sclerosis.

20. The method according to embodiment 16 wherein the fragment of the peptide of SEQ ID NO: 157 consists of the sequence SKVFKEGS (residues 3-10 of SEQ ID NO: 157).

21. The method according to embodiment 16 wherein the fragment of the peptide of SEQ ID NO: 157 has the sequence FKE (residues 6-8 of SEQ ID NO: 157).

22. A method for detecting multiple sclerosis auto-antibodies in a patient according to embodiment 16, further comprising using the detection of binding between multiple sclerosis auto-antibodies and the peptide of SEQ ID NO: 157 or fragment thereof wherein said fragment has the sequence SKVFKEGS or FKE for diagnosing or monitoring the progression of multiple sclerosis, identifying a therapy for multiple sclerosis, or monitoring a therapy for multiple sclerosis.

DETAILED DESCRIPTION OF THE INVENTION

Materials and Methods
Patients

In the study MS group comprises men and women between 15 and 50 years of age who meet all the following criteria:
  diagnosis of relapsing/remitting MS, according to McDonald criteria;
  an Expanded Disability Scale Score (EDSS) between O and 5.0;
  lesions detected by MRI compatible with the diagnosis of multiple sclerosis;
  at least one acute episode in the last 12 months.

Control samples include other neurological disorders affected patients (including inflammatory, degenerative diseases not involving direct or indirect de-myelinization, i. e.: cerebral cancers, stroke, vasculitis, etc) that need differential diagnosis with multiple sclerosis. Control patients were selected by sex and age to be similar to multiple sclerosis patients. Blood serum was collected, from each patients. From the blood serum, to perform the experiments on cell culture, the IgG fractions were purified.

Patients gave written informed consent before any study-related procedures was performed.

Purification of Immunoglobulins

The purification of IgG fractions from serum of MS and control Neurological subjects has been carried out by affinity chromatography on A/G Sepharose columns (Pierce, Rockford, Ill.). The protein concentration of immunoglobulin fractions has been assessed spectrophotometrically.

Cell Cultures
  MO3-13 Cells

The MO3-13 cells are an immortal human-human hybrid cell line with the phenotypic characteristics of primary oligodendrocytes (OLs), derived from the fusion of a 6-thioguanine-resistant mutant of a human rhabdomyosarcoma with OLs obtained from adult human brain (CELLution Biosystem Inc., Canada). They were grown in Dulbecco's Modified Eagles Medium (DMEM; GIBCO Invitrogen), containing 4.5 g/L glucose (GIBCO, Auckland, New Zealand), supplemented with 10% Foetal Bovine Serum, 100 U/ml penicillin and 100 µg/ml streptomycin (FBS; Sigma S. Louis, USA).

HEK293 Cells

HEK293 is a cell line derived from human embryonic kidney cells (American Type Culture Collection, ATCC, USA). They were grown in Dulbecco's Modified Eagles Medium (DMEM; GIBCO Invitrogen), containing 4.5 g/L glucose (GIBCO, Auckland, New Zealand), supplemented with 10% FBS, 100 U/ml penicillin and 100 µg/ml (Sigma S. Louis, USA).

Hela and SH-SY5Y Cells

The human cervical adenocarcinoma Hela cells and the human neuroblastoma SH-SY5Y cell lines (American Type Culture Collection, ATCC, USA) were grown in DMEM-F12 medium (GIBCO Invitrogen) containing 4.5 g/L glucose (GIBCO, Auckland, New Zealand), supplemented with 10% FBS (Sigma S. Louis, USA), 100 U/ml penicillin and 100 µg/ml. The cells were kept in a 5% CO2 and 95% air atmosphere at 37° C.

Flow Cytometric Assay of 5-Ht2AR

MO3-13 cells were grown to semiconfluency in 60-mm culture dishes. After trypsin detachment, $5 \cdot 10^5$ cells were suspended in 1 mL of phosphate buffered saline (PBS) and fixed overnight with 1% formaldehyde at room temperature.

Next, cells were permeabilized with 0.1% Triton X-100 for 40 min at 4° C., washed 4× with 2 mL of PBS containing 2% FBS, 0.01% NaN3, 0.1% Triton X-100 (buffer A), and incubated for 45 min at 4° C. with 1:50 dilution of Rabbit polyclonal to 5HT2aR antibody (Abcam ab81864). The cells were then washed twice with the same buffer and incubated for 45 min at 4° C. with Cy3-conjugated anti-(rabbit IgG) Ig (Amersham Pharmacia Biotech) at 1:50 dilution. Control cells were incubated with Cy3-conjugated anti-(rabbit IgG) IgG alone. After two washes in buffer A, cells were resuspended in PBS and analyzed by flow cytometry using FACSCAN (BD, Heidelberg, Germany) and WINMDI software.

Flow Cytometric Assay of Serum IgG Binding to 5-HT2aR

HEK293 cells were plated in 100 mm Petri dishes and grown to semiconfluence. After trypsinization and wash in PBS, the cells were resuspended in 200 µl PBS and then incubated with mouse serum for 30 min at 4° C., to block nonspecific binding; then, they were incubated for 30 min with 200 µg of serum IgG (MS or neurological), and stained for 30 min with PE-conjugated goat anti human IgG. Cells were washed and resuspended in 200 µL of PBS for flow cytometric analysis of phycoerythrin positive cells with a FACSscan apparatus (Becton-Dickinson). Data were analyzed using WinMDI software.

Immunoprecipitation and Immunoblotting Experiments

MO3-13 cells, grown to semiconfluence in 100 mm dishes, were incubated for 18 h in 0.2% FBS medium.

The cells were washed twice with PBS and harvested in cold RIPA buffer containing 2.5 mM Na-pyrophosphate, 1 mM β-glycerophosphate, 1 mM NaVO4, 1 mM NaF, 0.5 mM PMSF, and the cocktail of protease inhibitors. The cells were kept for 15 min at 4° C. and disrupted by repeated aspiration through a 21-gauge needle. Cellular debris was pelleted by centrifugation at 11600 g for 15 min at 4° C. 300 µg of cellular lysates were immunoprecipitated with IgG from Neurological or MS patients at 1:10 dilution. Samples were rocked gently for 16 h; thereafter 20 µl of protein A/G PLUS-Agarose (Santa Cruz Biotechnology), resuspended in RIPA buffer, was added to immunoprecipitates. Samples were further rocked for 1 h, centrifuged at 3000 rpm. Supernatants were collected and the protein A/G PLUS-Agarose was added again, to obtained the immunodepleted samples. Then, the pellets were washed thrice in RIPA buffer and once with PBS before the addition of 20 µl Laemmli sample buffer.

Immunoprecipitated/immunodepleted samples and 50 µg of total lysates in Laemmli buffer were boiled for 5 min and centrifuged for 1 min at 11600 g at room temperature (22° C.). The pellets were discarded and supernatants were resolved by 7.5% SDS-PAGE and transferred onto nitrocellulose membrane.

Next, the membrane was blocked in 3% dry-fat milk in TBS-Tween20 (0.05%) and probed with a polyclonal anti-human anti NOX3 (Abcam ab81864) or 5HT-2a receptor (Abcam ab85496) antibodies at 1:1000 dilution. Then, the membrane was washed and incubated with a secondary horseradish peroxidase-linked antibody (Amersham Pharmacia Biotech) 1:2000 and was detected by ECL.

Indirect ELISA

Diluted peptide (20 µg/ml) was coated to the wells of a PVC microtiter plate and incubated at 4° C. overnight. After many wash, the remaining protein-binding sites was blocked with 3% BSA solution and incubated at 4° C. overnight. The patient extracted immunoglobulins was diluted in blocking buffer and incubated at 4° C. overnight. The plate was washed for four times with PBS. For the detection, we used a secondary antibody anti human (recognized constant region of the patient antibody conjugated with HRP and (3,3',5,5'-Tetramethylbenzidine) TMB solution that was added for each well and incubated for 15-30 min. Equal volume of stopping solution (2 M H2SO4) was added to the plate and absorbance (optical density) of plate was read at 450 nm.

ELISA with Beads

Beads linked Peptide ($6 \times 10^4$ beads/sample) were mixed with different concentrations of patient extracted immunoglobulins for 16 h at 4° C. in a rotator. The beads were washed twice with PBS by centrifugation at 14,000 rpm for 2 min at room temperature and were resuspended in 100 µl of PBS. For the detection, we used a secondary antibody anti human (recognized constant region of the patient antibody conjugated with HRP and (3,3',5,5'-Tetramethylbenzidine) TMB solution that was added for each well and incubated for 15-30 min. Equal volume of stopping solution (2 M H2SO4) was added to the plate and absorbance (optical density) of plate was read at 450 nm.

Detection of Peptide/Immunoglobulins Derived from Patients Interaction on Beads by Flow Cytometry Beads linked Peptide ($6 \times 10^4$ beads/sample) were mixed with different concentrations of patient extracted immunoglobulins for 16 h at 4° C. in a rotator. The beads were washed twice with PBS by centrifugation at 14,000 rpm for 2 min at room temperature and were resuspended in 100 µl of PBS. Then, the samples was incubated with anti-human secondary antibodies conjugated with FITCH and beads were analyzed on a BD FACS Calibur (Becton-Dick-inson, Franklin Lakes, N.J.), and the data analyzed on FlowJo (Treestar, Ashland, Oreg.) software.

Determination of Reactive Oxygen Species

ROS levels were determined using the membrane-permeant fluorogenic probe 5,6-carboxy-2',7'-dichlorofluoresceindiacetate, DCHFDA (Molecular Probes, Leiden, the Netherlands). The assay was based on the fluorescence detection of dichlorofluorescein (DCF), formed by ROS-mediated oxidation of the non-fluorescent precursor, dichlorofluorescin.

MO3-13 cells were grown to semi-confluence in 24 multiwell plates (45000 cell/well) and incubated for 18 h in medium containing 0.2% FBS before the experiments. The cells were washed twice with FBS free medium and incubated with 50 µM of DDSK for 30 min at 37° C. and then with 200 µg/ml of IgG from Ctr or MS patients (Damiano et al., 2013) for 30 min at 37° C. The cells were incubated with 10 µM DCHF-DA for 10 min and washed three times with PBS containing 10 mM glucose, 1.2 mM MgCl2 and 1.2 mM $CaCl_2$. DCF fluorescence was measured using the plate reader Fluoroskan Ascent FL fluorometer (Thermo Electron Oy, Vantaa, Finland) and data analyzed by Ascent software.

To evaluate the effects of 5Ht on ROS levels, a dose of 50 µM of the substance was added to the cells after DCHF-DA incubation and DCF fluorescence was measured at different time intervals.

Semi-Quantitative PCR Analysis

Total RNA was extracted using Trizol reagent according to the protocol provided by the manufacturer (Sigma-Aldrich). Total RNA (1 µg) was reverse transcribed using Transcriptor First Strand cDNA Syn-thesis Kit (Roche Applied Science, Monza, Italy) by oligo-dT primers for 30 min at 55° C. in a 20 µl reaction volume. Semi-quantitative PCR was performed using Hot Master TaqDNA Polymerase (SPRIME) in 20 µl final volume containing 0.2 mM dNTP, 0.2 µM of the specific primers and 100 ng of sample cDNA. The PCR conditions used were 94° C. 2 min, (94° C. 30 s, 60° C. 30 s, 70° C. 30 s) and 70° C. 5 min. The reactions were carried out at 35 number of cycles. Primers used in these experiments are the following:

```
Human NOX1:
                                          (SEQ ID NO: 159)
(F), TTA ACA GCA CGC TGA TCC TG (SEQ ID NO: 160)
(R), CAC TCC AGTGAG ACC AGC AA.

Human cytochrome b-245. beta polypeptide (CYBB,
alias NOX2):
                                          (SEQ ID NO: 161)
(F), GGA GTT TCA AGA TGC GTG GAA ACT A (SEQ ID NO: 162)
(R), GCC AGA CTC AGAGTT GGA GAT GCT.

Human NOX 3:
                                          (SEQ ID NO: 163)
(F), CCA GGG CAG TAC ATC TTG GT (SEQ ID NO: 164)
(R), CCG TGTTTC CAG GGA GAG TA.

Human NOX4:
                                          (SEQ ID NO: 165)
(F), GCT TAC CTC CGA GGA TCA CA (SEQ ID NO: 166)
(R), CGG GAGGGT GGG TAT CTA A.

Human NOX 5:
                                          (SEQ ID NO: 167)
(F), ATC AAG CGG CCC CCT TTT TTT CAC (SEQ ID NO: 168)
(R), CTCATT GTC ACA CTC CTC GAC AGC.

Human 5HT2A:
                                          (SEQ ID NO: 169)
(F) TCATCATGGCAGTGTCCCTA (SEQ ID NO: 170)
(R), TGAGGGAGGAAGCTGAAAGA.

B-actin:
                                          (SEQ ID NO: 171)
(F) TCACCCTGAAGTACCCCATC (SEQ ID NO: 172)
(R), GGCTGGAAGAGTGCCTCA.
```

Plasmid h-5HT2aR/EGFP construct: h-5HT2aR gene (NCBI Accession Number: NP_000612) has been inserted in the pEGFP-N3 vector from Clontech. The cDNA is cloned between BamHI and BglII sites in the MCS.

Transfections

The cells were transfected with h-5HT2aR/EGFP construct. One day before transfection, 450.000 cells (HEK293) were plated in 35 mm dishes in growth medium so that cells will be 70-90% confluent at the time of transfection. For each transfection sample, complexes were prepared as follows:

1 γ/λ DNA (5-HT2a receptor conjugated to EGFP) was added to 80 μl of growth medium without serum and antibiotics.

4 μl of Lipofectamine™ 2000 was added to 80 μl of growth medium without serum and antibiotics.

The diluted DNA was combined with diluted Lipofectamine™ 2000, mixed gently and incubated for 45 minutes at room temperature. Then the complexes were added to cells.

Cells were incubated at 37° C. in a CO2 incubator for 18-48 hours prior to testing.

Western Blotting Analysis

Antibodies.

DUOX 1 and 2 proteins were detected with a rabbit polyclonal antibody raised against the peptide sequence ETELTPQRLQC (SEQ ID NO: 174) located inside the first intracellular loop of human DUOX1 (Damiano et al., PlosOne). P-ERK1/2 (sc-7383) and HaRas (sc-520) antibodies were purchased by Santa Cruz; NOX3 (ab81864) and h-5HT2aR antibodies (ab85496) were purchased by Abcam.

Total cells lysates were obtained in RIPA buffer (50 mM Tris-HCl, pH 7.5, NaCl 150 mM, 1% NP40, 0.5% deoxycholate, 0.1% SDS) containing 2.5 mM Na-pyrophosphate, 1 mM β-glycerophosphate, 1 mM NaVO4, 1 mM NaF, 0.5 mM PMSF, and a cocktail of protease inhibitors (Roche, USA). The cells were kept for 15 min at 4° C. and disrupted by repeated aspiration through a 21-gauge needle. Cell lysates were centrifuged for 10 min at 13000 rpm and the pellets were discarded. Fifty micrograms of total proteins were subjected to SDS-PAGE under reducing conditions. After electrophoresis, the proteins were transferred onto a nitrocellulose filter membrane (Bio-Rad Laboratories, UK) with a Trans-Blot Cell (Bio-Rad Laboratories, UK) and transfer buffer containing 25 mM Tris, 192 mM glycine, 20% methanol. Membranes were placed in 5% non-fat milk in phosphate-buffered saline, 0.5% Tween 20 (TBST) at 4° C. for 2 h to block the nonspecific binding sites. Filters were incubated with specific antibodies before being washed three times in TBST and then incubated with a peroxidase-conjugated secondary antibody (Santa Cruz). After washing with TBST, peroxidase activity was detected with the ECL system (GE-Healthcare, UK).

The filters were also probed with an anti α-tubulin antibody (Sigma, USA). Protein bands were revealed by ECL and, when specified, quantified by densitometry using ImageJ software. Densitometric values were normalized to α-tubulin.

Since, depending on the cell type or tissue, bands of different sizes can appear by Western blotting for 5HT2aR (fragments or protein complexes), to determine which bands are specific, before proceeding with the staining protocol, the antibody was incubated with an excess of peptide that correspond to the epitope recognized by the antibody. By comparing the staining from the blocking antibody vs the antibody alone it has been possible to evidence the specific 5HT2aR staining.

Peptide Synthesis and Screening Assays

The linear and CLIPS peptides are synthesized based on the amino acid sequence of the target protein using standard Fmoc-chemistry and deprotected using trifluoric acid with scavengers. The constrained peptides are synthesized on chemical scaffolds in order to reconstruct conformational epitopes, using Chemically Linked Peptides on Scaffolds (CLIPS) technology (Timmerman et al. (2007). For example, the single looped peptides are synthesized containing a dicysteine, which was cyclized by treating with alpha, alpha'-dibromoxylene and the size of the loop is varied by introducing cysteine residues at variable spacing. If other cysteines besides the newly introduced cysteines are present, they are replaced by alanine. The side-chains of the multiple cysteines in the peptides are coupled to CLIPS templates by reacting onto credit-card format polypropylene PEPSCAN cards (455 peptide formats/card) with a 0.5 mM solution of CLIPS template such as 1,3-bis (bromomethyl) benzene in ammonium bicarbonate (20 mM, pH 7.9)/acetonitrile (1:1(v/v)). The cards are gently shaken in the solution for 30 to 60 minutes while completely covered in solution. Finally, the cards are washed extensively with excess of $H_2O$ and sonicated in distrupt-buffer containing 1 percent SDS/0.1 percent beta-mercaptoethanol in PBS (pH 7.2) at 70° C. for 30 minutes, followed by sonication in $H_2O$ for another 45 minutes.

The binding of antibody to each peptide is tested in a PEPSCAN-based ELISA. The 455-well credit card format polypropylene cards containing the covalently linked peptides are incubated with primary antibody solution for example consisting of 1/1000 diluted serum in blocking solution, for example 4% horse serum, 5% ovalbumin (w/v) in PBS/1% Tween. After washing, the peptides are incubated with a 1/1000 dilution of antibody peroxidase conjugate for one hour at 25° C. After washing, the peroxidase substrate 2,2'-azino-di-3-ethylbenzthiazoline sulfonate (ABTS) and 2 microlitres of 3 percent $H_2O_2$ are added. After one hour, the color development are measured. The color development are quantified with a charge coupled device (CCD)-camera and an image processing system (Slootstra et al., 1996).

The raw data are optical values obtained by a CCD-camera calibrated to export absorption values compatible with a standard 96-well plate ELISA-reader. First the CCD-camera makes a picture of the card before peroxidase coloring and then again a picture after the peroxidase coloring. These two pictures are substracted from each other yielding a binding value for each peptide. This data is entered in the Peplab™ database for secure storage and retrieval.

All raw data are provided in an excel file and the full technical report include plots of the binding acitivity to all peptides and a 3D visualization of all epitope candidates identified.

Methods are described in Timmerman et al. (2007). Functional reconstruction and synthetic mimicry of a conformational epitope using CLIPS™ technology). Structural aspects of antibody-antigen interaction revealed through small random peptide libraries (Slootstra et al., 1996).

Co-Culture of Cortical Neurons and OPCs

Primary cultures of cortical OPCs and neurons are prepared as described by Cheli et al. (2015). For OPCs preparation, cerebral hemispheres from 1 day old mice are mechanically dissociated and plated on poly-D-lysine-coated flasks in Dulbecco's modified Eagle's medium and Ham's F12 (1:1 v/v), containing 100 µg/ml gentamicin and supplemented with 4 mg/ml dextrose anhydrous, 3.75 mg/ml HEPES buffer, 2.4 mg/ml sodium bicarbonate and 10% fetal bovine serum (FBS). After 24 h the medium is changed and the cells are grown in DMEM/F12 supplemented with insulin (5 µg/ml), human transferrin (50 µg/ml), sodium selenite (30 nM), D-Biotin (10 mM), 0.1% BSA (Sigma), 1% FBS and 1% horse serum. After 9 days, OPCs are purified from the mixed glial culture by the differential shaking and adhesion procedure and allowed to grow on poly-Dlysine-coated coverslips in culture media plus PDGF (10 ng/ml) and bFGF (10 ng/ml). OPCs are kept in mitogens (PDGF and bFGF) for 2 days and then induced to exit from the cell cycle and differentiate by switching the cells to a mitogen-free medium (mN2).

Cortical neurons are prepared from the brains of 1- to 2-day-old mouse. Brain cortices are isolated and dissociated by digestion with a solution of 0.05% trypsin (Sigma) containing DNase I (0.06%) in Neurobasal medium for 10 min at 37° C. The digestion reaction is stopped with Neurobasal medium containing 10% fetal bovine serum and triturated by repeated passages (20 times) through a 10 ml pipette. The cell suspension is filtered through a sterile cell strainer (70 µm) into a 50 ml centrifuge tube. The cells are pelleted by centrifugation at 200 g for 5 min, and resuspended in Neurobasal medium plus 2% (v/v) B27 supplemented with 0.25 mM GlutaMax I, 0.25 mM glutamine (Invitrogen), and 100 µg/ml gentamicin. High-density cultures ($5 \times 10^5$ cells, ~2500 cells/mm2) are plated onto 20 mm$^2$ tissue culture wells coated with poly-d-lysine. The neurons are kept at 37° C. in 95% air 5% CO2 for 7 days in vitro and used for co-cultures. After 7 days in vitro, cortical neuron cultures consist of neurons essentially free from non-neural cells.

Co-cultures are prepared by the addition of OPCs to the cultures of cortical neurons at a density of $3 \times 10^5$ cells/ml. These cultures are maintained in DMEM/F12, 1% FBS for 7 and 14 days (Cheli et al., 2015).

The neuron-OPC co-colture model allows the evaluation of the myelination stage of mature OL, by confocal microscopy categorizing them in three different stages: (1) cells that only extend processes but do not contact with neurofilaments; (2) cells that establish contact with neurofilaments but do not myelinate; and (3) cells that wrap axons and have at least two internodes connected to the cell body (Barateiro and Fernandes, 2014).

Scratch Assay

MO3-13 cell migration is assessed by in vitro scratch assay, based on the creation of an artificial gap on a confluent cell monolayer. MO3-13 cells are grown in complete medium and when cells reach 70-80% confluence, a wound is made across the cell layer using a cell scraper. Then cultures are washed in complete medium and are allowed to migrate for 24-48 h and the number of cells that moved across the injury line is counted at microscope.

Fluorimetric Measurement of Intracellular $Ca^{2+}$

Intracellular $Ca^{2+}$ levels are measured fluorimetrically using the membrane-permeable $Ca^{2+}$-sensitive dye Fluo-3-AM. Briefly, cells are washed twice with TTS buffer (137 mN NaCl, 2.7 mM KCl, 1.0 mM $MgCl_2$, 1.8 mM $CaCl_2$, 0.2 mM $NaH_2PO_4$, 12 Mm $NaHCO_3$, 5.5 mM glucose, pH 7.4) and incubated with 10 µm Fluo-3-AM and 0.02% pluronic acid for 1 h at room temperature in the dark. Cells are then washed twice with TTS, before adding the substances to be tested and the changes in fluorescence is measured at different time intervals using Fluoroskan Ascent fluorescent plate reader (ThermoElectron Oy, Vantaa, Finland) and data analyzed by Ascent software.

Induction of EAE (Experimental Autoimmune Encephalomyelitis) as Murine Model for Human Multiple Sclerosis Mice will be immunized subcutaneously with 100 ml of emulsified incomplete Freund's adjuvant supplemented with 500 mg of *Mycobacterium tuberculosis* H37Ra (Difco) and 100 mg of MOG35-55, and will receive an intraperitoneal injection of 200 ng of pertussis toxin (List Biological Laboratories) at the time of immunization and 48 hours later. The mice will be observed daily for clinical signs and scored as described (Shi et al., 2011). Mice will be euthanized, and brains and spinal cords will be removed and fixed by immersion with a 10% neutral-buffered formalin solution and decalcified. Fixed tissues will be embedded in paraffin, sectioned, and stained with H&E and serial histological sections will be stained also immunohistochemically to determine the distribution and types of inflammatory cells in the brain and spinal cord and the demyelination. Spinal cord pathology will be assigned by scores with an experienced pathologist as described previously (Shi et al., 2011)

Annexin V/Propidium Iodide Apoptosis Assay $2-4 \times 10^6$ cells are resuspend in 100 µL 1×Annexin V binding buffer. 5 µL Annexin V Alexa Fluor 488 was added to the samples and incubated in the dark for 15 minutes at room temperature. 100 μL of 1×Annexin V binding buffer and 4 μL of PI at final PI concentration of 2 μg/mL are added to each reaction tube.

The samples are incubated in the dark for 15 minutes at room temperature. The cells are washed with 500 μL 1×Annexin V binding buffer. Samples centrifuged at 335×g for 10 minutes and supernatant decanted. Cells are resuspended in 500 μL 1×Annexin V binding buffer and 500 μL 2% formaldehyde to create a 1% formaldehyde (fixative) solution. Tubes are mixed by gentle flicking and fixed on ice for 10 minutes.

The cells are washed with PBS and diluted with RNase A at the final concentration of 50 μg/mL and incubated for 15 min at 37° C. The tubes are centrifuged at 425×g for eight minutes and samples are analyzed by cytofluorimetry.

Statistical Analysis

Statistical differences were evaluated using a Student's t-test for unpaired samples.

Results

IgG from MS Patients Interact with 5Ht2A Receptor

5-HT2aR protein expression in MO3-13 cells was evaluated by indirect immunofluorescence and flow cytometry (FIG. 1A) and by Western blotting analysis (FIG. 1B). As can be shown in the figure, MO3-13 cells express 5Ht2a receptor protein. Since, depending on the cell line, 5Ht2a receptor protein can appear as fragments of the full antigen or a complex containing the antigen, with different molecular weights, inventors performed Western blotting experiments preincubating the primary antibody in the absence or presence of a tow fold excess of immunizing peptide; in the presence of the peptide, the specific bands disappear or are attenuated. As shown by the immunized blocking peptide experiment (FIG. 1B, right panel), in MO3-13 cells the 5HT2aR appears as a double band of 20-30 kD. The PCR analysis of human 5HT2aR (FIG. 1C) shows that MO3-13 cells, and not the human embryonic kidney cell line HEK293, express 5HT2aR mRNA. To evaluate the hypothesis of the presence of IgG directed against 5HT2aR in the serum from MS patients, MO3-13 cells were immunoprecipitated with IgG from Control and MS subjects and then immunoblotted with anti h-5HT2aR antibody. As shown in FIG. 2, Multiple Sclerosis IgG immunoprecipitated 5HT2aR protein demonstrating a direct interaction between serum IgG MS and the receptor protein.

To confirm the direct interaction between IgG MS and 5-HT2AR, we performed flow cytometric surface binding experiments on HEK293 cells transfected in transient with the h-5HT2aR/EGFP construct. Neither the IgG from control subjects (IgN), nor those from MS patients (IgG MS) significantly bound to the surface of mock transfected cells (FIG. 3, upper panel). In cells transfected with h-5HT2aR/EGFP construct (lower panel), the binding of IgG to transfected cells, calculated on GFP positive cell population, was 26% for IgN, and 77% for IgMS. This experiment indicates, therefore, the existence of a specific binding of the IgG MS at the cell surface of the HEK293 cells transfected with 5HT2aR.

NOX3 Interacts with 5HT2aR

As shown in FIG. 4, MO3-13 cells express the NOX enzyme family members NOX3 and NOX5 isoforms (FIG. 4A).

The inventors focused their attention on NOX3 since this isoform shows a higher percentage of identity (58.8) with NOX2 than NOX5 (32.6%). NOX2 is expressed in oligodendrocytes in vivo (Cavaliere et al., 2013). In particular, NOX3 extracellular domains show a certain degree of identity with NOX2 extracellular domains. This is not the case for NOX5.

The inventors first evaluated whether NOX3 directly interacts with 5HT2aR by immunoprecipitation of cell extract with anti h-NOX3 antibody followed by Western blotting with anti h-5HT2aR antibody. As shown in FIG. 4B, anti NOX3 antibodies immunoprecipitated 5HT2aR protein. The receptor staining was significantly decreased in the immunodepleted sample.

IgG from MS Patients Interact with NOX3

The inventors further evaluated whether IgG from MS patients interact with NOX3 in MO3-13 cells. To this aim MO3-13 cells were immunoprecipitated with IgG from Control and MS subjects and then immunoblotted with anti h-NOX3 antibody. As shown in FIG. 5, IgMS immunoprecipitated NOX3 protein demonstrating a direct interaction between serum IgG from MS patients and NOX3.

Overall, our data suggest that IgGs from MS patients bind to 5HT2aR and to NOX3. Since NOX3 binds to 5HT2aR, it is possible that a membrane protein complex constituted by 5HT2aR, NOX3 and the IgGs from MS is present in MO3-13 cells and in vivo.

Precision Epitope Mapping of NOX2 and 5-HT2A Receptor Extracellular Domains with the Serum from Multiple Sclerosis Affected Patients Approximately 1250 different peptides including linear and CLIPS peptides have been designed and synthesize based on NOX2 heavy chain amino acid sequence (SEQ ID 1) and other 1250 peptides were designed and synthesize based on the human 5-HT2A receptor amino acid sequence (SEQ ID 2). In particular, in both cases, only the extracellular domains of the proteins have been used for the design of the two peptide libraries. For NOX2 were selected the regions 30-48 (SEQ ID 3), 124-169 (SEQ ID 4) and 222-261 (SEQ ID 5) while for 5-HT2Ar were selected the regions 1-76 (SEQ ID 6), 133-148 (SEQ ID 7), 215-233 (SEQ ID 8), 347-362 (SEQ ID 9).

| Sequence ID |
| --- |
| SEQ ID 1: >sp\|P04839\|CY24B_HUMAN Cytochrome b-245 heavy chain OS = Homo sapiens GN = CYBB PE = 1 SV = 2 (NOX2)<br>MGNWAVNEGLSIFVILVWLGLNVFLFVWYYRVYDIPPKFFYTRKLLGSAL<br>ALARAPAACLNFNCMLILLPVCRNLLSFLRGSSACCSTRVRRQLDRNLTF<br>HKMVAWMIALHSAIHTIAHLFNVEWCVNARVNNSDPYSVALSELGDRQNE<br>SYLNFARKRIKNPEGGLYLAVTLLAGITGVVITLCLILIITSSTKTIRRS<br>YFEVFWYTHHLFVIFFIGLAIHGAERIVRGQTAESLAVHNITVCEQKISE<br>WGKIKECPIPQFAGNPPMTWKWIVGPMFLYLCERLVRFWRSQQKVVITKV<br>VTHPFKTIELQMKKKGFKMEVGQYIFVKCPKVSKLEWHPFTLTSAPEEDF<br>FSIHIRIVGDWTEGLFNACGCDKQEFQDAWKLPKIAVDGPFGTASEDVFS<br>YEVVMLVGAGIGVTPFASILKSVWYKYCNNATNLKLKKIYFYWLCRDTHA<br>FEWFADLLQLLESQMQERNNAGFLSYNIYLTGWDESQANHFAVHHDEEKD<br>VITGLKQKTLYGRPNWDNEFKTIASQHPNTRIGVFLCGPEALAETLSKQS<br>ISNSESGPRGVHFIFNKENF |
| SEQ ID 2: >sp\|P28223\|5HT2A_HUMAN 5-hydroxy-tryptamine receptor 2A OS = Homo sapiens GN = HTR2A PE = 1 SV = 2<br>MDILCEENTSLSSTTNSLMQLNDDTRLYSNDFNSGEANTSDAFNWTVDSE<br>NRTNLSCEGCLSPSCLSLLHLQEKNWSALLTAVVIILTIAGNILVIMAVS<br>LEKKLQNATNYFLMSLAIADMLLGFLVMPVSMLTILYGYRWPLPSKLCAV<br>WIYLDVLFSTASIMHLCAISLDRYVAIQNPIHHSRFNSRTKAFLKIIAVW<br>TISVGISMPIPVFGLQDDSKVFKEGSCLLADDNFVLIGSFVSFFIPLTIM<br>VITYFLTIKSLQKEATLCVSDLGTRAKLASFSFLPQSSLSSEKLFQRSIH<br>REPGSYTGRRTMQSISNEQKACKVLGIVFFLFVVMWCPFFITNIMAVICK<br>ESCNEDVIGALLNVFVWIGYLSSAVNPLVYTLFNKTYRSAFSRYIQCQYK<br>ENKKPLQLILVNTIPALAYKSSQLQMGQKKNSKQDAKTTDNDCSMVALGK<br>QHSEEASKDNSDGVNEKVSCV |

| Sequence ID |
| --- |
| SEQ ID 3: CY (NOX2) Loop 1:<br>YRVYDIPPKFFYTRKLLGS |
| SEQ ID 4: CY (NOX2) Loop 2:<br>EWCVNARVNNSDPYSVALSELGDRQNESYLNFARKRIKNPEGGLYL |
| SEQ ID 5: CY (NOX2) Loop 3:<br>HGAERIVRGQTAESLAVHNITVCEQKISEWGKIKECPIPQ |
| SEQ ID 6: N-terminal of 5HT2aR: 1-76 (76 aa)<br>MDILCEENTSLSSTTNSLMQLNDDTRLYSNDFNSGEANTSDAFNWTVDSE<br>NRTNLSCEGCLSPSCLSLLHLQEKNW |
| SEQ ID 7: Loop 1 of 5HT2aR: 133-148 (16 aa)<br>LTILYGYRWPLPSKLC |
| SEQ ID 8: Loop 2 of 5HT2aR: 215-233 (19 aa)<br>LQDDSKVFKEGSCLLADDN |
| SEQ ID 9: Loop 3 of 5HT2aR: 347-362 (16 aa)<br>VICKESCNEDVIGALL |

All peptides have been synthesized in a peptide array format and the binding of 20 different sera to all peptide libraries were measured in an ELISA based set up following the procedure described in detail in the method section "Peptide synthesis and screening assays". In particular 2 sets of experiments were performed on the 2 libraries by using 2 different dilutions of the human patients sera. In the first set of experiment the 20 sera were used at 1:2500 dilutions, while in the second experiment the dilution of the sera was 1:1000. The binding of the different sera to all peptides was quantified and analyzed in detail (Tables 1 and 2, FIGS. 15A, B, C, D and FIGS. 16A and 16B).

TABLE 1

List of peptide sequences from 5HT2A receptor library that are significantly recognized by the MS sera (n = 9) compared to CTRLs (n = 10) (p < 0.05).

|  | Peptide Sequence | SEQ ID |  |
| --- | --- | --- | --- |
| 1 | CNSLMQLNDDTRLYCMDILSEENTSLSSC | SEQ ID NO: 10 | HTR.MAT |
| 2 | CLTILYGYRWPLPSCMDILSEENTSLSSC | SEQ ID NO: 11 | HTR.MAT |
| 3 | LTILYGYRWPAASKL | SEQ ID NO: 12 | HTR.LIN15AA |
| 4 | CLYGYRWPLPSKLSCMDILSEENTSLSSC | SEQ ID NO: 13 | HTR.MAT |
| 5 | YRWPLPSKL | SEQ ID NO: 14 | HTR.LIN9 |
| 6 | CNSLMQLNDDTRLYCLSSEGSLSPSSLSC | SEQ ID NO: 15 | HTR.MAT |
| 7 | CLQDDSKVFKEGSSCMDILSEENTSLSSC | SEQ ID NO: 16 | HTR.MAT |
| 8 | LTILYGYRWPLPSKL | SEQ ID NO: 17 | HTR.LIN15AA |
| 9 | CMQLNDDTRLYSNDCMDILSEENTSLSSC | SEQ ID NO: 18 | HTR.MAT |
| 10 | CLSPSSLSLLHLQECMDILSEENTSLSSC | SEQ ID NO: 19 | HTR.MAT |
| 11 | CSTTNSLMQLNDDTCMDILSEENTSLSSC | SEQ ID NO: 20 | HTR.MAT |
| 12 | CLTILYGYRWPLPSCKESSNEDVIGALLC | SEQ ID NO: 21 | HTR.MAT |
| 13 | CTVDSENRTNLSSECMDILSEENTSLSSC | SEQ ID NO: 22 | HTR.MAT |
| 14 | GYRWPLPSK | SEQ ID NO: 23 | HTR.LIN9 |
| 15 | CMQLNDDTRLYSNDCSGEANTSDAFNWTC | SEQ ID NO: 24 | HTR.MAT |
| 16 | CDSKVFKEGSSLLACKESSNEDVIGALLC | SEQ ID NO: 25 | HTR.MAT |
| 17 | CENTSLSSTTNSLMCMDILSEENTSLSSC | SEQ ID NO: 26 | HTR.MAT |
| 18 | CSLSSTTNSLMQLNCMDILSEENTSLSSC | SEQ ID NO: 27 | HTR.MAT |
| 19 | CNSLMQLNDTRLYCSGEANTSDAFNWTC | SEQ ID NO: 28 | HTR.MAT |
| 20 | CLYGYRWPLPSKLSCKESSNEDVIGALLC | SEQ ID NO: 29 | HTR.MAT |
| 21 | CMDILSEENTSLSSCMQLNDDTRLYSNDC | SEQ ID NO: 30 | HTR.MAT |
| 22 | CSDAFNWTVDSENRCMDILSEENTSLSSC | SEQ ID NO: 31 | HTR.MAT |
| 23 | TVDSENRTNLAAEGC | SEQ ID NO: 32 | HTR.LIN15AA |
| 24 | CNDDTRLYSNDFNSCMDILSEENTSLSSC | SEQ ID NO: 33 | HTR.MAT |
| 25 | CTVDSENRTNLSSECRTNLSSEGSLSPSC | SEQ ID NO: 34 | HTR.MAT |

TABLE 1-continued

List of peptide sequences from 5HT2A receptor library that are significantly recognized by the MS sera (n = 9) compared to CTRLs (n = 10) (p < 0.05).

| # | Sequence | SEQ ID NO | Source |
|---|---|---|---|
| 26 | CLSSEGSLSPSSLSCMDILSEENTSLSSC | SEQ ID NO: 35 | HTR.MAT |
| 27 | CLSPSSLSLLHLQECTVDSENRTNLSSEC | SEQ ID NO: 36 | HTR.MAT |
| 28 | CDSKVFKEGSSLLACMDILSEENTSLSSC | SEQ ID NO: 37 | HTR.MAT |
| 29 | TILYGYRWPLPSKLC | SEQ ID NO: 38 | HTR.LIN15AA |
| 30 | CFNWTVDSENRTNLCMDILSEENTSLSSC | SEQ ID NO: 39 | HTR.MAT |
| 31 | STTNSLMQLNAATRL | SEQ ID NO: 40 | HTR.LIN15AA |
| 32 | CLYGYRWPLPSKLSCYSNDFNSGEANTSC | SEQ ID NO: 41 | HTR.MAT |
| 33 | QDDSKVFKEGAALLA | SEQ ID NO: 42 | HTR.LIN15AA |
| 34 | CNSLMQLNDDTRLYCYSNDFNSGEANTSC | SEQ ID NO: 43 | HTR.MAT |
| 35 | CLTILYGYRWPLPSKLC | SEQ ID NO: 44 | HTR.P2_15AA |
| 36 | CLYGYRWPLPSKLSCSDAFNWTVDSENRC | SEQ ID NO: 45 | HTR.MAT |
| 37 | CDSKVFKEGSSLLACSGEANTSDAFNWTC | SEQ ID NO: 46 | HTR.MAT |
| 38 | CVFKEGSSLLADDNCKESSNEDVIGALLC | SEQ ID NO: 47 | HTR.MAT |
| 39 | CLSEENTSLSSTTNCMDILSEENTSLSSC | SEQ ID NO: 48 | HTR.MAT |
| 40 | CLTILYGYRWPLPSCLYGYRWPLPSKLSC | SEQ ID NO: 49 | HTR.MAT |
| 41 | CLTILYGYRWPAASKLC | SEQ ID NO: 50 | HTR.P2_15AA |
| 42 | CTRLYSNDFNSGEACKESSNEDVIGALLC | SEQ ID NO: 51 | HTR.MAT |
| 43 | CLYGYRWPLPSKLSCSGEANTSDAFNWTC | SEQ ID NO: 52 | HTR.MAT |
| 44 | CMDILSEENTSLSSCSKESSNEDVIGALC | SEQ ID NO: 53 | HTR.MAT |
| 45 | CSSLSLLHLQEKNWCMDILSEENTSLSSC | SEQ ID NO: 54 | HTR.MAT |
| 46 | CDSKVFKEGSSLLACSENRTNLSSEGSLC | SEQ ID NO: 55 | HTR.MAT |
| 47 | CVFKEGSSLLADDNCSDAFNWTVDSENRC | SEQ ID NO: 56 | HTR.MAT |
| 48 | CLQDDSKVFKEGSSCKESSNEDVIGALLC | SEQ ID NO: 57 | HTR.MAT |

| | Peptide Sequence | MEAN MS | SEM MS | MEAN CTRL | SEM CTRL | P-value |
|---|---|---|---|---|---|---|
| 1 | CNSLMQLNDDTRLYCMDILSEENTSLSSC (SEQ ID NO: 10) | 445.78 | 64.60 | 252.10 | 39.78 | 0.01823 |
| 2 | CLTILYGYRWPLPSCMDILSEENTSLSSC (SEQ ID NO: 11) | 421.56 | 68.75 | 228.85 | 35.30 | 0.01984 |
| 3 | LTILYGYRWPAASKL (SEQ ID NO: 12) | 653.28 | 125.82 | 322.35 | 46.78 | 0.01994 |
| 4 | CLYGYRWPLPSKLSCMDILSEENTSLSSC (SEQ ID NO: 13) | 449.78 | 75.33 | 246.80 | 41.88 | 0.02701 |
| 5 | YRWPLPSKL (SEQ ID NO: 14) | 566.00 | 113.14 | 285.70 | 42.28 | 0.02714 |
| 6 | CNSLMQLNDDTRLYCLSSEGSLSPSSLSC (SEQ ID NO: 15) | 418.89 | 63.39 | 249.55 | 36.07 | 0.02908 |
| 7 | CLQDDSKVFKEGSSCMDILSEENTSLSSC (SEQ ID NO: 16) | 434.67 | 78.17 | 233.80 | 39.09 | 0.02977 |
| 8 | LTILYGYRWPLPSKL (SEQ ID NO: 17) | 647.17 | 123.46 | 340.05 | 54.05 | 0.03031 |
| 9 | CMQLNDDTRLYSNDCMDILSEENTSLSSC (SEQ ID NO: 18) | 379.67 | 62.21 | 212.40 | 38.38 | 0.03169 |
| 10 | CLSPSSLSLLHLQECMDILSEENTSLSSC (SEQ ID NO: 19) | 305.00 | 47.33 | 183.45 | 25.89 | 0.03322 |

TABLE 1-continued

List of peptide sequences from 5HT2A receptor library that are significantly recognized by the MS sera (n = 9) compared to CTRLs (n = 10) (p < 0.05).

| | | | | | | |
|---|---|---|---|---|---|---|
| 11 | CSTTNSLMQLNDDTCMDILSEENTSLSSC (SEQ ID NO: 20) | 321.28 | 53.13 | 186.85 | 29.61 | 0.03644 |
| 12 | CLTILYGRWPLPSCKESSNEDVIGALLC (SEQ ID NO: 21) | 629.14 | 113.96 | 350.93 | 55.40 | 0.03662 |
| 13 | CTVDSENRTNLSSECMDILSEENTSLSSC (SEQ ID NO: 22) | 300.11 | 59.60 | 160.80 | 24.09 | 0.03779 |
| 14 | GYRWPLPSK (SEQ ID NO: 23) | 623.00 | 129.12 | 322.80 | 51.78 | 0.03847 |
| 15 | CMQLNDDTRLYSNDCSGEANTSDAFNWTC (SEQ ID NO: 24) | 497.78 | 104.53 | 257.25 | 39.91 | 0.03889 |
| 16 | CDSKVFKEGSSLLACKESSNEDVIGALLC (SEQ ID NO: 25) | 604.03 | 102.90 | 347.50 | 57.46 | 0.03901 |
| 17 | CENTSLSSTTNSLMCMDILSEENTSLSSC (SEQ ID NO: 26) | 316.22 | 59.29 | 175.00 | 27.76 | 0.03938 |
| 18 | CSLSSTTNSLMQLNCMDILSEENTSLSSC (SEQ ID NO: 27) | 323.72 | 56.11 | 188.90 | 27.71 | 0.03996 |
| 19 | CNSLMQLNDTRzLYCSGEANTSDAFNWTC (SEQ ID NO: 28) | 564.11 | 112.62 | 299.55 | 51.82 | 0.04118 |
| 20 | CLYGYRWPLPSKLSCKESSNEDVIGALLC (SEQ ID NO: 29) | 689.03 | 123.08 | 390.93 | 64.64 | 0.04121 |
| 21 | CM DILSEENTSLSSCMQLNDDTRLYSNDC (SEQ ID NO: 30) | 392.28 | 70.22 | 223.85 | 36.73 | 0.04279 |
| 22 | CSDAFNWTVDSENRCMDILSEENTSLSSC (SEQ ID NO: 31) | 394.00 | 81.52 | 207.20 | 34.73 | 0.04293 |
| 23 | TVDSENRTNLAAEGC (SEQ ID NO: 32) | 587.33 | 95.96 | 348.10 | 58.23 | 0.04345 |
| 24 | CNDDTRLYSNDFNSCMDILSEENTSLSSC (SEQ ID NO: 33) | 350.67 | 67.59 | 196.45 | 28.93 | 0.04389 |
| 25 | CTVDSENRTNLSSECRTNLSSEGSLSPSC (SEQ ID NO: 34) | 507.22 | 85.61 | 296.95 | 50.10 | 0.04415 |
| 26 | CLSSEGSLSPSSLSCMDILSEENTSLSSC (SEQ ID NO: 35) | 320.72 | 57.25 | 188.85 | 26.70 | 0.04533 |
| 27 | CLSPSSLSLLHLQECTVDSENRTNLSSEC (SEQ ID NO: 36) | 427.89 | 65.71 | 263.00 | 41.97 | 0.04538 |
| 28 | CDSKVFKEGSSLLACMDILSEENTSLSSC (SEQ ID NO: 37) | 429.00 | 84.12 | 236.60 | 38.29 | 0.04573 |
| 29 | TILYGYRWPLPSKLC (SEQ ID NO: 38) | 651.50 | 115.23 | 378.20 | 61.96 | 0.04627 |
| 30 | CFNWTVDSENRTNLCMDILSEENTSLSSC (SEQ ID NO: 39) | 312.00 | 61.58 | 174.90 | 25.14 | 0.04697 |
| 31 | STTNSLMQLNAATRL (SEQ ID NO: 40) | 611.83 | 91.02 | 385.15 | 58.43 | 0.04718 |
| 32 | CLYGYRWPLPSKLSCYSNDFNSGEANTSC (SEQ ID NO: 41) | 555.67 | 120.54 | 288.50 | 48.26 | 0.04721 |
| 33 | QDDSKVFKEGAALLA (SEQ ID NO: 42) | 439.11 | 71.77 | 263.70 | 43.61 | 0.04734 |
| 34 | CNSLMQLNDDTRLYCYSNDFNSGEANTSC (SEQ ID NO: 43) | 459.72 | 91.78 | 268.10 | 43.39 | 0.04736 |
| 35 | CLTILYGYRWPLPSKLC (SEQ ID NO: 44) | 792.94 | 137.92 | 475.00 | 68.01 | 0.04762 |
| 36 | CLYGYRWPLPSKLSCSDAFNWTVDSENRC (SEQ ID NO: 45) | 511.11 | 90.49 | 298.55 | 48.45 | 0.04794 |
| 37 | CDSKVFKEGSSLLACSGEANTSDAFNWTC (SEQ ID NO: 46) | 623.06 | 127.57 | 333.75 | 59.05 | 0.04808 |
| 38 | CVFKEGSSLLADDNCKESSNEDVIGALLC (SEQ ID NO: 47) | 594.61 | 105.51 | 348.13 | 55.91 | 0.04850 |

TABLE 1-continued

List of peptide sequences from 5HT2A receptor library that are significantly
recognized by the MS sera (n = 9) compared to CTRLs (n = 10) (p < 0.05).

| # | Sequence | | | | | |
|---|---|---|---|---|---|---|
| 39 | CLSEENTSLSSTTNCMDILSEENTSLSSC (SEQ ID NO: 48) | 303.50 | 51.61 | 184.40 | 26.46 | 0.04929 |
| 40 | CLTILYGYRWPLPSCLYGYRWPLPSKLSC (SEQ ID NO: 49) | 879.72 | 160.75 | 508.45 | 83.43 | 0.04973 |
| 41 | CLTILYGYRWPAASKLC (SEQ ID NO: 50) | 782.33 | 149.17 | 449.80 | 66.54 | 0.05001 |
| 42 | CTRLYSNDFNSGEACKESSNEDVIGALLC (SEQ ID NO: 51) | 561.03 | 100.74 | 333.60 | 47.96 | 0.05023 |
| 43 | CLYGYRWPLPSKLSCSGEANTSDAFNWTC (SEQ ID NO: 52) | 649.67 | 137.64 | 344.80 | 60.02 | 0.05041 |
| 44 | CM DI LSEE NTSLSS-CSKESSNE DV IGALC (SEQ ID NO: 53) | 432.33 | 68.96 | 266.55 | 41.79 | 0.05050 |
| 45 | CSSLSLLHLQEKNWCMDILSEENTSLSSC (SEQ ID NO: 54) | 318.17 | 49.59 | 198.50 | 30.50 | 0.05066 |
| 46 | CDSKVFKEGSSLLACSENRTNLSSEGSLC (SEQ ID NO: 55) | 512.94 | 90.33 | 296.70 | 54.19 | 0.05072 |
| 47 | CVFKEGSSLLADDNCSDAFNWTVDSENRC (SEQ ID NO: 56) | 399.89 | 65.84 | 244.50 | 37.80 | 0.05093 |
| 48 | CLQDDSKVFKEGSSCKESSNEDVIGALLC (SEQ ID NO: 57) | 632.28 | 111.59 | 373.15 | 61.16 | 0.051561 |

HTR.MAT: double looped conformational peptide, HTR.LIN15AA: linear peptide of 15 amino acids, HTR.LIN9:
linear peptide of 9 amino acids, HTR.P2_15AA: single looped conformational peptide of 15 amino acids.

In double looped peptides, three cysteine residues were added, two as first and last amino acid and one in the middle of the sequence. Then peptides of the invention may the whole sequence or the fragments located between two cysteine residues or the sequence with only one cysteine at either end of the sequence. In single looped peptides, two cysteine residues were added, as first and last amino acid. Then peptides of the invention may the whole sequence or the fragment located between two cysteine residues or the sequence with only one cysteine at either end of the sequence.

TABLE 2

List of peptide sequences from NOX2 library that are significantly recognized by the
MS sera (n = 9) compared to CTRLs (n = 10) (p < 0.05).

| # | Peptide Sequence | SEQ ID NO: | |
|---|---|---|---|
| 1 | NFARKRIKN | SEQ ID NO: 58 | CB245.LIN9 |
| 2 | LNFARKRIK | SEQ ID NO: 59 | CB245.LIN9 |
| 3 | CNFARKRIKNC | SEQ ID NO: 60 | CB245.P2_9 |
| 4 | CSYLNFARKRIKNPEGCQNESYLNFARKRIKNC | SEQ ID NO: 61 | CB245.MAT |
| 5 | NESYLNFARKAAKNP | SEQ ID NO: 62 | CB245.LIN15AA |
| 6 | QNESYLNFARKRIKN | SEQ ID NO: 63 | CB245.LIN15AA |
| 7 | CVSEQKISEWGKIKESCQNESYLNFARKRIKNC | SEQ ID NO: 64 | CB245.MAT |
| 8 | CNFARKRIKNPEGGLYCQNESYLNFARKRIKNC | SEQ ID NO: 65 | CB245.MAT |
| 9 | CVRGQTAESLAVHNITCQNESYLNFARKRIKNC | SEQ ID NO: 66 | CB245.MAT |
| 10 | FARKRIKNP | SEQ ID NO: 67 | CB245.LIN9 |
| 11 | GDRQNESYLNAGRKR | SEQ ID NO: 68 | CB245.LIN15AA |
| 12 | CQKISEWGKIKESPIPCQNESYLNFARKRIKNC | SEQ ID NO: 69 | CB245.MAT |
| 13 | CGDRQNESYLNFARKRCQNESYLNFARKRIKNC | SEQ ID NO: 70 | CB245.MAT |

TABLE 2-continued

List of peptide sequences from NOX2 library that are significantly recognized by the MS sera (n = 9) compared to CTRLs (n = 10) (p < 0.05).

| | | | |
|---|---|---|---|
| 14 | SYLNFARKRIAAPEG | SEQ ID NO: 71 | CB245.LIN15AA |
| 15 | CEWSVNARVNNSDPYSCPYSVALSELGDRQNEC | SEQ ID NO: 72 | CB245.MAT |
| 16 | CHGAERIVRGQTAESLCQNESYLNFARKRIKNC | SEQ ID NO: 73 | CB245.MAT |
| 17 | CESLAVHNITVSEQKICQNESYLNFARKRIKNC | SEQ ID NO: 74 | CB245.MAT |
| 18 | CERIVRGQTAESLAVHCQNESYLNFARKRIKNC | SEQ ID NO: 75 | CB245.MAT |
| 19 | RQNESYLNFARKRIK | SEQ ID NO: 76 | CB245.LIN15AA |
| 20 | NFARKRIKNPAAGLY | SEQ ID NO: 77 | CB245.LIN15AA |
| 21 | DPYSVALSELAARQN | SEQ ID NO: 78 | CB245.LIN15AA |
| 22 | CESLAVHNITVSEQKICSYLNFARKRIKNPEGC | SEQ ID NO: 79 | CB245.MAT |
| 23 | CSELGDRQNESYLNFACQNESYLNFARKRIKNC | SEQ ID NO: 80 | CB245.MAT |
| 24 | CNITVSEQKISEWGKICQNESYLNFARKRIKNC | SEQ ID NO: 81 | CB245.MAT |
| 25 | CHGAERIVRGQTAESLCSYLNFARKRIKNPEGC | SEQ ID NO: 82 | CB245.MAT |
| 26 | KISEWGKIK | SEQ ID NO: 83 | CB245.LIN9 |
| 27 | CVSEQKISEWGKIKESCEQKISEWGKIKESPIC | SEQ ID NO: 84 | CB245.MAT |
| 28 | CGDRQNESYLNFARKRCGDRQNESYLNFARKRC | SEQ ID NO: 85 | CB245.MAT |
| 29 | CNESYLNFARKAAKNPC | SEQ ID NO: 86 | CB245.P2_15AA |
| 30 | CLNFARKRIKC | SEQ ID NO: 87 | CB245.P2_9 |
| 31 | QKISEWGKIKAAPIP | SEQ ID NO: 88 | CB245.LIN15AA |
| 32 | CHGAERIVRGQTAESLCNFARKRIKNPEGGLYC | SEQ ID NO: 89 | CB245.MAT |
| 33 | CQNESYLNFARKRIKNC | SEQ ID NO: 90 | CB245.P2_15AA |
| 34 | LNFARKRIKNAAGGL | SEQ ID NO: 91 | CB245.LIN15AA |
| 35 | CLNFARKRIKNAAGGLC | SEQ ID NO: 92 | CB245.P2_15AA |
| 36 | CQKISEWGKIKESPIPCTVSEQKISEWGKIKEC | SEQ ID NO: 93 | CB245.MAT |
| 37 | TVCEQKISEWGKIKE | SEQ ID NO: 94 | CB245.LIN15AA |
| 38 | CRQNESYLNFARKRIKC | SEQ ID NO: 95 | CB245.P2_15AA |
| 39 | NITVCEQKISAAGKI | SEQ ID NO: 96 | CB245.LIN15AA |
| 40 | CNFARKRIKNPEGGLYCSYLNFARKRIKNPEGC | SEQ ID NO: 97 | CB245.MAT |
| 41 | CQKISEWGKIKESPIPCVSEQKISEWGKIKESC | SEQ ID NO: 98 | CB245.MAT |
| 42 | CNITVSEQKISEWGKICSYLNFARKRIKNPEGC | SEQ ID NO: 99 | CB245.MAT |
| 43 | CQTAESLAVHNITVSECQNESYLNFARKRIKNC | SEQ ID NO: 100 | CB245.MAT |
| 44 | CHGAERIVRGQTAESLCQKISEWGKIKESPIPC | SEQ ID NO: 101 | CB245.MAT |
| 45 | GKIKECPIP | SEQ ID NO: 102 | CB245.LIN9 |
| 46 | CEWSVNARVNNSDPYSCQNESYLNFARKRIKNC | SEQ ID NO: 103 | CB245.MAT |
| 47 | LGDRQNESYLNFARK | SEQ ID NO: 104 | CB245.LIN15AA |
| 48 | CNITVSEQKISAAGKIC | SEQ ID NO: 105 | CB245.P2_15AA |
| 49 | CNFARKRIKNPEGGLYCSLAVHNITVSEQKISC | SEQ ID NO: 106 | CB245.MAT |
| 50 | ESYLNFARK | SEQ ID NO: 107 | CB245.LIN9 |
| 51 | CKISEWGKIKC | SEQ ID NO: 108 | CB245.P2_9 |

TABLE 2-continued

List of peptide sequences from NOX2 library that are significantly recognized by the MS sera (n = 9) compared to CTRLs (n = 10)(p < 0.05).

| 52 | NESYLNFARKRIKNP | SEQ ID NO: 109 | CB245.LIN15AA |
| --- | --- | --- | --- |
| 53 | CVALSELGDRQNESYLCQNESYLNFARKRIKNC | SEQ ID NO: 110 | CB245.MAT |
| 54 | CQNESYLNFARKRIKNCVSEQKISEWGKIKESC | SEQ ID NO: 111 | CB245.MAT |
| 55 | CVSEQKISEWGKIKESCGDRQNESYLNFARKRC | SEQ ID NO: 112 | CB245.MAT |
| 56 | QNESYLNFARAAIKN | SEQ ID NO: 113 | CB245.LIN15AA |
| 57 | CSEQKISEWGKIKESPC | SEQ ID NO: 114 | CB245.P2_15AA |
| 58 | CVSEQKISEWGKIKESCVSEQKISEWGKIKESC | SEQ ID NO: 115 | CB245.MAT |
| 59 | WGKIKECPI | SEQ ID NO: 116 | CB245.LIN9 |
| 60 | CNFARKRIKNPEGGLYCGDRQNESYLNFARKRC | SEQ ID NO: 117 | CB245.MAT |
| 61 | VNARVNNSDPAAVAL | SEQ ID NO: 118 | CB245.LIN15AA |
| 62 | YLNFARKRIKAAEGG | SEQ ID NO: 119 | CB245.LIN15AA |
| 63 | GDRQNESYLNFARKR | SEQ ID NO: 120 | CB245.LIN15AA |
| 64 | WCVNARVNNSDPYSV | SEQ ID NO: 121 | CB245.LIN15AA |
| 65 | CSYLNFARKRIKNPEGCITVSEQKISEWGKIKC | SEQ ID NO: 122 | CB245.MAT |
| 66 | CAVHNITVSEQKISEWCVSEQKISEWGKIKESC | SEQ ID NO: 123 | CB245.MAT |
| 67 | CPYSVALSELGDRQNECITVSEQKISEWGKIKC | SEQ ID NO: 124 | CB245.MAT |
| 68 | CSYLNFARKRIKNPEGCGDRQNESYLNFARKRC | SEQ ID NO: 125 | CB245.MAT |
| 69 | CAVHNITVSEQKISEWCQNESYLNFARKRIKNC | SEQ ID NO: 126 | CB245.MAT |
| 70 | LGDRQNESYLAAARK | SEQ ID NO: 127 | CB245.LIN15AA |
| 71 | CVNARVNNSDPYSVALCVSEQKISEWGKIKESC | SEQ ID NO: 128 | CB245.MAT |
| 72 | CFNVEWSVNARVNNSDCGDRQNESYLNFARKRC | SEQ ID NO: 129 | CB245.MAT |
| 73 | CNSDPYSVALSELGDRCVSEQKISEWGKIKESC | SEQ ID NO: 130 | CB245.MAT |
| 74 | CGDRQNESYLNFARKRCSYLNFARKRIKNPEGC | SEQ ID NO: 131 | CB245.MAT |
| 75 | DPYSVALSELGDRQN | SEQ ID NO: 132 | CB245.LIN15AA |
| 76 | CAVHNITVSEQKISEWCSYLNFARKRIKNPEGC | SEQ ID NO: 133 | CB245.MAT |
| 77 | CVRGQTAESLAVHNITCITVSEQKISEWGKIKC | SEQ ID NO: 134 | CB245.MAT |
| 78 | CQNESYLNFARKRIKNCSYLNFARKRIKNPEGC | SEQ ID NO: 135 | CB245.MAT |
| 79 | CESLAVHNITVSEQKICGDRQNESYLNFARKRC | SEQ ID NO: 136 | CB245.MAT |
| 80 | CRVNNSDPYSVALSELCQNESYLNFARKRIKNC | SEQ ID NO: 137 | CB245.MAT |
| 81 | CSYLNFARKRIKNPEGCNFARKRIKNPEGGLYC | SEQ ID NO: 138 | CB245.MAT |
| 82 | CQTAESLAVHNITVSECVSEQKISEWGKIKESC | SEQ ID NO: 139 | CB245.MAT |
| 83 | YLNFARKRI | SEQ ID NO: 140 | CB245.LIN9 |
| 84 | CFNVEWSVNARVNNSDCVSEQKISEWGKIKESC | SEQ ID NO: 141 | CB245.MAT |
| 85 | CVSEQKISEWGKIKESCTVSEQKISEWGKIKEC | SEQ ID NO: 142 | CB245.MAT |
| 86 | CNSDPYSVALSELGDRCITVSEQKISEWGKIKC | SEQ ID NO: 143 | CB245.MAT |
| 87 | CNITVSEQKISEWGKICGDRQNESYLNFARKRC | SEQ ID NO: 144 | CB245.MAT |
| 88 | CLGDRQNESYLAAARKC | SEQ ID NO: 145 | CB245.P2_15AA |
| 89 | QKISEWGKI | SEQ ID NO: 146 | CB245.LIN9 |
| 90 | CITVSEQKISEAAKIKC | SEQ ID NO: 147 | CB245.P2_15AA |

TABLE 2-continued

List of peptide sequences from NOX2 library that are significantly recognized by the MS sera (n = 9) compared to CTRLs (n = 10)(p < 0.05).

| | | | |
|---|---|---|---|
| 91 | CVRGQTAESLAVHNITCVHNITVSEQKISEWGC | SEQ ID NO: 148 | CB245.MAT |
| 92 | CQKISEWGKIKESPIPCVHNITVSEQKISEWGC | SEQ ID NO: 149 | CB245.MAT |
| 93 | CQNESYLNFARKRIKNCNFARKRIKNPEGGLYC | SEQ ID NO: 150 | CB245.MAT |
| 94 | CRVNNSDPYSVALSELCVSEQKISEWGKIKESC | SEQ ID NO: 151 | CB245.MAT |
| 95 | CGDRQNESYLNFARKRCVSEQKISEWGKIKESC | SEQ ID NO: 152 | CB245.MAT |
| 96 | CQKISEWGKIKAAPIPC | SEQ ID NO: 153 | CB245.P2_15AA |
| 97 | CVNARVNNSDPYSVALCTVSEQKISEWGKIKEC | SEQ ID NO: 154 | CB245.MAT |
| 98 | CEWSVNARVNNSDPYSCVSEQKISEWGKIKESC | SEQ ID NO: 155 | CB245.MAT |
| 99 | CVRGQTAESLAVHNITCSLAVHNITVSEQKISC | SEQ ID NO: 156 | CB245.MAT |

| Sequence | MEAN MS | SEM MS | MEAN CTRL | SEM CTRL | P-value |
|---|---|---|---|---|---|
| NFARKRIKN (SEQ ID NO: 58) | 613.833 | 117.974 | 288.95 | 50.127 | 0.017533 |
| LNFARKRIK (SEQ ID NO: 59) | 557.056 | 92.576 | 294.6 | 50.896 | 0.020529 |
| CNFARKRIKNC (SEQ ID NO: 60) | 748.389 | 145.481 | 374.6 | 48.888 | 0.020984 |
| CSYLNFARKRIKNPEGCQNESYLNFARKRIKNC (SEQ ID NO: 61) | 778.278 | 141.548 | 398.9 | 62.496 | 0.021068 |
| NESYLNFARKAAKNP (SEQ ID NO: 62) | 505.278 | 81.335 | 279.1 | 42.463 | 0.021146 |
| QNESYLNFARKRIKN (SEQ ID NO: 63) | 610.778 | 110.062 | 309.65 | 53.910 | 0.021235 |
| CVSEQKISEWGKIKESCQNESYLNFARKRIKNC (SEQ ID NO: 64) | 804.556 | 152.312 | 402.9 | 62.907 | 0.021494 |
| CNFARKRIKNPEGGLYCQNESYLNFARKRIKNC (SEQ ID NO: 65) | 801.056 | 148.456 | 410.85 | 61.525 | 0.021931 |
| CVRGQTAESLAVHNITCQNESYLNFARKRIKNC (SEQ ID NO: 66) | 824.500 | 143.332 | 438.35 | 67.804 | 0.022090 |
| FARKRIKNP (SEQ ID NO: 67) | 666.111 | 125.706 | 337.4 | 54.419 | 0.023461 |
| GDRQNESYLNAGRKR (SEQ ID NO: 68) | 547.278 | 96.746 | 294.2 | 42.636 | 0.023828 |
| CQKISEWGKIKESPIPCQNESYLNFARKRIKNC (SEQ ID NO: 69) | 855.111 | 151.464 | 458.3 | 72.573 | 0.025816 |
| CGDRQNESYLNFARKRCQNESYLNFARKRIKNC (SEQ ID NO: 70) | 831.278 | 163.826 | 412.7 | 72.303 | 0.026839 |
| SYLNFARKRIAAPEG (SEQ ID NO: 71) | 472.000 | 83.677 | 259.75 | 37.175 | 0.027985 |
| CEWSVNARVNNSDPYSCPYSVALSELGDRQNEC (SEQ ID NO: 72) | 428.167 | 79.768 | 225.5 | 35.843 | 0.028038 |
| CHGAERIVRGQTAESLCQNESYLNFARKRIKNC (SEQ ID NO: 73) | 748.111 | 136.357 | 407.2 | 56.805 | 0.028309 |
| CESLAVHNITVSEQKICQNESYLNFARKRIKNC (SEQ ID NO: 74) | 689.556 | 135.802 | 354.9 | 53.509 | 0.028995 |
| CERIVRGQTAESLAVHCQNESYLNFARKRIKNC (SEQ ID NO: 75) | 833.444 | 149.785 | 455.55 | 68.507 | 0.029550 |
| RQNESYLNFARKRIK (SEQ ID NO: 76) | 458.833 | 88.112 | 241.2 | 38.449 | 0.031258 |
| NFARKRIKNPAAGLY (SEQ ID NO: 77) | 604.167 | 112.468 | 323.85 | 51.645 | 0.031431 |
| DPYSVALSELAARQN (SEQ ID NO: 78) | 565.389 | 92.915 | 325.05 | 50.274 | 0.031704 |
| CESLAVHNITVSEQKICSYLNFARKRIKNPEGC (SEQ ID NO: 79) | 639.611 | 114.168 | 357.1 | 51.488 | 0.031924 |

TABLE 2-continued

List of peptide sequences from NOX2 library that are significantly recognized by the MS sera (n = 9) compared to CTRLs (n = 10) (p < 0.05).

| Sequence | | | | | |
|---|---|---|---|---|---|
| CSELGDRQNESYLNFACQNESYLNFARKRIKNC (SEQ ID NO: 80) | 773.167 | 154.146 | 398.9 | 65.715 | 0.033178 |
| CNITVSEQKISEWGKICQNESYLNFARKRIKNC (SEQ ID NO: 81) | 770.889 | 150.182 | 408.8 | 62.723 | 0.033686 |
| CHGAERIVRGQTAESLCSYLNFARKRIKNPEGC (SEQ ID NO: 82) | 755.722 | 135.689 | 417.5 | 66.730 | 0.033710 |
| KISEWGKIK (SEQ ID NO: 83) | 404.500 | 76.258 | 223.9 | 29.152 | 0.034179 |
| CVSEQKISEWGKIKESCEQKISEWGKIKESPIC (SEQ ID NO: 84) | 811.056 | 151.397 | 443.5 | 66.739 | 0.034184 |
| CGDRQNESYLNFARKRCGDRQNESYLNFARKRC (SEQ ID NO: 85) | 775.500 | 157.009 | 404.05 | 61.921 | 0.035130 |
| CNESYLNFARKAAKNPC (SEQ ID NO: 86) | 702.222 | 119.948 | 411.15 | 54.568 | 0.035259 |
| CLNFARKRIKC (SEQ ID NO: 87) | 713.333 | 148.240 | 374.7 | 47.602 | 0.036234 |
| QKISEWGKIKAAPIP (SEQ ID NO: 88) | 701.889 | 142.859 | 364.3 | 59.774 | 0.036968 |
| CHGAERIVRGQTAESLCNFARKRIKNPEGGLYC (SEQ ID NO: 89) | 733.889 | 136.475 | 404.6 | 63.679 | 0.037064 |
| CQNESYLNFARKRIKNC (SEQ ID NO: 90) | 667.389 | 130.810 | 361.75 | 51.543 | 0.037142 |
| LNFARKRIKNAAGGL (SEQ ID NO: 91) | 354.778 | 70.317 | 187.85 | 30.409 | 0.037220 |
| CLNFARKRIKNAAGGLC (SEQ ID NO: 92) | 691.444 | 137.690 | 367 | 57.492 | 0.037383 |
| CQKISEWGKIKESPIPCTVSEQKISEWGKIKEC (SEQ ID NO: 93) | 846.833 | 155.062 | 476.45 | 69.583 | 0.037396 |
| TVCEQKISEWGKIKE (SEQ ID NO: 94) | 514.944 | 89.577 | 289.4 | 50.414 | 0.037701 |
| CRQNESYLNFARKRIKC (SEQ ID NO: 95) | 653.944 | 131.478 | 350.1 | 49.641 | 0.037862 |
| NITVCEQKISAAGKI (SEQ ID NO: 96) | 564.500 | 103.965 | 314.2 | 49.516 | 0.038184 |
| CNFARKRIKNPEGGLYCSYLNFARKRIKNPEGC (SEQ ID NO: 97) | 752.333 | 139.571 | 416.6 | 66.438 | 0.038310 |
| CQKISEWGKIKESPIPCVSEQKISEWGKIKESC (SEQ ID NO: 98) | 815.972 | 154.878 | 450.975 | 66.905 | 0.038417 |
| CNITVSEQKISEWGKICSYLNFARKRIKNPEGC (SEQ ID NO: 99) | 738.444 | 144.682 | 397.7 | 62.491 | 0.038524 |
| CQTAESLAVHNITVSECQNESYLNFARKRIKNC (SEQ ID NO: 100) | 697.667 | 143.031 | 367.45 | 55.429 | 0.038717 |
| CHGAERIVRGQTAESLCQKISEWGKIKESPIPC (SEQ ID NO: 101) | 734.917 | 132.945 | 407.625 | 70.500 | 0.038779 |
| GKIKECPIP (SEQ ID NO: 102) | 594.611 | 111.300 | 324.35 | 56.061 | 0.038930 |
| CEWSVNARVNNSDPYSCQNESYLNFARKRIKNC (SEQ ID NO: 103) | 714.944 | 148.086 | 372.8 | 58.717 | 0.039223 |
| LGDRQNESYLNFARK (SEQ ID NO: 104) | 457.556 | 87.314 | 252.4 | 38.376 | 0.039506 |
| CNITVSEQKISAAGKIC (SEQ ID NO: 105) | 828.167 | 161.273 | 460.55 | 60.796 | 0.040192 |
| CNFARKRIKNPEGGLYCSLAVHNITVSEQKISC (SEQ ID NO: 106) | 599.000 | 117.360 | 330.8 | 44.992 | 0.040197 |
| ESYLNFARK (SEQ ID NO: 107) | 535.667 | 101.551 | 296.3 | 46.513 | 0.040403 |
| CKISEWGKIKC (SEQ ID NO: 108) | 672.833 | 131.134 | 367.95 | 57.029 | 0.041005 |
| NESYLNFARKRIKNP (SEQ ID NO: 109) | 602.889 | 112.832 | 333.75 | 55.479 | 0.041060 |
| CVALSELGDRQNESYLCQNESYLNFARKRIKNC (SEQ ID NO: 110) | 761.778 | 149.165 | 406.75 | 72.796 | 0.041142 |

TABLE 2-continued

List of peptide sequences from NOX2 library that are significantly recognized by the MS sera (n = 9) compared to CTRLs (n = 10) (p < 0.05).

| Sequence | | | | | |
|---|---|---|---|---|---|
| CQNESYLNFARKRIKNCVSEQKISEWGKIKESC (SEQ ID NO: 111) | 747.139 | 139.947 | 419.075 | 63.876 | 0.041252 |
| CVSEQKISEWGKIKESCGDRQNESYLNFARKRC (SEQ ID NO: 112) | 846.778 | 166.956 | 462.45 | 69.927 | 0.041538 |
| QNESYLNFARAAIKN (SEQ ID NO: 113) | 421.722 | 74.794 | 244 | 36.768 | 0.041742 |
| CSEQKISEWGKIKESPC (SEQ ID NO: 114) | 501.167 | 101.057 | 271.75 | 39.588 | 0.041995 |
| CVSEQKISEWGKIKESCVSEQKISEWGKIKESC (SEQ ID NO: 115) | 756.639 | 139.081 | 432.35 | 63.156 | 0.042031 |
| WGKIKECPI (SEQ ID NO: 116) | 501.389 | 85.494 | 303.25 | 37.670 | 0.042036 |
| CNFARKRIKNPEGGLYCGDRQNESYLNFARKRC (SEQ ID NO: 117) | 800.500 | 164.282 | 425.15 | 67.492 | 0.042277 |
| VNARVNNSDPAAVAL (SEQ ID NO: 118) | 426.444 | 89.633 | 219.15 | 39.717 | 0.042623 |
| YLNFARKRIKAAEGG (SEQ ID NO: 119) | 299.167 | 48.645 | 181.3 | 26.445 | 0.042780 |
| GDRQNESYLNFARKR (SEQ ID NO: 120) | 325.333 | 71.433 | 163.95 | 27.971 | 0.042865 |
| WCVNARVNNSDPYSV (SEQ ID NO: 121) | 283.889 | 51.504 | 163.8 | 24.175 | 0.043310 |
| CSYLNFARKRIKNPEGCITVSEQKISEWGKIKC (SEQ ID NO: 122) | 796.222 | 141.260 | 457.4 | 74.781 | 0.043355 |
| CAVHNITVSEQKISEWCVSEQKISEWGKIKESC (SEQ ID NO: 123) | 697.000 | 132.608 | 392.5 | 58.017 | 0.043483 |
| CPYSVALSELGDRQNECITVSEQKISEWGKIKC (SEQ ID NO: 124) | 824.056 | 151.125 | 469.75 | 74.499 | 0.044343 |
| CSYLNFARKRIKNPEGCGDRQNESYLNFARKRC (SEQ ID NO: 125) | 786.389 | 154.795 | 430.35 | 70.557 | 0.044707 |
| CAVHNITVSEQKISEWCQNESYLNFARKRIKNC (SEQ ID NO: 126) | 685.667 | 140.191 | 370.15 | 57.325 | 0.044934 |
| LGDRQNESYLAAARK (SEQ ID NO: 127) | 478.278 | 93.425 | 262.75 | 43.574 | 0.045056 |
| CVNARVNNSDPYSVALCVSEQKISEWGKIKESC (SEQ ID NO: 128) | 772.583 | 148.494 | 436.575 | 63.579 | 0.045484 |
| CFNVEWSVNARVNNSDCGDRQNESYLNFARKRC (SEQ ID NO: 129) | 792.889 | 167.256 | 423.15 | 63.958 | 0.046274 |
| CNSDPYSVALSELGDRCVSEQKISEWGKIKESC (SEQ ID NO: 130) | 764.528 | 146.689 | 434.925 | 61.821 | 0.046277 |
| CGDRQNESYLNFARKRCSYLNFARKRIKNPEGC (SEQ ID NO: 131) | 730.222 | 144.653 | 401.95 | 64.840 | 0.046636 |
| DPYSVALSELGDRQN (SEQ ID NO: 132) | 300.556 | 52.221 | 177.25 | 27.831 | 0.046679 |
| CAVHNITVSEQKISEWCSYLNFARKRIKNPEGC (SEQ ID NO: 133) | 648.556 | 118.334 | 375.55 | 57.805 | 0.047030 |
| CVRGQTAESLAVHNITCITVSEQKISEWGKIKC (SEQ ID NO: 134) | 758.278 | 135.230 | 440.5 | 71.450 | 0.047178 |
| CQNESYLNFARKRIKNCSYLNFARKRIKNPEGC (SEQ ID NO: 135) | 711.556 | 140.645 | 396.7 | 60.423 | 0.047697 |
| CESLAVHNITVSEQKICGDRQNESYLNFARKRC (SEQ ID NO: 136) | 730.278 | 143.452 | 409.15 | 61.650 | 0.047716 |
| CRVNNSDPYSVALSELCQNESYLNFARKRIKNC (SEQ ID NO: 137) | 743.167 | 156.061 | 398.05 | 62.948 | 0.047897 |
| CSYLNFARKRIKNPEGCNFARKRIKNPEGGLYC (SEQ ID NO: 138) | 659.944 | 126.954 | 371.8 | 59.312 | 0.048308 |
| CQTAESLAVHNITVSECVSEQKISEWGKIKESC (SEQ ID NO: 139) | 590.111 | 111.059 | 339.65 | 50.662 | 0.048582 |

TABLE 2-continued

List of peptide sequences from NOX2 library that are significantly recognized by the MS sera (n = 9) compared to CTRLs (n = 10) (p < 0.05).

| Sequence | | | | | |
|---|---|---|---|---|---|
| YLNFARKRI (SEQ ID NO: 140) | 601.667 | 108.516 | 345.85 | 59.745 | 0.048726 |
| CFNVEWSVNARVNNSDCVSEQKISEWGKIKESC (SEQ ID NO: 141) | 784.944 | 149.515 | 447.325 | 69.485 | 0.049109 |
| CVSEQKISEWGKIKESCTVSEQKISEWGKIKEC (SEQ ID NO: 142) | 760.333 | 137.654 | 446.5 | 66.920 | 0.049174 |
| CNSDPYSVALSELGDRCITVSEQKISEWGKIKC (SEQ ID NO: 143) | 781.611 | 136.738 | 456.45 | 78.433 | 0.049315 |
| CNITVSEQKISEWGKICGDRQNESYLNFARKRC (SEQ ID NO: 144) | 816.722 | 167.231 | 446.7 | 70.860 | 0.049530 |
| CLGDRQNESYLAAARKC (SEQ ID NO: 145) | 698.944 | 131.913 | 402.85 | 60.271 | 0.049600 |
| QKISEWGKI (SEQ ID NO: 146) | 508.333 | 92.706 | 298.2 | 44.546 | 0.049820 |
| CITVSEQKISEAAKIKC (SEQ ID NO: 147) | 703.000 | 147.115 | 383.25 | 56.600 | 0.049837 |
| CVRGQTAESLAVHNITCVHNITVSEQKISEWGC (SEQ ID NO: 148) | 445.278 | 79.537 | 263.5 | 39.692 | 0.049916 |
| CQKISEWGKIKESPIPCVHNITVSEQKISEWGC (SEQ ID NO: 149) | 442.611 | 82.066 | 263.25 | 32.814 | 0.049972 |
| CQNESYLNFARKRIKNCNFARKRIKNPEGGLYC (SEQ ID NO: 150) | 697.056 | 139.880 | 392.3 | 55.275 | 0.050219 |
| CRVNNSDPYSVALSELCVSEQKISEWGKIKESC (SEQ ID NO: 151) | 731.111 | 139.692 | 422.275 | 60.170 | 0.050319 |
| CGDRQNESYLNFARKRCVSEQKISEWGKIKESC (SEQ ID NO: 152) | 805.278 | 155.053 | 461.6 | 67.947 | 0.050467 |
| CQKISEWGKIKAAPIPC (SEQ ID NO: 153) | 710.778 | 140.027 | 402.15 | 59.861 | 0.050660 |
| CVNARVNNSDPYSVALCTVSEQKISEWGKIKEC (SEQ ID NO: 154) | 799.667 | 154.908 | 455.6 | 69.048 | 0.050729 |
| CEWSVNARVNNSDPYSCVSEQKISEWGKIKESC (SEQ ID NO: 155) | 760.083 | 148.508 | 433.775 | 62.562 | 0.050743 |
| CVRGQTAESLAVHNITCSLAVHNITVSEQKISC (SEQ ID NO: 156) | 546.444 | 110.735 | 304.75 | 47.813 | 0.053099 |

CB245.MAT: double looped conformational peptide, CB245.LIN15AA: linear peptide of 15 amino acids, CB245.LIN9: linear peptide of 9 amino acids, CB245.P2_15AA: single looped conformational peptide of 15 amino acids.

In double looped peptides, three cysteine residues were added, two as first and last amino acid and one in the middle of the sequence. Then peptides of the invention may the whole sequence or the fragments located between two cysteine residues. In single looped peptides, two cysteine residues were added, as first and last amino acid. Then peptides of the invention may the whole sequence or the fragment located between two cysteine residues or the sequence with only one cysteine at either end of the sequence.

FIGS. 15A through 15D report the alignments of the peptides of the invention with fragments of 5HT2aR. It shows that each extracellular region of the 5HT2A receptor overlap with peptides that have an high affinity for MS sera. The asterisks show the 100% identity of amino acids with the different extracellular region of the 5HT2A receptor.

FIGS. 16A and 16B report the alignments of the peptides of the invention with fragments of NOX2. It shows that the extracellular loop 2 and loop 3 of NOX 2 overlap with peptides that have an high affinity for MS sera. The asterisks show the 100% identity of amino acids with the different extracellular region of NOX2 Loop 2 and loop 3.

Elisa

Dose-Response Curves of the Interaction Between MS IgG and DDSK Peptide

The inventors have demonstrated the immunoglobulins of Multiple Sclerosis patients bind serotonin receptor. To evaluate the peptide concentration to use for ELISA assay we performed a dose-response curve. The immunoglobulins of Multiple Sclerosis patients and Control (200 μg) were incubated with different concentrations (50-100-250 μM) of peptide DDSKVFKEGS (named DDSK in the figures) and the absorbance (optical density) of plate was read at 450 nm. FIG. 6 shows that MS IgG bind the DDSK peptide at the concentration higher than 50 μM.

MS IgG Recognize Specially Receptor's Peptide

The MS IgG binds peptides derived from serotonin receptor. To confirm this data, the inventors performed indirect Elisa using two different peptides derived from serotonin receptor compared to scrambled.

The immunoglobulins of Multiple Sclerosis patients and Control (200 μg) were incubated with 100 μM of specific or control peptide and the absorbance (optical density) of plate was read at 450 nm. FIG. 7 shows that MS IgG bind specifically DDSKVFKEGS ((SEQ ID NO: 157), also named "DDSK") and LYGYRWPLPSKL ((SEQ ID NO: 158), also named "LYGY") peptides respect to scrambled (TWYAHNCRLQ, SEQ ID NO: 173).

DDSK Peptide Shows High Sensitivity and Specificity to IgG MS

The inventors have demonstrate the MS IgG binds specific peptide derived from receptor.

To evaluate the sensitivity of the binding, the inventors performed a ROC curve starting from 28 samples each one repeated at least 4 times. In FIG. 8 we show that binding between MS IgG and DDSK peptides has a 82% of sensitivity and 96% of specificity.

IgG from MS Patients Interfere with 5HT2aR Signaling

To evaluate whether the interaction of IgG from MS patients with the membrane 5HT2aR/NOX3 complex could affect cell signaling downstream the receptor, the inventors performed experiments with HEK293 cells transfected in transient with 5HT2aR. The cells were stimulated with IgG from Control or MS patients prior to the stimulation with the endogenous receptor agonist 5-Ht, and then P-ERK1/2 levels were measured. As shown in the FIG. 9A, IgG from MS patients inhibit 5-Ht-mediated induction of P-ERK1/2 levels.

Figure 9B:
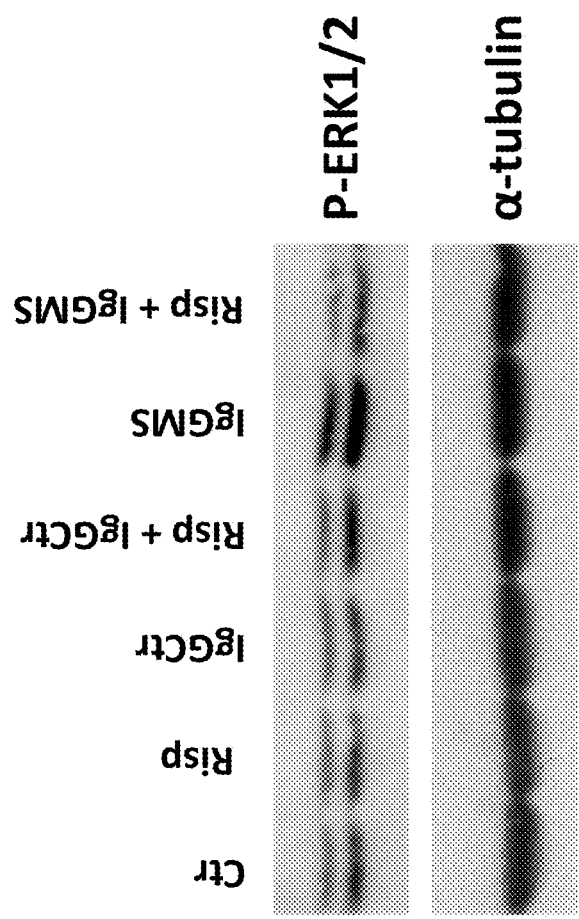

The inventors also provided evidences about the interference of IgG from MS patients with 5HT2aR signaling in human oligodendrocyte cell line MO3-13. Cells were stimulated with IgG from control or MS patients in the presence and absence of risperidone, a serotonin receptor antagonist. In the presence of the substance, IgG from MS patients failed to induce P-ERK1/2 levels thus confirming that autoantibodies present in sera of MS patients increase P-ERK1/2 levels acting on serotonin receptor (FIG. 9B).

Overall, the present results suggest that 5HT2aR-bound autoantibodies present in MS patients may exert an ethiopathogenic role in MS. Therefore, compounds interfering with the immunoglobulins-receptor binding can be used for the treatment of MS.

IgG from MS Patients Increase Reactive Oxygen Species (ROS), DUOX1/2, P-ERK1/2, HaRas and NOX3 Protein Levels and DDSK Peptide Reverts the Effect 5Ht receptors rely on ROS for downstream signaling (Kruk et al., 2013). Therefore, we measured ROS levels, as DCF fluorescence, in MO3-13 cells stimulated with IgG from Control or MS patients in the absence or presence of the DDSK peptide. As shown in FIG. 10A, IgG MS significantly increased ROS levels and preincubation of cells with DDSK peptide reverted the effect. On the contrary, DDSK did not significantly affect ROS levels of IgGCtr treated samples. Scrambled peptides, used as negative control, did not influence ROS levels of IgG MS treated samples (FIG. 10B). The ability of DDSK to interfere with 5HT2a receptor downstream signaling measured as ROS levels, demonstrate that the peptide is able to revert the biological effects of the autoantibodies present in MS sera on human oligodendrocytes and, therefore, that it may be used for the treatment of multiple sclerosis.

In addition to NOX3 and NOX5, MO3-13 cells express also DUOX1 and 2 isoforms (Damiano et al., 2012, PloS); their protein levels are very sensitive to ROS. Other downstream ROS targets are P-ERK, and H-Ras (Refs). For these reasons we also measured DUOX1/2 (FIG. 11), P-ERK1/2 (FIG. 12), NOX3 (FIG. 13) and HaRas (FIG. 14) protein levels by Western blotting in MO3-13 cells stimulated with IgG from Control or MS patients in the absence or presence of the DDSK peptide. As shown in the FIG. 11, 12, 13, 14, IgMS significantly increased DUOX1/2, P-ERK1/2, NOX3 and HaRas protein levels, and preincubation of cells with DDSK peptide reverted the effect. The ability of DDSK to interfere with 5HT2a receptor downstream signaling measured as DUOX1/2, P-ERK1/2, NOX3 and HaRas protein levels levels, further demonstrate that the peptide is able to revert the biological effects of the autoantibodies present in MS sera on human oligodendrocytes and, therefore, that it may be used for the treatment of multiple sclerosis.

On the contrary, incubation of the cells with IgG from control subjects decreased DUOX1/2 and P-ERK1/2, while did not affect HaRas or NOX3 protein levels and DDSK HaRas did not significantly modify the levels of all the protein analyzed.

Altogether, these experiments suggest that peptides with sequences homologue to the extracellular domains of h-5HT2aR are able to counteract the effect of IgMS on 5HT2aR/NOX/ROS signaling pathway in human oligodendrocytes, thus representing a promising specific therapeutic tool for the treatment of Multiple Sclerosis.

REFERENCES

Achiron A, Miron S and Shoenfeld Y (2005) *Isr. Med. Assoc. J.* 7:283-285.
Achten E, Deblaere K (2008) Eur. J. Radiol. 65(2):211-3.
Alvarez-Lafuente R, et al., (2007) *Mult Scler.* 13:590-595.
Babior B M, Lambeth J D and Nauseef W (2002) *Arch. Biochem. Biophys.* 397: 342-344.
Barateiro A and Fernandes A (2014) *Biochim. Biophys. Acta.* 1843:1917-1929.
Barnes N M and Sharp T (1999). *Neuropharmacology,* 38: 1083-1152.
Baroni S S, et al. (2006) *New Eng. J. of Med.* 354: 2667-2676.
Bedard K, and Krause K H (2007) *Physiol.Rev.* 87: 245-313.
Cavaliere F et al., (2013) *Front. Cell. Neurosci.* 7:1-7
Cheli V T, et al., (2015) *Experimental Neurology,* 265: 69-83.
Damiano S, et al. (2012) *PLoS One.* 7, e34405.
Damiano S, et al. (2015) *Int. J. Biochem. Cell Biol.* 60C: 8-18.
Elphick G F, et al. (2004) *Science,* 306:1380-1383.
Fang X L, Shu G, Yu J J, Wang L N, Yang J, Zeng Q J, et al. (2013) *PLoS One.* 8: e53142
Gabrielli A, et al., (2008) *Semin. Immunopathol.* 30: 329-337.
Kruk J S, Vasefi M S, Heikkila J J and Beazely M A (2013) *PLoS One.* 8:e77027.
Lambeth J D (2004) *Nat. Rev. Immunol.* 4: 181-189.
Luque F A, Jaffe S L (2007) Int. Rev. Neurobiol. 79:341-56.
Markianos M, et al., (2009) *J Neurochem* 108:158-64.
Millan M J, et al., (2008) *Trends Pharmacol Sci* 29:454-464.
Noseworthy J H, et al., (2000) N. Engl. J. Med. 343:938-52.
Petry A, Weitnauer M, and Görlach A (2010) *Antioxid. Redox Signal.* 13:467-87.
Pugliatti M, Rosati G, Carton H, et al. (2006) Eur. J. Neurol. 13:700-722.
Ransohoff R M (2012) Nat. Neurosci. 15:1074-1077.
Raote I, Bhattacharya A and Panicker M M (2007) In: Chattopadhyay A, editor. *Serotonin Receptors in Neurobiology.* Boca Raton (Fla.): CRC Press; Chapter 6.
Regmi S C, Park S Y, Ku S K and Kim J A (2014) *Free Radic Biol Med.* 69:377-389.

Rosati G (2001) Neurol. Sci. 22:117-139.
Seru R, et al. (2004) *J. Neurochem.* 91: 613-622.
Shi L Z, et al., (2011) J. Exp. Med. 208:1367-1376.
Slootstra J W, PuiJ k, Ligtvoet G J, Langeveld J P, Meloen R H. (1996) Mol. Divers. 1:87:96.

Svegliati S, et al. (2005) *J. Biol. Chem.* 280: 36474-36482.
Timmerman et. al. (2007) J. Mol. Recognit. 20:283-299.
Trojano M, Paolicelli D (2001) Neurol. SCi. Suppl 2:S98-102.

The invention claimed is:

1. A peptide consisting of an amino acid sequence that is 100% identical to:
   (a) LYGYRWPLPSKL (SEQ ID NO: 158);
   (b) YRWPLPSKL (SEQ ID NO: 14);
   (c) RWPLPSKL (residues 2-9 of SEQ ID NO: 14); or
   (d) RWP (residues 2-4 of SEQ ID NO: 14);
wherein the N-terminal amino group of the peptide is acylated with an N-acyl group selected from the group consisting of acetyl, lauroyl, myristoyl, palmitoyl, steroyl, oleoyl, or lineoyl; and
   wherein the peptide is able to bind multiple sclerosis auto-antibodies.

2. The peptide according to claim 1 wherein the sequence consists of YRWPLPSKL (SEQ ID NO: 14).

3. The peptide according to claim 1 wherein the sequence consists of RWPLPSKL (residues 2-9 of SEQ ID NO: 14).

4. The peptide according to claim 1, wherein the sequence consists of RWP (residues 2-4 of SEQ ID NO: 14).

5. The peptide according to claim 1, in linear or conformational form.

6. A pharmaceutical composition comprising the peptide according to claim 1, and pharmaceutically acceptable excipients.

7. The pharmaceutical composition according to claim 6, further comprising a therapeutic agent, selected from the group consisting of vitamins, nootropics, neuroprotective agents, racetams, isoflavones, choline, amphetamines, xanthines, adrenergics, cholinergics, serotonigergic, dopaminergics, eugeroics, GABA blockers, AMPAkines, PDE4 inhibitors, glutamate antagonists, statins, antioxidants, caspase inhibitors, neurotrophic factors, antiapoptotic agents, and anti-pain medications.

8. The pharmaceutical composition according to claim 6, further comprising a therapeutic agent selected from the group consisting of beta-interferon, methylphenidate, vitamin B, vitamin C, vitamin D, vitamin E, choline, 170-Estradiol, ginsenoside Rd, progesterone, nicotine, caffeine, and natalizumab.

9. The pharmaceutical composition according to claim 7, further comprising a peptide that is 100% identical to the amino acid sequence as set forth in SEQ ID NO: 157, or a fragment thereof.

10. The pharmaceutical composition according to claim 9, wherein the fragment consists of the sequence SKVFKEGS (residues 3-10 of SEQ ID NO: 157).

11. The pharmaceutical composition according to claim 9, wherein the fragment consists of FKE (residues 6-8 of SEQ ID NO: 157).

12. A method for detecting multiple sclerosis auto-antibodies in a patient, the method comprising:
   (a) obtaining a biological sample isolated from the patient; and
   (b) detecting whether multiple sclerosis auto-antibodies are present in the biological sample by contacting the biological sample with a peptide, and detecting binding between the multiple sclerosis auto-antibodies and the peptide;

wherein the peptide comprises a peptide according to claim 1 or a fragment thereof consisting of the sequence SKL (residues 7-9 of SEQ ID NO.14).

13. The method according to claim 12, further comprising:

(c) detecting whether multiple sclerosis auto-antibodies are present in the biological sample by contacting the biological sample with a peptide that is 100% identical to the amino acid sequence as set forth in SEQ ID NO: 157, or a fragment thereof, and detecting binding between multiple sclerosis auto-antibodies and said peptide or fragment thereof.

14. The method according to claim 13 wherein the fragment of the peptide of SEQ ID NO: 157 consists of the sequence SKVFKEGS (residues 3-10 of SEQ ID NO: 157).

15. The method according to claim 13 wherein the fragment of the peptide of SEQ ID NO: 157 has the sequence FKE (residues 6-8 of SEQ ID NO: 157).

16. A method for detecting multiple sclerosis auto-antibodies in a patient according to claim 13, further comprising using the detection of binding between multiple sclerosis auto-antibodies and the peptide of SEQ ID NO: 157 or fragment thereof wherein said fragment has the sequence SKVFKEGS (residues 3-10 of SEQ ID NO: 157) or FKE (residues 6-8 of SEQ ID NO: 157) for diagnosing or monitoring the progression of multiple sclerosis, identifying a therapy for multiple sclerosis, or monitoring a therapy for multiple sclerosis.

17. A method for detecting multiple sclerosis auto-antibodies in a patient according to claim 12, further comprising using the detection of binding between multiple sclerosis auto-antibodies and the peptide for diagnosing or monitoring the progression of multiple sclerosis, identifying a therapy for multiple sclerosis, or monitoring a therapy for multiple sclerosis.

18. A kit for diagnosing or monitoring the progression of multiple sclerosis, or for identifying or monitoring a therapy for multiple sclerosis, comprising the peptide according to claim 1.

19. A kit according to claim 18, further comprising a peptide consisting of the amino acid sequence of SEQ ID NO: 157 or fragment thereof.

* * * * *

```
                               SEQUENCE LISTING

<160> NUMBER OF SEQ ID NOS: 174

<210> SEQ ID NO 1
<211> LENGTH: 570
<212> TYPE: PRT
<213> ORGANISM: Homo sapiens

<400> SEQUENCE: 1

Met Gly Asn Trp Ala Val Asn Glu Gly Leu Ser Ile Phe Val Ile Leu
1               5                   10                  15

Val Trp Leu Gly Leu Asn Val Phe Leu Phe Val Trp Tyr Tyr Arg Val
            20                  25                  30

Tyr Asp Ile Pro Pro Lys Phe Phe Tyr Thr Arg Lys Leu Leu Gly Ser
        35                  40                  45

Ala Leu Ala Leu Ala Arg Ala Pro Ala Ala Cys Leu Asn Phe Asn Cys
    50                  55                  60

Met Leu Ile Leu Leu Pro Val Cys Arg Asn Leu Leu Ser Phe Leu Arg
65                  70                  75                  80

Gly Ser Ser Ala Cys Cys Ser Thr Arg Val Arg Arg Gln Leu Asp Arg
                85                  90                  95

Asn Leu Thr Phe His Lys Met Val Ala Trp Met Ile Ala Leu His Ser
            100                 105                 110

Ala Ile His Thr Ile Ala His Leu Phe Asn Val Glu Trp Cys Val Asn
        115                 120                 125

Ala Arg Val Asn Asn Ser Asp Pro Tyr Ser Val Ala Leu Ser Glu Leu
    130                 135                 140

Gly Asp Arg Gln Asn Glu Ser Tyr Leu Asn Phe Ala Arg Lys Arg Ile
145                 150                 155                 160

Lys Asn Pro Glu Gly Gly Leu Tyr Leu Ala Val Thr Leu Leu Ala Gly
                165                 170                 175

Ile Thr Gly Val Val Ile Thr Leu Cys Leu Ile Leu Ile Ile Thr Ser
            180                 185                 190

Ser Thr Lys Thr Ile Arg Arg Ser Tyr Phe Glu Val Phe Trp Tyr Thr
        195                 200                 205

His His Leu Phe Val Ile Phe Phe Ile Gly Leu Ala Ile His Gly Ala
    210                 215                 220

Glu Arg Ile Val Arg Gly Gln Thr Ala Glu Ser Leu Ala Val His Asn
225                 230                 235                 240

Ile Thr Val Cys Glu Gln Lys Ile Ser Glu Trp Gly Lys Ile Lys Glu
                245                 250                 255

Cys Pro Ile Pro Gln Phe Ala Gly Asn Pro Pro Met Thr Trp Lys Trp
            260                 265                 270

Ile Val Gly Pro Met Phe Leu Tyr Leu Cys Glu Arg Leu Val Arg Phe
        275                 280                 285

Trp Arg Ser Gln Gln Lys Val Val Ile Thr Lys Val Val Thr His Pro
    290                 295                 300

Phe Lys Thr Ile Glu Leu Gln Met Lys Lys Lys Gly Phe Lys Met Glu
305                 310                 315                 320
```

Val Gly Gln Tyr Ile Phe Val Lys Cys Pro Lys Val Ser Lys Leu Glu
                325                 330                 335

Trp His Pro Phe Thr Leu Thr Ser Ala Pro Glu Glu Asp Phe Phe Ser
            340                 345                 350

Ile His Ile Arg Ile Val Gly Asp Trp Thr Glu Gly Leu Phe Asn Ala
        355                 360                 365

Cys Gly Cys Asp Lys Gln Glu Phe Gln Asp Ala Trp Lys Leu Pro Lys
    370                 375                 380

Ile Ala Val Asp Gly Pro Phe Gly Thr Ala Ser Glu Asp Val Phe Ser
385                 390                 395                 400

Tyr Glu Val Val Met Leu Val Gly Ala Gly Ile Gly Val Thr Pro Phe
                405                 410                 415

Ala Ser Ile Leu Lys Ser Val Trp Tyr Lys Tyr Cys Asn Asn Ala Thr
            420                 425                 430

Asn Leu Lys Leu Lys Lys Ile Tyr Phe Tyr Trp Leu Cys Arg Asp Thr
        435                 440                 445

His Ala Phe Glu Trp Phe Ala Asp Leu Leu Gln Leu Leu Glu Ser Gln
    450                 455                 460

Met Gln Glu Arg Asn Asn Ala Gly Phe Leu Ser Tyr Asn Ile Tyr Leu
465                 470                 475                 480

Thr Gly Trp Asp Glu Ser Gln Ala Asn His Phe Ala Val His Asp
                485                 490                 495

Glu Glu Lys Asp Val Ile Thr Gly Leu Lys Gln Lys Thr Leu Tyr Gly
                500                 505                 510

Arg Pro Asn Trp Asp Asn Glu Phe Lys Thr Ile Ala Ser Gln His Pro
            515                 520                 525

Asn Thr Arg Ile Gly Val Phe Leu Cys Gly Pro Glu Ala Leu Ala Glu
        530                 535                 540

Thr Leu Ser Lys Gln Ser Ile Ser Asn Ser Glu Ser Gly Pro Arg Gly
545                 550                 555                 560

Val His Phe Ile Phe Asn Lys Glu Asn Phe
                565                 570

<210> SEQ ID NO 2
<211> LENGTH: 471
<212> TYPE: PRT
<213> ORGANISM: Homo sapiens

<400> SEQUENCE: 2

Met Asp Ile Leu Cys Glu Glu Asn Thr Ser Leu Ser Ser Thr Thr Asn
1               5                   10                  15

Ser Leu Met Gln Leu Asn Asp Asp Thr Arg Leu Tyr Ser Asn Asp Phe
            20                  25                  30

Asn Ser Gly Glu Ala Asn Thr Ser Asp Ala Phe Asn Trp Thr Val Asp
        35                  40                  45

Ser Glu Asn Arg Thr Asn Leu Ser Cys Glu Gly Cys Leu Ser Pro Ser
    50                  55                  60

Cys Leu Ser Leu Leu His Leu Gln Glu Lys Asn Trp Ser Ala Leu Leu
65                  70                  75                  80

Thr Ala Val Val Ile Ile Leu Thr Ile Ala Gly Asn Ile Leu Val Ile
                85                  90                  95

Met Ala Val Ser Leu Glu Lys Lys Leu Gln Asn Ala Thr Asn Tyr Phe
            100                 105                 110

Leu Met Ser Leu Ala Ile Ala Asp Met Leu Leu Gly Phe Leu Val Met

-continued

```
                115                 120                 125
Pro Val Ser Met Leu Thr Ile Leu Tyr Gly Tyr Arg Trp Pro Leu Pro
130                 135                 140
Ser Lys Leu Cys Ala Val Trp Ile Tyr Leu Asp Val Leu Phe Ser Thr
145                 150                 155                 160
Ala Ser Ile Met His Leu Cys Ala Ile Ser Leu Asp Arg Tyr Val Ala
                165                 170                 175
Ile Gln Asn Pro Ile His His Ser Arg Phe Asn Ser Arg Thr Lys Ala
                180                 185                 190
Phe Leu Lys Ile Ile Ala Val Trp Thr Ile Ser Val Gly Ile Ser Met
                195                 200                 205
Pro Ile Pro Val Phe Gly Leu Gln Asp Asp Ser Lys Val Phe Lys Glu
210                 215                 220
Gly Ser Cys Leu Leu Ala Asp Asp Asn Phe Val Leu Ile Gly Ser Phe
225                 230                 235                 240
Val Ser Phe Phe Ile Pro Leu Thr Ile Met Val Ile Thr Tyr Phe Leu
                245                 250                 255
Thr Ile Lys Ser Leu Gln Lys Glu Ala Thr Leu Cys Val Ser Asp Leu
                260                 265                 270
Gly Thr Arg Ala Lys Leu Ala Ser Phe Ser Phe Leu Pro Gln Ser Ser
                275                 280                 285
Leu Ser Ser Glu Lys Leu Phe Gln Arg Ser Ile His Arg Glu Pro Gly
                290                 295                 300
Ser Tyr Thr Gly Arg Arg Thr Met Gln Ser Ile Ser Asn Glu Gln Lys
305                 310                 315                 320
Ala Cys Lys Val Leu Gly Ile Val Phe Phe Leu Phe Val Val Met Trp
                325                 330                 335
Cys Pro Phe Phe Ile Thr Asn Ile Met Ala Val Ile Cys Lys Glu Ser
                340                 345                 350
Cys Asn Glu Asp Val Ile Gly Ala Leu Leu Asn Val Phe Val Trp Ile
                355                 360                 365
Gly Tyr Leu Ser Ser Ala Val Asn Pro Leu Val Tyr Thr Leu Phe Asn
370                 375                 380
Lys Thr Tyr Arg Ser Ala Phe Ser Arg Tyr Ile Gln Cys Gln Tyr Lys
385                 390                 395                 400
Glu Asn Lys Lys Pro Leu Gln Leu Ile Leu Val Asn Thr Ile Pro Ala
                405                 410                 415
Leu Ala Tyr Lys Ser Ser Gln Leu Gln Met Gly Gln Lys Lys Asn Ser
                420                 425                 430
Lys Gln Asp Ala Lys Thr Thr Asp Asn Asp Cys Ser Met Val Ala Leu
                435                 440                 445
Gly Lys Gln His Ser Glu Glu Ala Ser Lys Asp Asn Ser Asp Gly Val
                450                 455                 460
Asn Glu Lys Val Ser Cys Val
465                 470

<210> SEQ ID NO 3
<211> LENGTH: 19
<212> TYPE: PRT
<213> ORGANISM: Homo sapiens

<400> SEQUENCE: 3

Tyr Arg Val Tyr Asp Ile Pro Pro Lys Phe Phe Tyr Thr Arg Lys Leu
1               5                   10                  15
```

Leu Gly Ser

<210> SEQ ID NO 4
<211> LENGTH: 46
<212> TYPE: PRT
<213> ORGANISM: Homo sapiens

<400> SEQUENCE: 4

```
Glu Trp Cys Val Asn Ala Arg Val Asn Asn Ser Asp Pro Tyr Ser Val
1               5                   10                  15

Ala Leu Ser Glu Leu Gly Asp Arg Gln Asn Glu Ser Tyr Leu Asn Phe
            20                  25                  30

Ala Arg Lys Arg Ile Lys Asn Pro Glu Gly Gly Leu Tyr Leu
        35                  40                  45
```

<210> SEQ ID NO 5
<211> LENGTH: 40
<212> TYPE: PRT
<213> ORGANISM: Homo sapiens

<400> SEQUENCE: 5

```
His Gly Ala Glu Arg Ile Val Arg Gly Gln Thr Ala Glu Ser Leu Ala
1               5                   10                  15

Val His Asn Ile Thr Val Cys Glu Gln Lys Ile Ser Glu Trp Gly Lys
            20                  25                  30

Ile Lys Glu Cys Pro Ile Pro Gln
        35                  40
```

<210> SEQ ID NO 6
<211> LENGTH: 76
<212> TYPE: PRT
<213> ORGANISM: Homo sapiens

<400> SEQUENCE: 6

```
Met Asp Ile Leu Cys Glu Glu Asn Thr Ser Leu Ser Ser Thr Thr Asn
1               5                   10                  15

Ser Leu Met Gln Leu Asn Asp Asp Thr Arg Leu Tyr Ser Asn Asp Phe
            20                  25                  30

Asn Ser Gly Glu Ala Asn Thr Ser Asp Ala Phe Asn Trp Thr Val Asp
        35                  40                  45

Ser Glu Asn Arg Thr Asn Leu Ser Cys Glu Gly Cys Leu Ser Pro Ser
    50                  55                  60

Cys Leu Ser Leu Leu His Leu Gln Glu Lys Asn Trp
65                  70                  75
```

<210> SEQ ID NO 7
<211> LENGTH: 16
<212> TYPE: PRT
<213> ORGANISM: Homo sapiens

<400> SEQUENCE: 7

```
Leu Thr Ile Leu Tyr Gly Tyr Arg Trp Pro Leu Pro Ser Lys Leu Cys
1               5                   10                  15
```

<210> SEQ ID NO 8
<211> LENGTH: 19
<212> TYPE: PRT
<213> ORGANISM: Homo sapiens

<400> SEQUENCE: 8

```
Leu Gln Asp Asp Ser Lys Val Phe Lys Glu Gly Ser Cys Leu Leu Ala
```

Asp Asp Asn

<210> SEQ ID NO 9
<211> LENGTH: 16
<212> TYPE: PRT
<213> ORGANISM: Homo sapiens

<400> SEQUENCE: 9

Val Ile Cys Lys Glu Ser Cys Asn Glu Asp Val Ile Gly Ala Leu Leu
1               5                   10                  15

<210> SEQ ID NO 10
<211> LENGTH: 29
<212> TYPE: PRT
<213> ORGANISM: Artificial Sequence
<220> FEATURE:
<223> OTHER INFORMATION: synthetic

<400> SEQUENCE: 10

Cys Asn Ser Leu Met Gln Leu Asn Asp Asp Thr Arg Leu Tyr Cys Met
1               5                   10                  15

Asp Ile Leu Ser Glu Glu Asn Thr Ser Leu Ser Ser Cys
            20                  25

<210> SEQ ID NO 11
<211> LENGTH: 29
<212> TYPE: PRT
<213> ORGANISM: Artificial Sequence
<220> FEATURE:
<223> OTHER INFORMATION: synthetic

<400> SEQUENCE: 11

Cys Leu Thr Ile Leu Tyr Gly Tyr Arg Trp Pro Leu Pro Ser Cys Met
1               5                   10                  15

Asp Ile Leu Ser Glu Glu Asn Thr Ser Leu Ser Ser Cys
            20                  25

<210> SEQ ID NO 12
<211> LENGTH: 15
<212> TYPE: PRT
<213> ORGANISM: Artificial Sequence
<220> FEATURE:
<223> OTHER INFORMATION: synthetic

<400> SEQUENCE: 12

Leu Thr Ile Leu Tyr Gly Tyr Arg Trp Pro Ala Ala Ser Lys Leu
1               5                   10                  15

<210> SEQ ID NO 13
<211> LENGTH: 29
<212> TYPE: PRT
<213> ORGANISM: Artificial Sequence
<220> FEATURE:
<223> OTHER INFORMATION: synthetic

<400> SEQUENCE: 13

Cys Leu Tyr Gly Tyr Arg Trp Pro Leu Pro Ser Lys Leu Ser Cys Met
1               5                   10                  15

Asp Ile Leu Ser Glu Glu Asn Thr Ser Leu Ser Ser Cys
            20                  25

<210> SEQ ID NO 14
<211> LENGTH: 9

<212> TYPE: PRT
<213> ORGANISM: Artificial Sequence
<220> FEATURE:
<223> OTHER INFORMATION: synthetic

<400> SEQUENCE: 14

Tyr Arg Trp Pro Leu Pro Ser Lys Leu
1               5

<210> SEQ ID NO 15
<211> LENGTH: 29
<212> TYPE: PRT
<213> ORGANISM: Artificial Sequence
<220> FEATURE:
<223> OTHER INFORMATION: synthetic

<400> SEQUENCE: 15

Cys Asn Ser Leu Met Gln Leu Asn Asp Asp Thr Arg Leu Tyr Cys Leu
1               5                   10                  15

Ser Ser Glu Gly Ser Leu Ser Pro Ser Ser Leu Ser Cys
            20                  25

<210> SEQ ID NO 16
<211> LENGTH: 29
<212> TYPE: PRT
<213> ORGANISM: Artificial Sequence
<220> FEATURE:
<223> OTHER INFORMATION: synthetic

<400> SEQUENCE: 16

Cys Leu Gln Asp Asp Ser Lys Val Phe Lys Glu Gly Ser Ser Cys Met
1               5                   10                  15

Asp Ile Leu Ser Glu Glu Asn Thr Ser Leu Ser Ser Cys
            20                  25

<210> SEQ ID NO 17
<211> LENGTH: 15
<212> TYPE: PRT
<213> ORGANISM: Artificial Sequence
<220> FEATURE:
<223> OTHER INFORMATION: synthetic

<400> SEQUENCE: 17

Leu Thr Ile Leu Tyr Gly Tyr Arg Trp Pro Leu Pro Ser Lys Leu
1               5                   10                  15

<210> SEQ ID NO 18
<211> LENGTH: 29
<212> TYPE: PRT
<213> ORGANISM: Artificial Sequence
<220> FEATURE:
<223> OTHER INFORMATION: synthetic

<400> SEQUENCE: 18

Cys Met Gln Leu Asn Asp Asp Thr Arg Leu Tyr Ser Asn Asp Cys Met
1               5                   10                  15

Asp Ile Leu Ser Glu Glu Asn Thr Ser Leu Ser Ser Cys
            20                  25

<210> SEQ ID NO 19
<211> LENGTH: 29
<212> TYPE: PRT
<213> ORGANISM: Artificial Sequence
<220> FEATURE:
<223> OTHER INFORMATION: synthetic

```
<400> SEQUENCE: 19

Cys Leu Ser Pro Ser Ser Leu Ser Leu Leu His Leu Gln Glu Cys Met
1               5                   10                  15

Asp Ile Leu Ser Glu Glu Asn Thr Ser Leu Ser Ser Cys
            20                  25
```

```
<210> SEQ ID NO 20
<211> LENGTH: 29
<212> TYPE: PRT
<213> ORGANISM: Artificial Sequence
<220> FEATURE:
<223> OTHER INFORMATION: synthetic

<400> SEQUENCE: 20

Cys Ser Thr Thr Asn Ser Leu Met Gln Leu Asn Asp Asp Thr Cys Met
1               5                   10                  15

Asp Ile Leu Ser Glu Glu Asn Thr Ser Leu Ser Ser Cys
            20                  25
```

```
<210> SEQ ID NO 21
<211> LENGTH: 29
<212> TYPE: PRT
<213> ORGANISM: Artificial Sequence
<220> FEATURE:
<223> OTHER INFORMATION: synthetic

<400> SEQUENCE: 21

Cys Leu Thr Ile Leu Tyr Gly Tyr Arg Trp Pro Leu Pro Ser Cys Lys
1               5                   10                  15

Glu Ser Ser Asn Glu Asp Val Ile Gly Ala Leu Leu Cys
            20                  25
```

```
<210> SEQ ID NO 22
<211> LENGTH: 29
<212> TYPE: PRT
<213> ORGANISM: Artificial Sequence
<220> FEATURE:
<223> OTHER INFORMATION: synthetic

<400> SEQUENCE: 22

Cys Thr Val Asp Ser Glu Asn Arg Thr Asn Leu Ser Ser Glu Cys Met
1               5                   10                  15

Asp Ile Leu Ser Glu Glu Asn Thr Ser Leu Ser Ser Cys
            20                  25
```

```
<210> SEQ ID NO 23
<211> LENGTH: 9
<212> TYPE: PRT
<213> ORGANISM: Artificial Sequence
<220> FEATURE:
<223> OTHER INFORMATION: synthetic

<400> SEQUENCE: 23

Gly Tyr Arg Trp Pro Leu Pro Ser Lys
1               5
```

```
<210> SEQ ID NO 24
<211> LENGTH: 29
<212> TYPE: PRT
<213> ORGANISM: Artificial Sequence
<220> FEATURE:
<223> OTHER INFORMATION: synthetic

<400> SEQUENCE: 24
```

Cys Met Gln Leu Asn Asp Asp Thr Arg Leu Tyr Ser Asn Asp Cys Ser
1               5                   10                  15

Gly Glu Ala Asn Thr Ser Asp Ala Phe Asn Trp Thr Cys
            20                  25

<210> SEQ ID NO 25
<211> LENGTH: 29
<212> TYPE: PRT
<213> ORGANISM: Artificial Sequence
<220> FEATURE:
<223> OTHER INFORMATION: synthetic

<400> SEQUENCE: 25

Cys Asp Ser Lys Val Phe Lys Glu Gly Ser Ser Leu Leu Ala Cys Lys
1               5                   10                  15

Glu Ser Ser Asn Glu Asp Val Ile Gly Ala Leu Leu Cys
            20                  25

<210> SEQ ID NO 26
<211> LENGTH: 29
<212> TYPE: PRT
<213> ORGANISM: Artificial Sequence
<220> FEATURE:
<223> OTHER INFORMATION: synthetic

<400> SEQUENCE: 26

Cys Glu Asn Thr Ser Leu Ser Ser Thr Asn Ser Leu Met Cys Met
1               5                   10                  15

Asp Ile Leu Ser Glu Glu Asn Thr Ser Leu Ser Ser Cys
            20                  25

<210> SEQ ID NO 27
<211> LENGTH: 29
<212> TYPE: PRT
<213> ORGANISM: Artificial Sequence
<220> FEATURE:
<223> OTHER INFORMATION: synthetic

<400> SEQUENCE: 27

Cys Ser Leu Ser Ser Thr Thr Asn Ser Leu Met Gln Leu Asn Cys Met
1               5                   10                  15

Asp Ile Leu Ser Glu Glu Asn Thr Ser Leu Ser Ser Cys
            20                  25

<210> SEQ ID NO 28
<211> LENGTH: 28
<212> TYPE: PRT
<213> ORGANISM: Artificial Sequence
<220> FEATURE:
<223> OTHER INFORMATION: synthetic

<400> SEQUENCE: 28

Cys Asn Ser Leu Met Gln Leu Asn Asp Thr Arg Leu Tyr Cys Ser Gly
1               5                   10                  15

Glu Ala Asn Thr Ser Asp Ala Phe Asn Trp Thr Cys
            20                  25

<210> SEQ ID NO 29
<211> LENGTH: 29
<212> TYPE: PRT
<213> ORGANISM: Artificial Sequence
<220> FEATURE:
<223> OTHER INFORMATION: synthetic

<400> SEQUENCE: 29

```
Cys Leu Tyr Gly Tyr Arg Trp Pro Leu Pro Ser Lys Leu Ser Cys Lys
1               5                  10                  15

Glu Ser Ser Asn Glu Asp Val Ile Gly Ala Leu Leu Cys
            20                  25
```

<210> SEQ ID NO 30
<211> LENGTH: 29
<212> TYPE: PRT
<213> ORGANISM: Artificial Sequence
<220> FEATURE:
<223> OTHER INFORMATION: synthetic

<400> SEQUENCE: 30

```
Cys Met Asp Ile Leu Ser Glu Glu Asn Thr Ser Leu Ser Ser Cys Met
1               5                  10                  15

Gln Leu Asn Asp Asp Thr Arg Leu Tyr Ser Asn Asp Cys
            20                  25
```

<210> SEQ ID NO 31
<211> LENGTH: 29
<212> TYPE: PRT
<213> ORGANISM: Artificial Sequence
<220> FEATURE:
<223> OTHER INFORMATION: synthetic

<400> SEQUENCE: 31

```
Cys Ser Asp Ala Phe Asn Trp Thr Val Asp Ser Glu Asn Arg Cys Met
1               5                  10                  15

Asp Ile Leu Ser Glu Glu Asn Thr Ser Leu Ser Ser Cys
            20                  25
```

<210> SEQ ID NO 32
<211> LENGTH: 15
<212> TYPE: PRT
<213> ORGANISM: Artificial Sequence
<220> FEATURE:
<223> OTHER INFORMATION: synthetic

<400> SEQUENCE: 32

```
Thr Val Asp Ser Glu Asn Arg Thr Asn Leu Ala Ala Glu Gly Cys
1               5                  10                  15
```

<210> SEQ ID NO 33
<211> LENGTH: 29
<212> TYPE: PRT
<213> ORGANISM: Artificial Sequence
<220> FEATURE:
<223> OTHER INFORMATION: synthetic

<400> SEQUENCE: 33

```
Cys Asn Asp Asp Thr Arg Leu Tyr Ser Asn Asp Phe Asn Ser Cys Met
1               5                  10                  15

Asp Ile Leu Ser Glu Glu Asn Thr Ser Leu Ser Ser Cys
            20                  25
```

<210> SEQ ID NO 34
<211> LENGTH: 29
<212> TYPE: PRT
<213> ORGANISM: Artificial Sequence
<220> FEATURE:
<223> OTHER INFORMATION: synthetic

<400> SEQUENCE: 34

```
Cys Thr Val Asp Ser Glu Asn Arg Thr Asn Leu Ser Ser Glu Cys Arg
```

```
1               5                   10                  15
Thr Asn Leu Ser Ser Glu Gly Ser Leu Ser Pro Ser Cys
            20                  25

<210> SEQ ID NO 35
<211> LENGTH: 29
<212> TYPE: PRT
<213> ORGANISM: Artificial Sequence
<220> FEATURE:
<223> OTHER INFORMATION: synthetic

<400> SEQUENCE: 35

Cys Leu Ser Ser Glu Gly Ser Leu Ser Pro Ser Ser Leu Ser Cys Met
1               5                   10                  15

Asp Ile Leu Ser Glu Glu Asn Thr Ser Leu Ser Ser Cys
            20                  25

<210> SEQ ID NO 36
<211> LENGTH: 29
<212> TYPE: PRT
<213> ORGANISM: Artificial Sequence
<220> FEATURE:
<223> OTHER INFORMATION: synthetic

<400> SEQUENCE: 36

Cys Leu Ser Pro Ser Ser Leu Ser Leu Leu His Leu Gln Glu Cys Thr
1               5                   10                  15

Val Asp Ser Glu Asn Arg Thr Asn Leu Ser Ser Glu Cys
            20                  25

<210> SEQ ID NO 37
<211> LENGTH: 29
<212> TYPE: PRT
<213> ORGANISM: Artificial Sequence
<220> FEATURE:
<223> OTHER INFORMATION: synthetic

<400> SEQUENCE: 37

Cys Asp Ser Lys Val Phe Lys Glu Gly Ser Ser Leu Leu Ala Cys Met
1               5                   10                  15

Asp Ile Leu Ser Glu Glu Asn Thr Ser Leu Ser Ser Cys
            20                  25

<210> SEQ ID NO 38
<211> LENGTH: 15
<212> TYPE: PRT
<213> ORGANISM: Artificial Sequence
<220> FEATURE:
<223> OTHER INFORMATION: synthetic

<400> SEQUENCE: 38

Thr Ile Leu Tyr Gly Tyr Arg Trp Pro Leu Pro Ser Lys Leu Cys
1               5                   10                  15

<210> SEQ ID NO 39
<211> LENGTH: 29
<212> TYPE: PRT
<213> ORGANISM: Artificial Sequence
<220> FEATURE:
<223> OTHER INFORMATION: synthetic

<400> SEQUENCE: 39

Cys Phe Asn Trp Thr Val Asp Ser Glu Asn Arg Thr Asn Leu Cys Met
1               5                   10                  15
```

Asp Ile Leu Ser Glu Glu Asn Thr Ser Leu Ser Ser Cys
            20                  25

<210> SEQ ID NO 40
<211> LENGTH: 15
<212> TYPE: PRT
<213> ORGANISM: Artificial Sequence
<220> FEATURE:
<223> OTHER INFORMATION: synthetic

<400> SEQUENCE: 40

Ser Thr Thr Asn Ser Leu Met Gln Leu Asn Ala Ala Thr Arg Leu
1               5                   10                  15

<210> SEQ ID NO 41
<211> LENGTH: 29
<212> TYPE: PRT
<213> ORGANISM: Artificial Sequence
<220> FEATURE:
<223> OTHER INFORMATION: synthetic

<400> SEQUENCE: 41

Cys Leu Tyr Gly Tyr Arg Trp Pro Leu Pro Ser Lys Leu Ser Cys Tyr
1               5                   10                  15

Ser Asn Asp Phe Asn Ser Gly Glu Ala Asn Thr Ser Cys
            20                  25

<210> SEQ ID NO 42
<211> LENGTH: 15
<212> TYPE: PRT
<213> ORGANISM: Artificial Sequence
<220> FEATURE:
<223> OTHER INFORMATION: synthetic

<400> SEQUENCE: 42

Gln Asp Asp Ser Lys Val Phe Lys Glu Gly Ala Ala Leu Leu Ala
1               5                   10                  15

<210> SEQ ID NO 43
<211> LENGTH: 29
<212> TYPE: PRT
<213> ORGANISM: Artificial Sequence
<220> FEATURE:
<223> OTHER INFORMATION: synthetic

<400> SEQUENCE: 43

Cys Asn Ser Leu Met Gln Leu Asn Asp Asp Thr Arg Leu Tyr Cys Tyr
1               5                   10                  15

Ser Asn Asp Phe Asn Ser Gly Glu Ala Asn Thr Ser Cys
            20                  25

<210> SEQ ID NO 44
<211> LENGTH: 17
<212> TYPE: PRT
<213> ORGANISM: Artificial Sequence
<220> FEATURE:
<223> OTHER INFORMATION: synthetic

<400> SEQUENCE: 44

Cys Leu Thr Ile Leu Tyr Gly Tyr Arg Trp Pro Leu Pro Ser Lys Leu
1               5                   10                  15

Cys

<210> SEQ ID NO 45
<211> LENGTH: 29

```
<212> TYPE: PRT
<213> ORGANISM: Artificial Sequence
<220> FEATURE:
<223> OTHER INFORMATION: synthetic

<400> SEQUENCE: 45

Cys Leu Tyr Gly Tyr Arg Trp Pro Leu Pro Ser Lys Leu Ser Cys Ser
1               5                   10                  15

Asp Ala Phe Asn Trp Thr Val Asp Ser Glu Asn Arg Cys
            20                  25

<210> SEQ ID NO 46
<211> LENGTH: 29
<212> TYPE: PRT
<213> ORGANISM: Artificial Sequence
<220> FEATURE:
<223> OTHER INFORMATION: synthetic

<400> SEQUENCE: 46

Cys Asp Ser Lys Val Phe Lys Glu Gly Ser Ser Leu Leu Ala Cys Ser
1               5                   10                  15

Gly Glu Ala Asn Thr Ser Asp Ala Phe Asn Trp Thr Cys
            20                  25

<210> SEQ ID NO 47
<211> LENGTH: 29
<212> TYPE: PRT
<213> ORGANISM: Artificial Sequence
<220> FEATURE:
<223> OTHER INFORMATION: synthetic

<400> SEQUENCE: 47

Cys Val Phe Lys Glu Gly Ser Ser Leu Leu Ala Asp Asp Asn Cys Lys
1               5                   10                  15

Glu Ser Ser Asn Glu Asp Val Ile Gly Ala Leu Leu Cys
            20                  25

<210> SEQ ID NO 48
<211> LENGTH: 29
<212> TYPE: PRT
<213> ORGANISM: Artificial Sequence
<220> FEATURE:
<223> OTHER INFORMATION: synthetic

<400> SEQUENCE: 48

Cys Leu Ser Glu Glu Asn Thr Ser Leu Ser Ser Thr Thr Asn Cys Met
1               5                   10                  15

Asp Ile Leu Ser Glu Glu Asn Thr Ser Leu Ser Ser Cys
            20                  25

<210> SEQ ID NO 49
<211> LENGTH: 29
<212> TYPE: PRT
<213> ORGANISM: Artificial Sequence
<220> FEATURE:
<223> OTHER INFORMATION: synthetic

<400> SEQUENCE: 49

Cys Leu Thr Ile Leu Tyr Gly Tyr Arg Trp Pro Leu Pro Ser Cys Leu
1               5                   10                  15

Tyr Gly Tyr Arg Trp Pro Leu Pro Ser Lys Leu Ser Cys
            20                  25

<210> SEQ ID NO 50
```

<211> LENGTH: 17
<212> TYPE: PRT
<213> ORGANISM: Artificial Sequence
<220> FEATURE:
<223> OTHER INFORMATION: synthetic

<400> SEQUENCE: 50

Cys Leu Thr Ile Leu Tyr Gly Tyr Arg Trp Pro Ala Ala Ser Lys Leu
1               5                   10                  15

Cys

<210> SEQ ID NO 51
<211> LENGTH: 29
<212> TYPE: PRT
<213> ORGANISM: Artificial Sequence
<220> FEATURE:
<223> OTHER INFORMATION: synthetic

<400> SEQUENCE: 51

Cys Thr Arg Leu Tyr Ser Asn Asp Phe Asn Ser Gly Glu Ala Cys Lys
1               5                   10                  15

Glu Ser Ser Asn Glu Asp Val Ile Gly Ala Leu Leu Cys
            20                  25

<210> SEQ ID NO 52
<211> LENGTH: 29
<212> TYPE: PRT
<213> ORGANISM: Artificial Sequence
<220> FEATURE:
<223> OTHER INFORMATION: synthetic

<400> SEQUENCE: 52

Cys Leu Tyr Gly Tyr Arg Trp Pro Leu Pro Ser Lys Leu Ser Cys Ser
1               5                   10                  15

Gly Glu Ala Asn Thr Ser Asp Ala Phe Asn Trp Thr Cys
            20                  25

<210> SEQ ID NO 53
<211> LENGTH: 29
<212> TYPE: PRT
<213> ORGANISM: Artificial Sequence
<220> FEATURE:
<223> OTHER INFORMATION: synthetic

<400> SEQUENCE: 53

Cys Met Asp Ile Leu Ser Glu Glu Asn Thr Ser Leu Ser Ser Cys Ser
1               5                   10                  15

Lys Glu Ser Ser Asn Glu Asp Val Ile Gly Ala Leu Cys
            20                  25

<210> SEQ ID NO 54
<211> LENGTH: 29
<212> TYPE: PRT
<213> ORGANISM: Artificial Sequence
<220> FEATURE:
<223> OTHER INFORMATION: synthetic

<400> SEQUENCE: 54

Cys Ser Ser Leu Ser Leu Leu His Leu Gln Lys Asn Trp Cys Met
1               5                   10                  15

Asp Ile Leu Ser Glu Glu Asn Thr Ser Leu Ser Ser Cys
            20                  25

<210> SEQ ID NO 55

```
<211> LENGTH: 29
<212> TYPE: PRT
<213> ORGANISM: Artificial Sequence
<220> FEATURE:
<223> OTHER INFORMATION: synthetic

<400> SEQUENCE: 55

Cys Asp Ser Lys Val Phe Lys Glu Gly Ser Ser Leu Leu Ala Cys Ser
1               5                   10                  15

Glu Asn Arg Thr Asn Leu Ser Ser Glu Gly Ser Leu Cys
            20                  25

<210> SEQ ID NO 56
<211> LENGTH: 29
<212> TYPE: PRT
<213> ORGANISM: Artificial Sequence
<220> FEATURE:
<223> OTHER INFORMATION: synthetic

<400> SEQUENCE: 56

Cys Val Phe Lys Glu Gly Ser Ser Leu Leu Ala Asp Asp Asn Cys Ser
1               5                   10                  15

Asp Ala Phe Asn Trp Thr Val Asp Ser Glu Asn Arg Cys
            20                  25

<210> SEQ ID NO 57
<211> LENGTH: 29
<212> TYPE: PRT
<213> ORGANISM: Artificial Sequence
<220> FEATURE:
<223> OTHER INFORMATION: synthetic

<400> SEQUENCE: 57

Cys Leu Gln Asp Asp Ser Lys Val Phe Lys Glu Gly Ser Ser Cys Lys
1               5                   10                  15

Glu Ser Ser Asn Glu Asp Val Ile Gly Ala Leu Leu Cys
            20                  25

<210> SEQ ID NO 58
<211> LENGTH: 9
<212> TYPE: PRT
<213> ORGANISM: Artificial Sequence
<220> FEATURE:
<223> OTHER INFORMATION: synthetic

<400> SEQUENCE: 58

Asn Phe Ala Arg Lys Arg Ile Lys Asn
1               5

<210> SEQ ID NO 59
<211> LENGTH: 9
<212> TYPE: PRT
<213> ORGANISM: Artificial Sequence
<220> FEATURE:
<223> OTHER INFORMATION: synthetic

<400> SEQUENCE: 59

Leu Asn Phe Ala Arg Lys Arg Ile Lys
1               5

<210> SEQ ID NO 60
<211> LENGTH: 11
<212> TYPE: PRT
<213> ORGANISM: Artificial Sequence
<220> FEATURE:
<223> OTHER INFORMATION: synthetic
```

<400> SEQUENCE: 60

Cys Asn Phe Ala Arg Lys Arg Ile Lys Asn Cys
1               5                   10

<210> SEQ ID NO 61
<211> LENGTH: 33
<212> TYPE: PRT
<213> ORGANISM: Artificial Sequence
<220> FEATURE:
<223> OTHER INFORMATION: synthetic

<400> SEQUENCE: 61

Cys Ser Tyr Leu Asn Phe Ala Arg Lys Arg Ile Lys Asn Pro Glu Gly
1               5                   10                  15

Cys Gln Asn Glu Ser Tyr Leu Asn Phe Ala Arg Lys Arg Ile Lys Asn
            20                  25                  30

Cys

<210> SEQ ID NO 62
<211> LENGTH: 15
<212> TYPE: PRT
<213> ORGANISM: Artificial Sequence
<220> FEATURE:
<223> OTHER INFORMATION: synthetic

<400> SEQUENCE: 62

Asn Glu Ser Tyr Leu Asn Phe Ala Arg Lys Ala Ala Lys Asn Pro
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: synthetic

<400> SEQUENCE: 63

Gln Asn Glu Ser Tyr Leu Asn Phe Ala Arg Lys Arg Ile Lys Asn
1               5                   10                  15

<210> SEQ ID NO 64
<211> LENGTH: 33
<212> TYPE: PRT
<213> ORGANISM: Artificial Sequence
<220> FEATURE:
<223> OTHER INFORMATION: synthetic

<400> SEQUENCE: 64

Cys Val Ser Glu Gln Lys Ile Ser Glu Trp Gly Lys Ile Lys Glu Ser
1               5                   10                  15

Cys Gln Asn Glu Ser Tyr Leu Asn Phe Ala Arg Lys Arg Ile Lys Asn
            20                  25                  30

Cys

<210> SEQ ID NO 65
<211> LENGTH: 33
<212> TYPE: PRT
<213> ORGANISM: Artificial Sequence
<220> FEATURE:
<223> OTHER INFORMATION: synthetic

<400> SEQUENCE: 65

Cys Asn Phe Ala Arg Lys Arg Ile Lys Asn Pro Glu Gly Gly Leu Tyr

```
                1               5                  10                  15
Cys Gln Asn Glu Ser Tyr Leu Asn Phe Ala Arg Lys Arg Ile Lys Asn
            20                  25                  30

Cys

<210> SEQ ID NO 66
<211> LENGTH: 33
<212> TYPE: PRT
<213> ORGANISM: Artificial Sequence
<220> FEATURE:
<223> OTHER INFORMATION: synthetic

<400> SEQUENCE: 66

Cys Val Arg Gly Gln Thr Ala Glu Ser Leu Ala Val His Asn Ile Thr
1               5                  10                  15

Cys Gln Asn Glu Ser Tyr Leu Asn Phe Ala Arg Lys Arg Ile Lys Asn
            20                  25                  30

Cys

<210> SEQ ID NO 67
<211> LENGTH: 9
<212> TYPE: PRT
<213> ORGANISM: Artificial Sequence
<220> FEATURE:
<223> OTHER INFORMATION: synthetic

<400> SEQUENCE: 67

Phe Ala Arg Lys Arg Ile Lys Asn Pro
1               5

<210> SEQ ID NO 68
<211> LENGTH: 15
<212> TYPE: PRT
<213> ORGANISM: Artificial Sequence
<220> FEATURE:
<223> OTHER INFORMATION: synthetic

<400> SEQUENCE: 68

Gly Asp Arg Gln Asn Glu Ser Tyr Leu Asn Ala Gly Arg Lys Arg
1               5                  10                  15

<210> SEQ ID NO 69
<211> LENGTH: 33
<212> TYPE: PRT
<213> ORGANISM: Artificial Sequence
<220> FEATURE:
<223> OTHER INFORMATION: synthetic

<400> SEQUENCE: 69

Cys Gln Lys Ile Ser Glu Trp Gly Lys Ile Lys Glu Ser Pro Ile Pro
1               5                  10                  15

Cys Gln Asn Glu Ser Tyr Leu Asn Phe Ala Arg Lys Arg Ile Lys Asn
            20                  25                  30

Cys

<210> SEQ ID NO 70
<211> LENGTH: 33
<212> TYPE: PRT
<213> ORGANISM: Artificial Sequence
<220> FEATURE:
<223> OTHER INFORMATION: synthetic

<400> SEQUENCE: 70
```

```
Cys Gly Asp Arg Gln Asn Glu Ser Tyr Leu Asn Phe Ala Arg Lys Arg
1               5                   10                  15

Cys Gln Asn Glu Ser Tyr Leu Asn Phe Ala Arg Lys Arg Ile Lys Asn
                20                  25                  30

Cys

<210> SEQ ID NO 71
<211> LENGTH: 15
<212> TYPE: PRT
<213> ORGANISM: Artificial Sequence
<220> FEATURE:
<223> OTHER INFORMATION: synthetic

<400> SEQUENCE: 71

Ser Tyr Leu Asn Phe Ala Arg Lys Arg Ile Ala Ala Pro Glu Gly
1               5                   10                  15

<210> SEQ ID NO 72
<211> LENGTH: 33
<212> TYPE: PRT
<213> ORGANISM: Artificial Sequence
<220> FEATURE:
<223> OTHER INFORMATION: synthetic

<400> SEQUENCE: 72

Cys Glu Trp Ser Val Asn Ala Arg Val Asn Asn Ser Asp Pro Tyr Ser
1               5                   10                  15

Cys Pro Tyr Ser Val Ala Leu Ser Glu Leu Gly Asp Arg Gln Asn Glu
                20                  25                  30

Cys

<210> SEQ ID NO 73
<211> LENGTH: 33
<212> TYPE: PRT
<213> ORGANISM: Artificial Sequence
<220> FEATURE:
<223> OTHER INFORMATION: synthetic

<400> SEQUENCE: 73

Cys His Gly Ala Glu Arg Ile Val Arg Gly Gln Thr Ala Glu Ser Leu
1               5                   10                  15

Cys Gln Asn Glu Ser Tyr Leu Asn Phe Ala Arg Lys Arg Ile Lys Asn
                20                  25                  30

Cys

<210> SEQ ID NO 74
<211> LENGTH: 33
<212> TYPE: PRT
<213> ORGANISM: Artificial Sequence
<220> FEATURE:
<223> OTHER INFORMATION: synthetic

<400> SEQUENCE: 74

Cys Glu Ser Leu Ala Val His Asn Ile Thr Val Ser Glu Gln Lys Ile
1               5                   10                  15

Cys Gln Asn Glu Ser Tyr Leu Asn Phe Ala Arg Lys Arg Ile Lys Asn
                20                  25                  30

Cys

<210> SEQ ID NO 75
<211> LENGTH: 33
<212> TYPE: PRT
```

<213> ORGANISM: Artificial Sequence
<220> FEATURE:
<223> OTHER INFORMATION: synthetic

<400> SEQUENCE: 75

Cys Glu Arg Ile Val Arg Gly Gln Thr Ala Glu Ser Leu Ala Val His
1               5                   10                  15
Cys Gln Asn Glu Ser Tyr Leu Asn Phe Ala Arg Lys Arg Ile Lys Asn
            20                  25                  30
Cys

<210> SEQ ID NO 76
<211> LENGTH: 15
<212> TYPE: PRT
<213> ORGANISM: Artificial Sequence
<220> FEATURE:
<223> OTHER INFORMATION: synthetic

<400> SEQUENCE: 76

Arg Gln Asn Glu Ser Tyr Leu Asn Phe Ala Arg Lys Arg Ile Lys
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: synthetic

<400> SEQUENCE: 77

Asn Phe Ala Arg Lys Arg Ile Lys Asn Pro Ala Ala Gly Leu Tyr
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: synthetic

<400> SEQUENCE: 78

Asp Pro Tyr Ser Val Ala Leu Ser Glu Leu Ala Ala Arg Gln Asn
1               5                   10                  15

<210> SEQ ID NO 79
<211> LENGTH: 33
<212> TYPE: PRT
<213> ORGANISM: Artificial Sequence
<220> FEATURE:
<223> OTHER INFORMATION: synthetic

<400> SEQUENCE: 79

Cys Glu Ser Leu Ala Val His Asn Ile Thr Val Ser Glu Gln Lys Ile
1               5                   10                  15
Cys Ser Tyr Leu Asn Phe Ala Arg Lys Arg Ile Lys Asn Pro Glu Gly
            20                  25                  30
Cys

<210> SEQ ID NO 80
<211> LENGTH: 33
<212> TYPE: PRT
<213> ORGANISM: Artificial Sequence
<220> FEATURE:
<223> OTHER INFORMATION: synthetic

```
<400> SEQUENCE: 80

Cys Ser Glu Leu Gly Asp Arg Gln Asn Glu Ser Tyr Leu Asn Phe Ala
1               5                   10                  15

Cys Gln Asn Glu Ser Tyr Leu Asn Phe Ala Arg Lys Arg Ile Lys Asn
                20                  25                  30

Cys

<210> SEQ ID NO 81
<211> LENGTH: 33
<212> TYPE: PRT
<213> ORGANISM: Artificial Sequence
<220> FEATURE:
<223> OTHER INFORMATION: synthetic

<400> SEQUENCE: 81

Cys Asn Ile Thr Val Ser Glu Gln Lys Ile Ser Glu Trp Gly Lys Ile
1               5                   10                  15

Cys Gln Asn Glu Ser Tyr Leu Asn Phe Ala Arg Lys Arg Ile Lys Asn
                20                  25                  30

Cys

<210> SEQ ID NO 82
<211> LENGTH: 33
<212> TYPE: PRT
<213> ORGANISM: Artificial Sequence
<220> FEATURE:
<223> OTHER INFORMATION: synthetic

<400> SEQUENCE: 82

Cys His Gly Ala Glu Arg Ile Val Arg Gly Gln Thr Ala Glu Ser Leu
1               5                   10                  15

Cys Ser Tyr Leu Asn Phe Ala Arg Lys Arg Ile Lys Asn Pro Glu Gly
                20                  25                  30

Cys

<210> SEQ ID NO 83
<211> LENGTH: 9
<212> TYPE: PRT
<213> ORGANISM: Artificial Sequence
<220> FEATURE:
<223> OTHER INFORMATION: synthetic

<400> SEQUENCE: 83

Lys Ile Ser Glu Trp Gly Lys Ile Lys
1               5

<210> SEQ ID NO 84
<211> LENGTH: 33
<212> TYPE: PRT
<213> ORGANISM: Artificial Sequence
<220> FEATURE:
<223> OTHER INFORMATION: synthetic

<400> SEQUENCE: 84

Cys Val Ser Glu Gln Lys Ile Ser Glu Trp Gly Lys Ile Lys Glu Ser
1               5                   10                  15

Cys Glu Gln Lys Ile Ser Glu Trp Gly Lys Ile Lys Glu Ser Pro Ile
                20                  25                  30

Cys

<210> SEQ ID NO 85
```

<211> LENGTH: 33
<212> TYPE: PRT
<213> ORGANISM: Artificial Sequence
<220> FEATURE:
<223> OTHER INFORMATION: synthetic

<400> SEQUENCE: 85

Cys Gly Asp Arg Gln Asn Glu Ser Tyr Leu Asn Phe Ala Arg Lys Arg
1               5                   10                  15

Cys Gly Asp Arg Gln Asn Glu Ser Tyr Leu Asn Phe Ala Arg Lys Arg
            20                  25                  30

Cys

<210> SEQ ID NO 86
<211> LENGTH: 17
<212> TYPE: PRT
<213> ORGANISM: Artificial Sequence
<220> FEATURE:
<223> OTHER INFORMATION: synthetic

<400> SEQUENCE: 86

Cys Asn Glu Ser Tyr Leu Asn Phe Ala Arg Lys Ala Ala Lys Asn Pro
1               5                   10                  15

Cys

<210> SEQ ID NO 87
<211> LENGTH: 11
<212> TYPE: PRT
<213> ORGANISM: Artificial Sequence
<220> FEATURE:
<223> OTHER INFORMATION: synthetic

<400> SEQUENCE: 87

Cys Leu Asn Phe Ala Arg Lys Arg Ile Lys Cys
1               5                   10

<210> SEQ ID NO 88
<211> LENGTH: 15
<212> TYPE: PRT
<213> ORGANISM: Artificial Sequence
<220> FEATURE:
<223> OTHER INFORMATION: synthetic

<400> SEQUENCE: 88

Gln Lys Ile Ser Glu Trp Gly Lys Ile Lys Ala Ala Pro Ile Pro
1               5                   10                  15

<210> SEQ ID NO 89
<211> LENGTH: 33
<212> TYPE: PRT
<213> ORGANISM: Artificial Sequence
<220> FEATURE:
<223> OTHER INFORMATION: synthetic

<400> SEQUENCE: 89

Cys His Gly Ala Glu Arg Ile Val Arg Gly Gln Thr Ala Glu Ser Leu
1               5                   10                  15

Cys Asn Phe Ala Arg Lys Arg Ile Lys Asn Pro Glu Gly Gly Leu Tyr
            20                  25                  30

Cys

<210> SEQ ID NO 90
<211> LENGTH: 17
<212> TYPE: PRT

<213> ORGANISM: Artificial Sequence
<220> FEATURE:
<223> OTHER INFORMATION: synthetic

<400> SEQUENCE: 90

Cys Gln Asn Glu Ser Tyr Leu Asn Phe Ala Arg Lys Arg Ile Lys Asn
1               5                   10                  15

Cys

<210> SEQ ID NO 91
<211> LENGTH: 15
<212> TYPE: PRT
<213> ORGANISM: Artificial Sequence
<220> FEATURE:
<223> OTHER INFORMATION: synthetic

<400> SEQUENCE: 91

Leu Asn Phe Ala Arg Lys Arg Ile Lys Asn Ala Ala Gly Gly Leu
1               5                   10                  15

<210> SEQ ID NO 92
<211> LENGTH: 17
<212> TYPE: PRT
<213> ORGANISM: Artificial Sequence
<220> FEATURE:
<223> OTHER INFORMATION: synthetic

<400> SEQUENCE: 92

Cys Leu Asn Phe Ala Arg Lys Arg Ile Lys Asn Ala Ala Gly Gly Leu
1               5                   10                  15

Cys

<210> SEQ ID NO 93
<211> LENGTH: 33
<212> TYPE: PRT
<213> ORGANISM: Artificial Sequence
<220> FEATURE:
<223> OTHER INFORMATION: synthetic

<400> SEQUENCE: 93

Cys Gln Lys Ile Ser Glu Trp Gly Lys Ile Lys Glu Ser Pro Ile Pro
1               5                   10                  15

Cys Thr Val Ser Glu Gln Lys Ile Ser Glu Trp Gly Lys Ile Lys Glu
                20                  25                  30

Cys

<210> SEQ ID NO 94
<211> LENGTH: 15
<212> TYPE: PRT
<213> ORGANISM: Artificial Sequence
<220> FEATURE:
<223> OTHER INFORMATION: synthetic

<400> SEQUENCE: 94

Thr Val Cys Glu Gln Lys Ile Ser Glu Trp Gly Lys Ile Lys Glu
1               5                   10                  15

<210> SEQ ID NO 95
<211> LENGTH: 17
<212> TYPE: PRT
<213> ORGANISM: Artificial Sequence
<220> FEATURE:
<223> OTHER INFORMATION: synthetic

<400> SEQUENCE: 95

Cys Arg Gln Asn Glu Ser Tyr Leu Asn Phe Ala Arg Lys Arg Ile Lys
1               5                   10                  15

Cys

<210> SEQ ID NO 96
<211> LENGTH: 15
<212> TYPE: PRT
<213> ORGANISM: Artificial Sequence
<220> FEATURE:
<223> OTHER INFORMATION: synthetic

<400> SEQUENCE: 96

Asn Ile Thr Val Cys Glu Gln Lys Ile Ser Ala Ala Gly Lys Ile
1               5                   10                  15

<210> SEQ ID NO 97
<211> LENGTH: 33
<212> TYPE: PRT
<213> ORGANISM: Artificial Sequence
<220> FEATURE:
<223> OTHER INFORMATION: synthetic

<400> SEQUENCE: 97

Cys Asn Phe Ala Arg Lys Arg Ile Lys Asn Pro Glu Gly Gly Leu Tyr
1               5                   10                  15

Cys Ser Tyr Leu Asn Phe Ala Arg Lys Arg Ile Lys Asn Pro Glu Gly
            20                  25                  30

Cys

<210> SEQ ID NO 98
<211> LENGTH: 33
<212> TYPE: PRT
<213> ORGANISM: Artificial Sequence
<220> FEATURE:
<223> OTHER INFORMATION: synthetic

<400> SEQUENCE: 98

Cys Gln Lys Ile Ser Glu Trp Gly Lys Ile Lys Glu Ser Pro Ile Pro
1               5                   10                  15

Cys Val Ser Glu Gln Lys Ile Ser Glu Trp Gly Lys Ile Lys Glu Ser
            20                  25                  30

Cys

<210> SEQ ID NO 99
<211> LENGTH: 33
<212> TYPE: PRT
<213> ORGANISM: Artificial Sequence
<220> FEATURE:
<223> OTHER INFORMATION: synthetic

<400> SEQUENCE: 99

Cys Asn Ile Thr Val Ser Glu Gln Lys Ile Ser Glu Trp Gly Lys Ile
1               5                   10                  15

Cys Ser Tyr Leu Asn Phe Ala Arg Lys Arg Ile Lys Asn Pro Glu Gly
            20                  25                  30

Cys

<210> SEQ ID NO 100
<211> LENGTH: 33
<212> TYPE: PRT
<213> ORGANISM: Artificial Sequence
<220> FEATURE:

<223> OTHER INFORMATION: synthetic

<400> SEQUENCE: 100

Cys Gln Thr Ala Glu Ser Leu Ala Val His Asn Ile Thr Val Ser Glu
1               5                   10                  15

Cys Gln Asn Glu Ser Tyr Leu Asn Phe Ala Arg Lys Arg Ile Lys Asn
            20                  25                  30

Cys

<210> SEQ ID NO 101
<211> LENGTH: 33
<212> TYPE: PRT
<213> ORGANISM: Artificial Sequence
<220> FEATURE:
<223> OTHER INFORMATION: synthetic

<400> SEQUENCE: 101

Cys His Gly Ala Glu Arg Ile Val Arg Gly Gln Thr Ala Glu Ser Leu
1               5                   10                  15

Cys Gln Lys Ile Ser Glu Trp Gly Lys Ile Lys Glu Ser Pro Ile Pro
            20                  25                  30

Cys

<210> SEQ ID NO 102
<211> LENGTH: 9
<212> TYPE: PRT
<213> ORGANISM: Artificial Sequence
<220> FEATURE:
<223> OTHER INFORMATION: synthetic

<400> SEQUENCE: 102

Gly Lys Ile Lys Glu Cys Pro Ile Pro
1               5

<210> SEQ ID NO 103
<211> LENGTH: 33
<212> TYPE: PRT
<213> ORGANISM: Artificial Sequence
<220> FEATURE:
<223> OTHER INFORMATION: synthetic

<400> SEQUENCE: 103

Cys Glu Trp Ser Val Asn Ala Arg Val Asn Asn Ser Asp Pro Tyr Ser
1               5                   10                  15

Cys Gln Asn Glu Ser Tyr Leu Asn Phe Ala Arg Lys Arg Ile Lys Asn
            20                  25                  30

Cys

<210> SEQ ID NO 104
<211> LENGTH: 15
<212> TYPE: PRT
<213> ORGANISM: Artificial Sequence
<220> FEATURE:
<223> OTHER INFORMATION: synthetic

<400> SEQUENCE: 104

Leu Gly Asp Arg Gln Asn Glu Ser Tyr Leu Asn Phe Ala Arg Lys
1               5                   10                  15

<210> SEQ ID NO 105
<211> LENGTH: 17
<212> TYPE: PRT
<213> ORGANISM: Artificial Sequence

```
<220> FEATURE:
<223> OTHER INFORMATION: synthetic

<400> SEQUENCE: 105

Cys Asn Ile Thr Val Ser Glu Gln Lys Ile Ser Ala Ala Gly Lys Ile
1               5                   10                  15

Cys

<210> SEQ ID NO 106
<211> LENGTH: 33
<212> TYPE: PRT
<213> ORGANISM: Artificial Sequence
<220> FEATURE:
<223> OTHER INFORMATION: synthetic

<400> SEQUENCE: 106

Cys Asn Phe Ala Arg Lys Arg Ile Lys Asn Pro Glu Gly Gly Leu Tyr
1               5                   10                  15

Cys Ser Leu Ala Val His Asn Ile Thr Val Ser Glu Gln Lys Ile Ser
            20                  25                  30

Cys

<210> SEQ ID NO 107
<211> LENGTH: 9
<212> TYPE: PRT
<213> ORGANISM: Artificial Sequence
<220> FEATURE:
<223> OTHER INFORMATION: synthetic

<400> SEQUENCE: 107

Glu Ser Tyr Leu Asn Phe Ala Arg Lys
1               5

<210> SEQ ID NO 108
<211> LENGTH: 11
<212> TYPE: PRT
<213> ORGANISM: Artificial Sequence
<220> FEATURE:
<223> OTHER INFORMATION: synthetic

<400> SEQUENCE: 108

Cys Lys Ile Ser Glu Trp Gly Lys Ile Lys Cys
1               5                   10

<210> SEQ ID NO 109
<211> LENGTH: 15
<212> TYPE: PRT
<213> ORGANISM: Artificial Sequence
<220> FEATURE:
<223> OTHER INFORMATION: synthetic

<400> SEQUENCE: 109

Asn Glu Ser Tyr Leu Asn Phe Ala Arg Lys Arg Ile Lys Asn Pro
1               5                   10                  15

<210> SEQ ID NO 110
<211> LENGTH: 33
<212> TYPE: PRT
<213> ORGANISM: Artificial Sequence
<220> FEATURE:
<223> OTHER INFORMATION: synthetic

<400> SEQUENCE: 110

Cys Val Ala Leu Ser Glu Leu Gly Asp Arg Gln Asn Glu Ser Tyr Leu
1               5                   10                  15
```

-continued

Cys Gln Asn Glu Ser Tyr Leu Asn Phe Ala Arg Lys Arg Ile Lys Asn
            20                  25                  30

Cys

<210> SEQ ID NO 111
<211> LENGTH: 33
<212> TYPE: PRT
<213> ORGANISM: Artificial Sequence
<220> FEATURE:
<223> OTHER INFORMATION: synthetic

<400> SEQUENCE: 111

Cys Gln Asn Glu Ser Tyr Leu Asn Phe Ala Arg Lys Arg Ile Lys Asn
1               5                   10                  15

Cys Val Ser Glu Gln Lys Ile Ser Glu Trp Gly Lys Ile Lys Glu Ser
            20                  25                  30

Cys

<210> SEQ ID NO 112
<211> LENGTH: 33
<212> TYPE: PRT
<213> ORGANISM: Artificial Sequence
<220> FEATURE:
<223> OTHER INFORMATION: synthetic

<400> SEQUENCE: 112

Cys Val Ser Glu Gln Lys Ile Ser Glu Trp Gly Lys Ile Lys Glu Ser
1               5                   10                  15

Cys Gly Asp Arg Gln Asn Glu Ser Tyr Leu Asn Phe Ala Arg Lys Arg
            20                  25                  30

Cys

<210> SEQ ID NO 113
<211> LENGTH: 15
<212> TYPE: PRT
<213> ORGANISM: Artificial Sequence
<220> FEATURE:
<223> OTHER INFORMATION: synthetic

<400> SEQUENCE: 113

Gln Asn Glu Ser Tyr Leu Asn Phe Ala Arg Ala Ala Ile Lys Asn
1               5                   10                  15

<210> SEQ ID NO 114
<211> LENGTH: 17
<212> TYPE: PRT
<213> ORGANISM: Artificial Sequence
<220> FEATURE:
<223> OTHER INFORMATION: synthetic

<400> SEQUENCE: 114

Cys Ser Glu Gln Lys Ile Ser Glu Trp Gly Lys Ile Lys Glu Ser Pro
1               5                   10                  15

Cys

<210> SEQ ID NO 115
<211> LENGTH: 33
<212> TYPE: PRT
<213> ORGANISM: Artificial Sequence
<220> FEATURE:
<223> OTHER INFORMATION: synthetic

<400> SEQUENCE: 115

```
Cys Val Ser Glu Gln Lys Ile Ser Glu Trp Gly Lys Ile Lys Glu Ser
1               5                   10                  15

Cys Val Ser Glu Gln Lys Ile Ser Glu Trp Gly Lys Ile Lys Glu Ser
                20                  25                  30

Cys
```

<210> SEQ ID NO 116
<211> LENGTH: 9
<212> TYPE: PRT
<213> ORGANISM: Artificial Sequence
<220> FEATURE:
<223> OTHER INFORMATION: synthetic

<400> SEQUENCE: 116

```
Trp Gly Lys Ile Lys Glu Cys Pro Ile
1               5
```

<210> SEQ ID NO 117
<211> LENGTH: 33
<212> TYPE: PRT
<213> ORGANISM: Artificial Sequence
<220> FEATURE:
<223> OTHER INFORMATION: synthetic

<400> SEQUENCE: 117

```
Cys Asn Phe Ala Arg Lys Arg Ile Lys Asn Pro Glu Gly Gly Leu Tyr
1               5                   10                  15

Cys Gly Asp Arg Gln Asn Glu Ser Tyr Leu Asn Phe Ala Arg Lys Arg
                20                  25                  30

Cys
```

<210> SEQ ID NO 118
<211> LENGTH: 15
<212> TYPE: PRT
<213> ORGANISM: Artificial Sequence
<220> FEATURE:
<223> OTHER INFORMATION: synthetic

<400> SEQUENCE: 118

```
Val Asn Ala Arg Val Asn Ser Asp Pro Ala Ala Val Ala Leu
1               5                   10              15
```

<210> SEQ ID NO 119
<211> LENGTH: 15
<212> TYPE: PRT
<213> ORGANISM: Artificial Sequence
<220> FEATURE:
<223> OTHER INFORMATION: synthetic

<400> SEQUENCE: 119

```
Tyr Leu Asn Phe Ala Arg Lys Arg Ile Lys Ala Ala Glu Gly Gly
1               5                   10                  15
```

<210> SEQ ID NO 120
<211> LENGTH: 15
<212> TYPE: PRT
<213> ORGANISM: Artificial Sequence
<220> FEATURE:
<223> OTHER INFORMATION: synthetic

<400> SEQUENCE: 120

```
Gly Asp Arg Gln Asn Glu Ser Tyr Leu Asn Phe Ala Arg Lys Arg
1               5                   10                  15
```

```
<210> SEQ ID NO 121
<211> LENGTH: 15
<212> TYPE: PRT
<213> ORGANISM: Artificial Sequence
<220> FEATURE:
<223> OTHER INFORMATION: synthetic

<400> SEQUENCE: 121

Trp Cys Val Asn Ala Arg Val Asn Asn Ser Asp Pro Tyr Ser Val
1               5                   10                  15

<210> SEQ ID NO 122
<211> LENGTH: 33
<212> TYPE: PRT
<213> ORGANISM: Artificial Sequence
<220> FEATURE:
<223> OTHER INFORMATION: synthetic

<400> SEQUENCE: 122

Cys Ser Tyr Leu Asn Phe Ala Arg Lys Arg Ile Lys Asn Pro Glu Gly
1               5                   10                  15

Cys Ile Thr Val Ser Glu Gln Lys Ile Ser Glu Trp Gly Lys Ile Lys
            20                  25                  30

Cys

<210> SEQ ID NO 123
<211> LENGTH: 33
<212> TYPE: PRT
<213> ORGANISM: Artificial Sequence
<220> FEATURE:
<223> OTHER INFORMATION: synthetic

<400> SEQUENCE: 123

Cys Ala Val His Asn Ile Thr Val Ser Glu Gln Lys Ile Ser Glu Trp
1               5                   10                  15

Cys Val Ser Glu Gln Lys Ile Ser Glu Trp Gly Lys Ile Lys Glu Ser
            20                  25                  30

Cys

<210> SEQ ID NO 124
<211> LENGTH: 33
<212> TYPE: PRT
<213> ORGANISM: Artificial Sequence
<220> FEATURE:
<223> OTHER INFORMATION: synthetic

<400> SEQUENCE: 124

Cys Pro Tyr Ser Val Ala Leu Ser Glu Leu Gly Asp Arg Gln Asn Glu
1               5                   10                  15

Cys Ile Thr Val Ser Glu Gln Lys Ile Ser Glu Trp Gly Lys Ile Lys
            20                  25                  30

Cys

<210> SEQ ID NO 125
<211> LENGTH: 33
<212> TYPE: PRT
<213> ORGANISM: Artificial Sequence
<220> FEATURE:
<223> OTHER INFORMATION: synthetic

<400> SEQUENCE: 125

Cys Ser Tyr Leu Asn Phe Ala Arg Lys Arg Ile Lys Asn Pro Glu Gly
1               5                   10                  15
```

Cys Gly Asp Arg Gln Asn Glu Ser Tyr Leu Asn Phe Ala Arg Lys Arg
            20                  25                  30

Cys

<210> SEQ ID NO 126
<211> LENGTH: 33
<212> TYPE: PRT
<213> ORGANISM: Artificial Sequence
<220> FEATURE:
<223> OTHER INFORMATION: synthetic

<400> SEQUENCE: 126

Cys Ala Val His Asn Ile Thr Val Ser Glu Gln Lys Ile Ser Glu Trp
1               5                   10                  15

Cys Gln Asn Glu Ser Tyr Leu Asn Phe Ala Arg Lys Arg Ile Lys Asn
            20                  25                  30

Cys

<210> SEQ ID NO 127
<211> LENGTH: 15
<212> TYPE: PRT
<213> ORGANISM: Artificial Sequence
<220> FEATURE:
<223> OTHER INFORMATION: synthetic

<400> SEQUENCE: 127

Leu Gly Asp Arg Gln Asn Glu Ser Tyr Leu Ala Ala Ala Arg Lys
1               5                   10                  15

<210> SEQ ID NO 128
<211> LENGTH: 33
<212> TYPE: PRT
<213> ORGANISM: Artificial Sequence
<220> FEATURE:
<223> OTHER INFORMATION: synthetic

<400> SEQUENCE: 128

Cys Val Asn Ala Arg Val Asn Asn Ser Asp Pro Tyr Ser Val Ala Leu
1               5                   10                  15

Cys Val Ser Glu Gln Lys Ile Ser Glu Trp Gly Lys Ile Lys Glu Ser
            20                  25                  30

Cys

<210> SEQ ID NO 129
<211> LENGTH: 33
<212> TYPE: PRT
<213> ORGANISM: Artificial Sequence
<220> FEATURE:
<223> OTHER INFORMATION: synthetic

<400> SEQUENCE: 129

Cys Phe Asn Val Glu Trp Ser Val Asn Ala Arg Val Asn Asn Ser Asp
1               5                   10                  15

Cys Gly Asp Arg Gln Asn Glu Ser Tyr Leu Asn Phe Ala Arg Lys Arg
            20                  25                  30

Cys

<210> SEQ ID NO 130
<211> LENGTH: 33
<212> TYPE: PRT
<213> ORGANISM: Artificial Sequence
<220> FEATURE:

<223> OTHER INFORMATION: synthetic

<400> SEQUENCE: 130

Cys Asn Ser Asp Pro Tyr Ser Val Ala Leu Ser Glu Leu Gly Asp Arg
1               5                   10                  15

Cys Val Ser Glu Gln Lys Ile Ser Glu Trp Gly Lys Ile Lys Glu Ser
            20                  25                  30

Cys

<210> SEQ ID NO 131
<211> LENGTH: 33
<212> TYPE: PRT
<213> ORGANISM: Artificial Sequence
<220> FEATURE:
<223> OTHER INFORMATION: synthetic

<400> SEQUENCE: 131

Cys Gly Asp Arg Gln Asn Glu Ser Tyr Leu Asn Phe Ala Arg Lys Arg
1               5                   10                  15

Cys Ser Tyr Leu Asn Phe Ala Arg Lys Arg Ile Lys Asn Pro Glu Gly
            20                  25                  30

Cys

<210> SEQ ID NO 132
<211> LENGTH: 15
<212> TYPE: PRT
<213> ORGANISM: Artificial Sequence
<220> FEATURE:
<223> OTHER INFORMATION: synthetic

<400> SEQUENCE: 132

Asp Pro Tyr Ser Val Ala Leu Ser Glu Leu Gly Asp Arg Gln Asn
1               5                   10                  15

<210> SEQ ID NO 133
<211> LENGTH: 33
<212> TYPE: PRT
<213> ORGANISM: Artificial Sequence
<220> FEATURE:
<223> OTHER INFORMATION: synthetic

<400> SEQUENCE: 133

Cys Ala Val His Asn Ile Thr Val Ser Glu Gln Lys Ile Ser Glu Trp
1               5                   10                  15

Cys Ser Tyr Leu Asn Phe Ala Arg Lys Arg Ile Lys Asn Pro Glu Gly
            20                  25                  30

Cys

<210> SEQ ID NO 134
<211> LENGTH: 33
<212> TYPE: PRT
<213> ORGANISM: Artificial Sequence
<220> FEATURE:
<223> OTHER INFORMATION: synthetic

<400> SEQUENCE: 134

Cys Val Arg Gly Gln Thr Ala Glu Ser Leu Ala Val His Asn Ile Thr
1               5                   10                  15

Cys Ile Thr Val Ser Glu Gln Lys Ile Ser Glu Trp Gly Lys Ile Lys
            20                  25                  30

Cys

<210> SEQ ID NO 135
<211> LENGTH: 33
<212> TYPE: PRT
<213> ORGANISM: Artificial Sequence
<220> FEATURE:
<223> OTHER INFORMATION: synthetic

<400> SEQUENCE: 135

Cys Gln Asn Glu Ser Tyr Leu Asn Phe Ala Arg Lys Arg Ile Lys Asn
1               5                   10                  15

Cys Ser Tyr Leu Asn Phe Ala Arg Lys Arg Ile Lys Asn Pro Glu Gly
            20                  25                  30

Cys

<210> SEQ ID NO 136
<211> LENGTH: 33
<212> TYPE: PRT
<213> ORGANISM: Artificial Sequence
<220> FEATURE:
<223> OTHER INFORMATION: synthetic

<400> SEQUENCE: 136

Cys Glu Ser Leu Ala Val His Asn Ile Thr Val Ser Glu Gln Lys Ile
1               5                   10                  15

Cys Gly Asp Arg Gln Asn Glu Ser Tyr Leu Asn Phe Ala Arg Lys Arg
            20                  25                  30

Cys

<210> SEQ ID NO 137
<211> LENGTH: 33
<212> TYPE: PRT
<213> ORGANISM: Artificial Sequence
<220> FEATURE:
<223> OTHER INFORMATION: synthetic

<400> SEQUENCE: 137

Cys Arg Val Asn Asn Ser Asp Pro Tyr Ser Val Ala Leu Ser Glu Leu
1               5                   10                  15

Cys Gln Asn Glu Ser Tyr Leu Asn Phe Ala Arg Lys Arg Ile Lys Asn
            20                  25                  30

Cys

<210> SEQ ID NO 138
<211> LENGTH: 33
<212> TYPE: PRT
<213> ORGANISM: Artificial Sequence
<220> FEATURE:
<223> OTHER INFORMATION: synthetic

<400> SEQUENCE: 138

Cys Ser Tyr Leu Asn Phe Ala Arg Lys Arg Ile Lys Asn Pro Glu Gly
1               5                   10                  15

Cys Asn Phe Ala Arg Lys Arg Ile Lys Asn Pro Glu Gly Gly Leu Tyr
            20                  25                  30

Cys

<210> SEQ ID NO 139
<211> LENGTH: 33
<212> TYPE: PRT
<213> ORGANISM: Artificial Sequence
<220> FEATURE:
<223> OTHER INFORMATION: synthetic

<400> SEQUENCE: 139

Cys Gln Thr Ala Glu Ser Leu Ala Val His Asn Ile Thr Val Ser Glu
1               5                   10                  15

Cys Val Ser Glu Gln Lys Ile Ser Glu Trp Gly Lys Ile Lys Glu Ser
            20                  25                  30

Cys

<210> SEQ ID NO 140
<211> LENGTH: 9
<212> TYPE: PRT
<213> ORGANISM: Artificial Sequence
<220> FEATURE:
<223> OTHER INFORMATION: synthetic

<400> SEQUENCE: 140

Tyr Leu Asn Phe Ala Arg Lys Arg Ile
1               5

<210> SEQ ID NO 141
<211> LENGTH: 33
<212> TYPE: PRT
<213> ORGANISM: Artificial Sequence
<220> FEATURE:
<223> OTHER INFORMATION: synthetic

<400> SEQUENCE: 141

Cys Phe Asn Val Glu Trp Ser Val Asn Ala Arg Val Asn Asn Ser Asp
1               5                   10                  15

Cys Val Ser Glu Gln Lys Ile Ser Glu Trp Gly Lys Ile Lys Glu Ser
            20                  25                  30

Cys

<210> SEQ ID NO 142
<211> LENGTH: 33
<212> TYPE: PRT
<213> ORGANISM: Artificial Sequence
<220> FEATURE:
<223> OTHER INFORMATION: synthetic

<400> SEQUENCE: 142

Cys Val Ser Glu Gln Lys Ile Ser Glu Trp Gly Lys Ile Lys Glu Ser
1               5                   10                  15

Cys Thr Val Ser Glu Gln Lys Ile Ser Glu Trp Gly Lys Ile Lys Glu
            20                  25                  30

Cys

<210> SEQ ID NO 143
<211> LENGTH: 33
<212> TYPE: PRT
<213> ORGANISM: Artificial Sequence
<220> FEATURE:
<223> OTHER INFORMATION: synthetic

<400> SEQUENCE: 143

Cys Asn Ser Asp Pro Tyr Ser Val Ala Leu Ser Glu Leu Gly Asp Arg
1               5                   10                  15

Cys Ile Thr Val Ser Glu Gln Lys Ile Ser Glu Trp Gly Lys Ile Lys
            20                  25                  30

Cys

```
<210> SEQ ID NO 144
<211> LENGTH: 33
<212> TYPE: PRT
<213> ORGANISM: Artificial Sequence
<220> FEATURE:
<223> OTHER INFORMATION: synthetic

<400> SEQUENCE: 144

Cys Asn Ile Thr Val Ser Glu Gln Lys Ile Ser Glu Trp Gly Lys Ile
1               5                   10                  15

Cys Gly Asp Arg Gln Asn Glu Ser Tyr Leu Asn Phe Ala Arg Lys Arg
            20                  25                  30

Cys

<210> SEQ ID NO 145
<211> LENGTH: 17
<212> TYPE: PRT
<213> ORGANISM: Artificial Sequence
<220> FEATURE:
<223> OTHER INFORMATION: synthetic

<400> SEQUENCE: 145

Cys Leu Gly Asp Arg Gln Asn Glu Ser Tyr Leu Ala Ala Ala Arg Lys
1               5                   10                  15

Cys

<210> SEQ ID NO 146
<211> LENGTH: 9
<212> TYPE: PRT
<213> ORGANISM: Artificial Sequence
<220> FEATURE:
<223> OTHER INFORMATION: synthetic

<400> SEQUENCE: 146

Gln Lys Ile Ser Glu Trp Gly Lys Ile
1               5

<210> SEQ ID NO 147
<211> LENGTH: 17
<212> TYPE: PRT
<213> ORGANISM: Artificial Sequence
<220> FEATURE:
<223> OTHER INFORMATION: synthetic

<400> SEQUENCE: 147

Cys Ile Thr Val Ser Glu Gln Lys Ile Ser Glu Ala Ala Lys Ile Lys
1               5                   10                  15

Cys

<210> SEQ ID NO 148
<211> LENGTH: 33
<212> TYPE: PRT
<213> ORGANISM: Artificial Sequence
<220> FEATURE:
<223> OTHER INFORMATION: synthetic

<400> SEQUENCE: 148

Cys Val Arg Gly Gln Thr Ala Glu Ser Leu Ala Val His Asn Ile Thr
1               5                   10                  15

Cys Val His Asn Ile Thr Val Ser Glu Gln Lys Ile Ser Glu Trp Gly
            20                  25                  30

Cys
```

```
<210> SEQ ID NO 149
<211> LENGTH: 33
<212> TYPE: PRT
<213> ORGANISM: Artificial Sequence
<220> FEATURE:
<223> OTHER INFORMATION: synthetic

<400> SEQUENCE: 149

Cys Gln Lys Ile Ser Glu Trp Gly Lys Ile Lys Glu Ser Pro Ile Pro
1               5                   10                  15

Cys Val His Asn Ile Thr Val Ser Glu Gln Lys Ile Ser Glu Trp Gly
                20                  25                  30

Cys

<210> SEQ ID NO 150
<211> LENGTH: 33
<212> TYPE: PRT
<213> ORGANISM: Artificial Sequence
<220> FEATURE:
<223> OTHER INFORMATION: synthetic

<400> SEQUENCE: 150

Cys Gln Asn Glu Ser Tyr Leu Asn Phe Ala Arg Lys Arg Ile Lys Asn
1               5                   10                  15

Cys Asn Phe Ala Arg Lys Arg Ile Lys Asn Pro Glu Gly Gly Leu Tyr
                20                  25                  30

Cys

<210> SEQ ID NO 151
<211> LENGTH: 33
<212> TYPE: PRT
<213> ORGANISM: Artificial Sequence
<220> FEATURE:
<223> OTHER INFORMATION: synthetic

<400> SEQUENCE: 151

Cys Arg Val Asn Asn Ser Asp Pro Tyr Ser Val Ala Leu Ser Glu Leu
1               5                   10                  15

Cys Val Ser Glu Gln Lys Ile Ser Glu Trp Gly Lys Ile Lys Glu Ser
                20                  25                  30

Cys

<210> SEQ ID NO 152
<211> LENGTH: 33
<212> TYPE: PRT
<213> ORGANISM: Artificial Sequence
<220> FEATURE:
<223> OTHER INFORMATION: synthetic

<400> SEQUENCE: 152

Cys Gly Asp Arg Gln Asn Glu Ser Tyr Leu Asn Phe Ala Arg Lys Arg
1               5                   10                  15

Cys Val Ser Glu Gln Lys Ile Ser Glu Trp Gly Lys Ile Lys Glu Ser
                20                  25                  30

Cys

<210> SEQ ID NO 153
<211> LENGTH: 17
<212> TYPE: PRT
<213> ORGANISM: Artificial Sequence
<220> FEATURE:
<223> OTHER INFORMATION: synthetic
```

```
<400> SEQUENCE: 153

Cys Gln Lys Ile Ser Glu Trp Gly Lys Ile Lys Ala Ala Pro Ile Pro
1               5                   10                  15

Cys

<210> SEQ ID NO 154
<211> LENGTH: 33
<212> TYPE: PRT
<213> ORGANISM: Artificial Sequence
<220> FEATURE:
<223> OTHER INFORMATION: synthetic

<400> SEQUENCE: 154

Cys Val Asn Ala Arg Val Asn Asn Ser Asp Pro Tyr Ser Val Ala Leu
1               5                   10                  15

Cys Thr Val Ser Glu Gln Lys Ile Ser Glu Trp Gly Lys Ile Lys Glu
            20                  25                  30

Cys

<210> SEQ ID NO 155
<211> LENGTH: 33
<212> TYPE: PRT
<213> ORGANISM: Artificial Sequence
<220> FEATURE:
<223> OTHER INFORMATION: synthetic

<400> SEQUENCE: 155

Cys Glu Trp Ser Val Asn Ala Arg Val Asn Asn Ser Asp Pro Tyr Ser
1               5                   10                  15

Cys Val Ser Glu Gln Lys Ile Ser Glu Trp Gly Lys Ile Lys Glu Ser
            20                  25                  30

Cys

<210> SEQ ID NO 156
<211> LENGTH: 33
<212> TYPE: PRT
<213> ORGANISM: Artificial Sequence
<220> FEATURE:
<223> OTHER INFORMATION: synthetic

<400> SEQUENCE: 156

Cys Val Arg Gly Gln Thr Ala Glu Ser Leu Ala Val His Asn Ile Thr
1               5                   10                  15

Cys Ser Leu Ala Val His Asn Ile Thr Val Ser Glu Gln Lys Ile Ser
            20                  25                  30

Cys

<210> SEQ ID NO 157
<211> LENGTH: 10
<212> TYPE: PRT
<213> ORGANISM: Artificial Sequence
<220> FEATURE:
<223> OTHER INFORMATION: synthetic

<400> SEQUENCE: 157

Asp Asp Ser Lys Val Phe Lys Glu Gly Ser
1               5                   10

<210> SEQ ID NO 158
<211> LENGTH: 12
<212> TYPE: PRT
<213> ORGANISM: Artificial Sequence
```

```
<220> FEATURE:
<223> OTHER INFORMATION: synthetic

<400> SEQUENCE: 158

Leu Tyr Gly Tyr Arg Trp Pro Leu Pro Ser Lys Leu
1               5                   10

<210> SEQ ID NO 159
<211> LENGTH: 20
<212> TYPE: DNA
<213> ORGANISM: Artificial Sequence
<220> FEATURE:
<223> OTHER INFORMATION: synthetic

<400> SEQUENCE: 159
ttaacagcac gctgatcctg                                                     20

<210> SEQ ID NO 160
<211> LENGTH: 20
<212> TYPE: DNA
<213> ORGANISM: Artificial Sequence
<220> FEATURE:
<223> OTHER INFORMATION: synthetic

<400> SEQUENCE: 160
cactccagtg agaccagcaa                                                     20

<210> SEQ ID NO 161
<211> LENGTH: 25
<212> TYPE: DNA
<213> ORGANISM: Artificial Sequence
<220> FEATURE:
<223> OTHER INFORMATION: synthetic

<400> SEQUENCE: 161
ggagtttcaa gatgcgtgga aacta                                               25

<210> SEQ ID NO 162
<211> LENGTH: 24
<212> TYPE: DNA
<213> ORGANISM: Artificial Sequence
<220> FEATURE:
<223> OTHER INFORMATION: synthetic

<400> SEQUENCE: 162
gccagactca gagttggaga tgct                                                24

<210> SEQ ID NO 163
<211> LENGTH: 20
<212> TYPE: DNA
<213> ORGANISM: Artificial Sequence
<220> FEATURE:
<223> OTHER INFORMATION: synthetic

<400> SEQUENCE: 163
ccagggcagt acatcttggt                                                     20

<210> SEQ ID NO 164
<211> LENGTH: 20
<212> TYPE: DNA
<213> ORGANISM: Artificial Sequence
<220> FEATURE:
<223> OTHER INFORMATION: synthetic

<400> SEQUENCE: 164
ccgtgtttcc agggagagta                                                     20
```

<210> SEQ ID NO 165
<211> LENGTH: 20
<212> TYPE: DNA
<213> ORGANISM: Artificial Sequence
<220> FEATURE:
<223> OTHER INFORMATION: synthetic

<400> SEQUENCE: 165
gcttacctcc gaggatcaca                                               20

<210> SEQ ID NO 166
<211> LENGTH: 19
<212> TYPE: DNA
<213> ORGANISM: Artificial Sequence
<220> FEATURE:
<223> OTHER INFORMATION: synthetic

<400> SEQUENCE: 166
cgggagggtg ggtatctaa                                                19

<210> SEQ ID NO 167
<211> LENGTH: 24
<212> TYPE: DNA
<213> ORGANISM: Artificial Sequence
<220> FEATURE:
<223> OTHER INFORMATION: synthetic

<400> SEQUENCE: 167
atcaagcggc cccctttttt tcac                                          24

<210> SEQ ID NO 168
<211> LENGTH: 24
<212> TYPE: DNA
<213> ORGANISM: Artificial Sequence
<220> FEATURE:
<223> OTHER INFORMATION: synthetic

<400> SEQUENCE: 168
ctcattgtca cactcctcga cagc                                          24

<210> SEQ ID NO 169
<211> LENGTH: 20
<212> TYPE: DNA
<213> ORGANISM: Artificial Sequence
<220> FEATURE:
<223> OTHER INFORMATION: synthetic

<400> SEQUENCE: 169
tcatcatggc agtgtcccta                                               20

<210> SEQ ID NO 170
<211> LENGTH: 20
<212> TYPE: DNA
<213> ORGANISM: Artificial Sequence
<220> FEATURE:
<223> OTHER INFORMATION: synthetic

<400> SEQUENCE: 170
tgagggagga agctgaaaga                                               20

<210> SEQ ID NO 171
<211> LENGTH: 20
<212> TYPE: DNA
<213> ORGANISM: Artificial Sequence
<220> FEATURE:

```
<223> OTHER INFORMATION: synthetic

<400> SEQUENCE: 171
tcaccctgaa gtaccccatc                                              20

<210> SEQ ID NO 172
<211> LENGTH: 18
<212> TYPE: DNA
<213> ORGANISM: Artificial Sequence
<220> FEATURE:
<223> OTHER INFORMATION: synthetic

<400> SEQUENCE: 172
ggctggaaga gtgcctca                                                18

<210> SEQ ID NO 173
<211> LENGTH: 10
<212> TYPE: PRT
<213> ORGANISM: Artificial Sequence
<220> FEATURE:
<223> OTHER INFORMATION: synthetic

<400> SEQUENCE: 173

Thr Trp Tyr Ala His Asn Cys Arg Leu Gln
1               5                   10

<210> SEQ ID NO 174
<211> LENGTH: 11
<212> TYPE: PRT
<213> ORGANISM: Artificial Sequence
<220> FEATURE:
<223> OTHER INFORMATION: synthetic

<400> SEQUENCE: 174

Glu Thr Glu Leu Thr Pro Gln Arg Leu Gln Cys
1               5                   10
```